US009018244B2

(12) United States Patent
Kushner et al.

(10) Patent No.: US 9,018,244 B2
(45) Date of Patent: Apr. 28, 2015

(54) BENZOPYRAN COMPOUNDS, COMPOSITIONS AND USES THEREOF

(71) Applicant: Olema Pharmaceuticals, Inc., San Francisco, CA (US)

(72) Inventors: Peter J. Kushner, San Francisco, CA (US); David C. Myles, Berkeley, CA (US); Cyrus L. Harmon, Bolinas, CA (US); Leslie Carol Hodges Gallagher, Alameda, CA (US)

(73) Assignee: Olema Pharmaceuticals, Inc., San Francisco, CA (US)

( * ) Notice: Subject to any disclaimer, the term of this patent is extended or adjusted under 35 U.S.C. 154(b) by 0 days.

(21) Appl. No.: 13/717,326

(22) Filed: Dec. 17, 2012

(65) Prior Publication Data

US 2013/0178445 A1   Jul. 11, 2013

Related U.S. Application Data

(60) Provisional application No. 61/576,890, filed on Dec. 16, 2011.

(51) Int. Cl.
| | |
|---|---|
| *C07D 405/12* | (2006.01) |
| *A61K 31/4025* | (2006.01) |
| *A61K 31/565* | (2006.01) |
| *A61K 31/675* | (2006.01) |
| *A61K 45/06* | (2006.01) |
| *C07F 9/6558* | (2006.01) |

(52) U.S. Cl.
CPC .......... *A61K 31/4025* (2013.01); *A61K 31/565* (2013.01); *A61K 31/675* (2013.01); *A61K 45/06* (2013.01); *C07D 405/12* (2013.01); *C07F 9/65586* (2013.01)

(58) Field of Classification Search
None
See application file for complete search history.

(56) References Cited

U.S. PATENT DOCUMENTS

| | | | |
|---|---|---|---|
| 4,418,068 | A | 11/1983 | Jones |
| 4,659,516 | A | 4/1987 | Bowler et al. |
| 5,254,568 | A | 10/1993 | Kapil et al. |
| 5,393,763 | A | 2/1995 | Black et al. |
| 5,395,842 | A | 3/1995 | Labrie et al. |
| 5,407,947 | A | 4/1995 | Bryant et al. |
| 5,446,061 | A | 8/1995 | Bryant et al. |
| 5,446,071 | A | 8/1995 | Grese |
| 5,457,117 | A | 10/1995 | Black et al. |
| 5,478,847 | A | 12/1995 | Draper |
| 5,637,598 | A | 6/1997 | Grese |
| 5,686,465 | A | 11/1997 | Labrie et al. |
| 5,840,735 | A | 11/1998 | Labrie et al. |
| 5,980,938 | A | 11/1999 | Berg et al. |
| 6,060,503 | A | 5/2000 | Labrie et al. |
| 6,262,270 | B1 | 7/2001 | Draper et al. |
| 6,326,392 | B1 | 12/2001 | Gast et al. |
| 6,465,445 | B1 | 10/2002 | Labrie |
| 6,638,727 | B1 | 10/2003 | Hung et al. |
| 6,774,122 | B2 | 8/2004 | Evans et al. |
| 6,844,336 | B2 | 1/2005 | Kuenzer et al. |
| 7,005,428 | B1 | 2/2006 | Labrie |
| 7,138,426 | B2 | 11/2006 | DiNinno et al. |
| 7,456,160 | B2 | 11/2008 | Evans et al. |
| 8,299,112 | B2 | 10/2012 | Smith et al. |
| 8,455,534 | B2 | 6/2013 | Smith et al. |
| 8,703,810 | B2 | 4/2014 | Kahraman et al. |
| 8,853,423 | B2 | 10/2014 | Govek et al. |
| 2009/0082467 | A1 | 3/2009 | Fisch |
| 2010/0317635 | A1 | 12/2010 | Labrie |
| 2011/0312925 | A1 | 12/2011 | Labrie |
| 2012/0071535 | A1 | 3/2012 | Smith et al. |
| 2013/0012561 | A1 | 1/2013 | Smith et al. |
| 2013/0116232 | A1* | 5/2013 | Kahraman et al. ....... 514/210.19 |
| 2013/0116258 | A1 | 5/2013 | Smith et al. |
| 2013/0137746 | A1 | 5/2013 | Govek et al. |
| 2013/0231333 | A1 | 9/2013 | Smith et al. |
| 2014/0107095 | A1 | 4/2014 | Kahraman et al. |
| 2014/0199236 | A1 | 7/2014 | Chen et al. |

FOREIGN PATENT DOCUMENTS

| | | |
|---|---|---|
| AU | 2009200258 B2 | 2/2009 |
| BR | PI0703735-0 A2 | 9/2009 |
| EP | 1 167 364 A1 | 1/2002 |
| WO | WO 93/10741 A2 | 6/1993 |

(Continued)

OTHER PUBLICATIONS

Ruff M. et al., "Estrogen Receptor Transcription and Transactivation Structure-Function Relationship in DNA- and Ligand-Binding Domains of Estrogen Receptors", Breast Cancer Research 2(5):353-359 (2000).
International Search Report and Written Opinion dated Feb. 26, 2013 received from the International Searching Authority and related Application No. PCT/US12/70168.
Baer P.G. et al., "Lack of Effect on Bone of 28-Days Treatment of OVX and Intact Rats With a Pure Anti-Estrogen", Calcified Tissue International-Abstracts of the First International Conference on Steroids and Bone 54:329-362 (May 19-21, 1994) (p. 338).
Biskobing D.M., "Update on Bazedoxifene: A Novel Selective Estrogen Receptor Modulator", Clinical Interventions in Aging 2(3):299-303 (2007).
Blizzard T.A. et al., "Estrogen Receptor Ligands. Part 9: Dihydrobenzoxathiin SERAMs With Alkyl Substituted Pyrrolidine Side Chains and Linkers", Bioorganic & Medicinal Chemistry Letters 15:107-113 (2005).

(Continued)

*Primary Examiner* — Michael Barker
(74) *Attorney, Agent, or Firm* — Scully, Scott, Murphy & Presser, P.C.

(57) ABSTRACT

Benzopyran compounds with strong anti-estrogenic activity and essentially no estrogenic activity are provided, which are OP-1038, which is 3-(4-hydroxyphenyl)-4-methyl-2-(4-{2-[(3R)-3-methylpyrrolidin-1-yl]ethoxy}phenyl)-2H-chromen-7-ol, and OP-1074, which is (2S)-3-(4-hydroxyphenyl)-4-methyl-2-(4-{2-[(3R)-3-methylpyrrolidin-1-yl]ethoxy}phenyl)-2H-chromen-7-ol. OP-1074 is a pure anti-estrogen when tested in the agonist mode and a complete anti-estrogen when tested in the antagonist mode. These compounds are useful for the treatment or prevention of a variety of conditions that are modulated through the estrogen receptor in mammals including humans.

50 Claims, 18 Drawing Sheets

(56) References Cited

FOREIGN PATENT DOCUMENTS

| WO | WO 95/17891 A1 | 7/1995 |
| WO | WO 96/26201 A1 | 8/1996 |
| WO | WO 99/02512 A1 | 1/1999 |
| WO | WO 99/28344 A2 | 6/1999 |
| WO | WO 99/63974 A2 | 12/1999 |
| WO | WO 00/09493 A1 | 2/2000 |
| WO | WO 00/37083 A1 | 6/2000 |
| WO | WO 01/01969 A2 | 1/2001 |
| WO | WO 01/26651 A2 | 4/2001 |
| WO | WO 01/54699 A1 | 8/2001 |
| WO | WO 01/68634 A1 | 9/2001 |
| WO | WO 03/041654 A2 | 5/2003 |
| WO | WO 2004/091488 A2 | 10/2004 |
| WO | WO 2006/042409 A1 | 4/2006 |
| WO | WO 2010/145010 A1 | 12/2010 |
| WO | WO 2011/103202 A2 | 8/2011 |
| WO | WO 2011/156518 A2 | 12/2011 |
| WO | WO 2011/159769 A2 | 12/2011 |
| WO | WO 2012/037410 A2 | 3/2012 |
| WO | WO 2013/090829 A1 | 6/2013 |
| WO | WO 2013/090836 A1 | 6/2013 |
| WO | WO 2013/184681 A1 | 12/2013 |
| WO | WO 2014018926 A1 | 1/2014 |
| WO | WO 2014052237 A1 | 4/2014 |

OTHER PUBLICATIONS

Blizzard T.A. et al., "Estrogen Receptor Ligands. Part 13: Dihydrobenzoxathiin SERAMs With an Opitimzed Antagonist Side Chain", Bioorganic & Medicinal Chemistry Letters 15:3912-3916 (2005).

Blizzard T.A. et al., "Estrogen Receptor Ligands. Part 14: Application of Novel Antagonist Side Chains to Existing Platforms", Bioorganic & Medicinal Chemistry Lettters 15:5124-5128 (2005).

Blizzard T.A. et al., "Selective Estrogen Receptor Modulator Medicinal Chemistry at Merck. A Review", Current Topics in Medicinal Chemistry 8:792-812 (2008).

Dodge J.A. et al., "Effects of Steroidal and Non-Steroidal Anti-Estrogens in the Ovariectomized Rat", J. Bone Miner. Res. 8(Suppl 1):S278 (1993).

Gauthier S. et al., "Synthesis and Structure-Activity Relationships of Analogs of EM-652 (Acolbifene), a Pure Selective Estrogen Receptor Modulator. Study of Nitrogen Substitution", Journal of Enzyme Inhibition and Medicinal Chemistry 20(2):165-177 (Apr. 2005).

Gennari L. et al., "Lasofoxifene: A Third-Generation Selective Estrogen Receptor Modulator for the Prevention and Treatment of Osteoporosis", Expert Opinion Investig. Drugs 15(9):1091-1103 (2006).

Jordan V.C., "Alternate Antiestrogens and Approaches to the Prevention of Breast Cancer", Journal of Cellular Biochemistry, Supplement 22:51-57 (1995).

Katzenellenbogen J.A., "The 2010 Philip S. Portoghese Medicinal Chemistry Lectureship: Addressing the "Core Issue" in the Design of Estrogen Receptor Ligands", Journal of Medicinal Chemistry 54:5271-5282 (2011).

Labrie F. et al., "The Combination of a Novel Selective Estrogen Receptor Modulator With an Estrogen Protects the Mammary Gland and Uterus in a Rodent Model: The Future of Postmenopausal Women's Health?", Endocrinology 144 (11):4700-4706 (Nov. 2003).

Robertson J.F.R. et al., "Activity of Fulvestrant 500 mg Versus Anastrozole 1 mg as First-Line Treatment for Advanced Breast Cancer: Results from the First Study", Journal of Clinical Oncology 27(27):4530-4535 (Sep. 20, 2009).

Sharma A.P. et al., "Structure-Activity Relationship of Antiestrogens. Effect of the Side Chain and its Position on the Activity of 2,3-Diaryl-2H-1-Benzopyrans", J. Med. Chem. 33:3216-3222 (1990).

Sharma A.P. et al., "Structure-Activity Relationship of Antiestrogens. Phenolic Analogues of 2,3-Diaryl-2H-1-Benzopyrans", J. Med. Chem. 33:3222-3229 (1990).

Tan Q. et al., "Estrogen Receptor Ligands. Part 10: Chromanes: Old Scaffolds for New SERAMs", Bioorganic & Medicinal Chemistry Letters 15:1675-1681 (2005).

Wakeling A.E., "The Future of New Pure Antiestrogens in Clinical Breast Cancer", Breast Cancer and Treatment 25:1-9 (1993).

Wu Y-L et al., "Structural Basis for an Unexpected Mode of SERM-Mediated ER Antagonism", Molecular Cell 18:413-424 (May 13, 2005).

* cited by examiner

BENZOPYRAN COMPOUNDS, COMPOSITIONS AND USES THEREOF

CROSS REFERENCE TO RELATED APPLICATIONS

This application claims priority to U.S. Provisional Application No. 61/576,890, filed on Dec. 16, 2011, the contents of which are incorporated herein by reference.

FIELD

This invention is in the field of pharmaceuticals, and is in particular novel benzopyran compounds, and salts, prodrugs and derivatives thereof and their medical uses, including as estrogen receptor modulators and for medical conditions that would benefit from an anti-estrogenic drug, and pharmaceutical compositions thereof.

BACKGROUND

Estrogen receptor modulators are a class of compounds that act on the estrogen receptor. These compounds can be pure agonists (mimicking estrogen), pure antagonists, or mixed agonist-antagonists (sometimes referred to as Selective Estrogen Receptor Modulators (SERMs)). For example, estradiol (A) is a pure agonist, fulvestrant (B) is a complete antagonist, and tamoxifen (C) and raloxifene (D) are SERMs.

Most breast cancers express estrogen receptors (ER), and their growth is driven by the action of estrogen at its receptors, primarily at ER alpha. This type of cancer is treated with an estrogen antagonist, which competes with estrogen for binding to the receptor, but does not activate it, preventing estrogen driven growth. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors. A recent study also suggests that fulvestrant is substantially superior to the aromatase inhibitor anastrozole in treating metastatic breast cancer (Robertson et al. J Clin Oncol (2009) 27(27):4530-5).

Estradiol is a naturally-occurring female estrogenic hormone. Raloxifene was disclosed by Eli Lilly in 1981 (U.S. Pat. Nos. 4,418,068; 5,478,847; 5,393,763; and 5,457,117) for prevention of breast cancer and treatment of osteoporosis. Fulvestrant was disclosed by Imperial Chemical Industries (ICI) in 1983 (U.S. Pat. No. 4,659,516, expired in 2007 with a patent term extension; U.S. Pat. Nos. 6,774,122 and 7,456,160). Tamoxifen was also disclosed by ICI in the '516 patent. Tamoxifen was developed for the treatment of breast cancer on the basis of strong antagonism of estrogen action in mammary tissue (Jordan, J. Cell. Biochem. 51 (1995)).

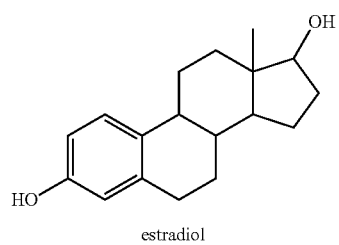

estradiol

A

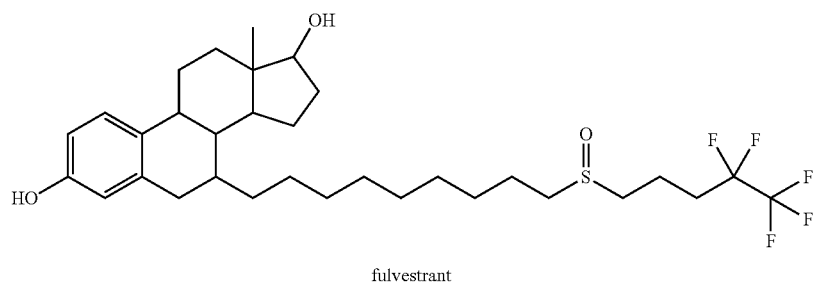

fulvestrant

B

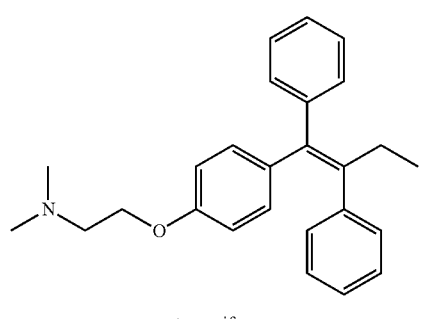

tamoxifen

C

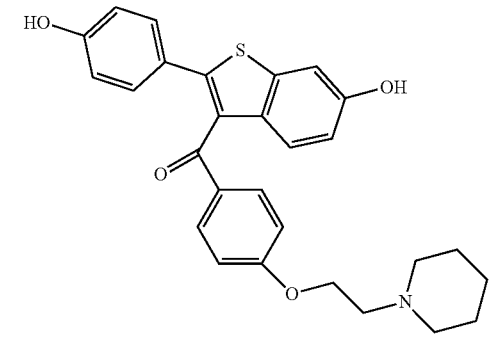

raloxifene

D

The degree of anti-estrogenicity is often assayed by exposing female, immature (preferably ovariectomized) rodents to test doses of the compound both in the absence (agonist mode) and presence (antagonist mode) of estrogen. Tamoxifen and other partial anti-estrogens stimulate uterine weight gain in the agonist mode and only partly block estrogen-driven uterine weight gain in the antagonist mode. Fulvestrant and other complete anti-estrogens do not stimulate uterine weight gain in the agonist mode and completely block estrogen-driven weight gain in the antagonist mode. The induction of estrogen-regulated alkaline phosphatase expression in human uterine cancer cell growth in culture can be used to distinguish partial and complete anti-estrogenicity and correlates well with the rodent weight gain assay.

Tamoxifen and fulvestrant both inhibit cultured human breast cancer cell proliferation provoked by estrogen. However, fulvestrant more fully inhibits the proliferation when provoked with growth factors, especially of the insulin/insulin-like growth factor family. Thus the inhibition of growth-factor driven breast cancer cell proliferation and the effect on uterine weight provide two assays which can distinguish between complete and partial anti-estrogens.

Tamoxifen binding stabilizes the estrogen receptor whereas fulvestrant and chemically related antiestrogens, such as ICI-164384 and RU-58668, cause degradation of the estrogen receptor. (Dodge et al, J. Bone Miner. Res., 8 (Suppl 1, S278 (1993); Wakeling, Breast Cancer Res. Treat. 25, 1 (1993); Baer et al, Calcified Tissue Int., 55, 338 (1994). However, some compounds, like GW-5638 (Wu et al, Mol. Cell., 18, 413 (2005), and OP1075, described below, degrade the receptor but are partial estrogens—that is, not complete anti-estrogens. Thus the ability to degrade the estrogen receptor does not ensure complete antiestrogenicity. The ability to induce degradation of the receptor is nonetheless a factor that differentiates the behavior of tamoxifen and fulvestrant and may be desirable in a drug to treat breast cancer.

Fulvestrant, which degrades the estrogen receptor, incorporates a core of 17-beta estradiol. It has a long flexible aliphatic side chain that blocks oral absorption. The estradiol core blocks oral absorption and the long flexible aliphatic side chain makes the drug very insoluble which worsens the problem. Fulvestrant must be injected because of the poor oral bioavailability. Two 5 ml intramuscular depot injections, one into each buttock, must be administered monthly by a health professional. Furthermore, it is unclear whether these two injections provide sufficient drug exposure for optimal action. The drug does not seem to work in pre-menopausal women.

In 1990, an important step in oral anti-estrogen development came with the discovery of a family of high-affinity benzopyran anti-estrogens by Kapil and coworkers. (Sharma et al. (1990) J Med Chem, 33(12):3222-9; Sharma et al. (1990) J Med Chem, 33(12):3216-22). The numbering scheme of benzopyrans is typically:

F

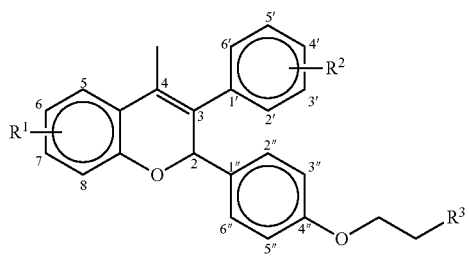

Sharma et al. showed that the combination of 7-hydroxyl and 4'-hydroxyl groups conferred high-affinity binding of the benzopyran core to the estrogen receptor (Compound G; see Compound 25 of Sharma et al. (1990) J Med Chem, 33(12): 3222-9 where $R^1$ and $R^2$ are OH).

G

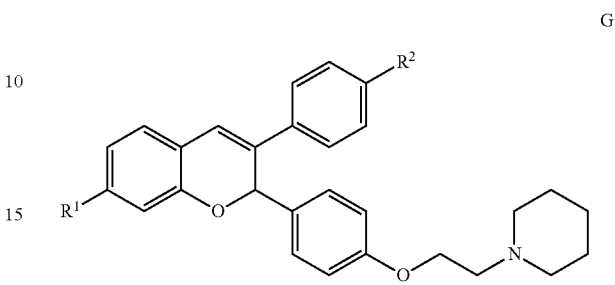

Further, Sharma et al. reported that the presence of a methyl group at the 4 position of the benzopyran core enhanced receptor binding affinity, without a hydroxyl group at the 4'-position.

In 1991, Labrie and coworkers filed a patent application which issued as U.S. Pat. No. 5,395,842 (see claim 29) which taught that EM-343 (H), showed superior binding to the estrogen receptor with no loss of anti-estrogen action. EM-343 differed from the Saeed compounds by including the hydroxyl at the 4'-position of a 4-methyl, 7-hydroxyl benzopyran.

H

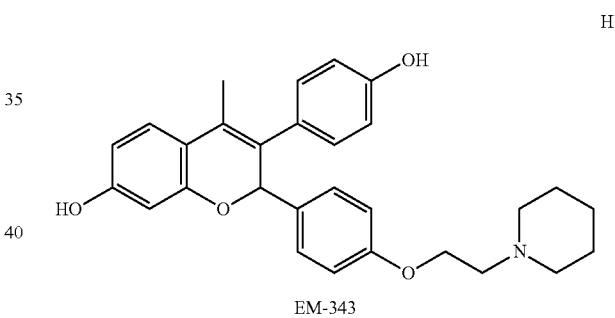

EM-343

In 1995, Labrie et al. filed a continuation-in-part patent application, which issued in 2000 as U.S. Pat. No. 6,060,503, disclosing prodrugs and optically active species of EM-343. Particularly, Labrie et al. disclosed a pure isomer of EM-343, EM-652, referred to as acolbifene (I), which is (S)-3-(4-hydroxyphenyl)-4-methyl-2-(4-(2-(piperidin-1-yl)ethoxy) phenyl)-2H-chromen-7-ol.

I

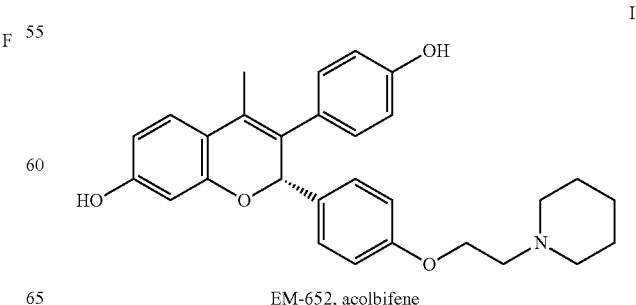

EM-652, acolbifene

Labrie et al. in WO 01/54699 (see FIGS. 4a and 4b) also presented several broad generic Markush formulae of benzopyran-containing compounds, including acolbifene analogs, in which the side chain terminates in various substituted ring systems including pyrrolidinyl, piperidinyl, and methyl-1-pyrrolidinyl and dimethyl-1-pyrrolidinyl.

U.S. Pat. Nos. 7,005,428 and 6,465,445 to Labrie, which claim priority to a June 1998 application describe the following generic formulas for use as anti-estrogenic compounds:

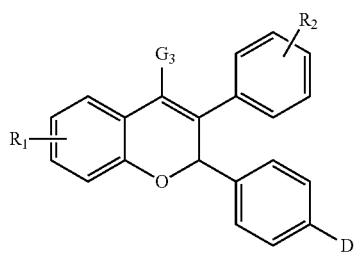

wherein D is —OCH$_2$CH$_2$N(R$_3$)R$_4$ (R$_3$ and R$_4$ either being independently selected from the group consisting of C$_1$-C$_4$ alkyl, or R$_3$, R$_4$ and the nitrogen atom to which they are bound together being a ring structure selected from the group consisting of pyrrolidino, dimethyl-1-pyrrolidino, methyl-1-purrolidinyl, piperidino, hexamethyleneimino and morpholino); and wherein R$_1$ and R$_2$ are independently selected from the group consisting of hydrogen, hydroxyl and a moiety converted in vivo in to hydroxyl, and

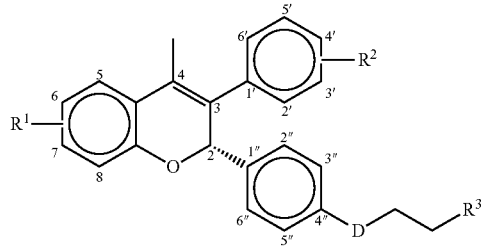

wherein R$_1$ and R$_2$ are independently selected from the group consisting of hydroxyl and a moiety converted in vivo in to hydroxyl;

wherein R$_3$ is a species selected from the group consisting of saturated, unsaturated or substituted pyrrolidinyl, saturated, unsaturated or substituted piperidino, saturated, unsaturated or substituted piperidinyl, saturated, unsaturated or substituted morpholino, nitrogen-containing cyclic moiety, nitrogen-containing polycyclic moiety, and NRaRb (Ra and Rb being independently hydrogen, straight or branched C$_1$-C$_6$ alkyl, straight or branched C$_2$-C$_6$ alkenyl, and straight of branched C$_2$-C$_6$ alkynyl.

Acolbifene binds to the estrogen receptor alpha with three times the affinity of 17-beta estradiol, the native ligand (Katzenellenbogen (2011) J Med Chem 54(15):5271-82). Since anti-estrogens must compete with estradiol for binding to the estrogen receptor, high affinity binding is an important drug virtue. Both the Labrie '842 and the Labrie '503 patents disclosed benzopyran compounds that can contain an unsubstituted pyrrolidine in the "tail" or R$^3$ position as depicted in Compound F. EM-800, a pivalate prodrug of EM-652, and HCl salts of EM-652 were also described in the '503 patent.

Acolbifene was initially thought to be a complete antiestrogen. However, careful studies with the rodent uterine assay and human uterine cell alkaline phosphatase assays revealed that it retained some estrogen-like action, about 12% that of estradiol (Labrie et al. "The combination of a novel selective estrogen receptor modulator with an estrogen protects the mammary gland and uterus in a rodent model: the future of postmenopausal women's health?" Endocrinology. 2003 144(11):4700-6). This contrasts with fulvestrant where the residual estrogen-like action is almost unmeasurable. Furthermore, fulvestrant binding induces dramatic degradation of the estrogen receptor, while acolbifene induces either no or modest receptor degradation. Raloxifene and bazedoxifene don't degrade the receptor, but stabilize the receptor to a much lesser degree than tamoxifen.

Acolbifene is orally bioavailable and is currently being positioned for Phase III clinical trials for the treatment of breast cancer by the Canadian company Endoceutics (Founded by Dr. Labrie). A daily oral dose of 40 mg of acolbifene or EM800 in women produces mean drug exposures of 8.3 and 15 ng/ml of circulating acolbifene, respectively. In preclinical studies both forms of the drug are effective against tamoxifen-resistant human breast cancer xenografts growing on immunocompromised mice. In clinical studies the 40 mg dose of EM800 was numerically as effective as anastrozole in preventing progression of metastatic estrogen receptor positive breast cancer.

Starting in 2005, Blizzard and coworkers at Merck published a series of papers on estrogen receptor ligands. They first focused on using a dihydrobenzoxathiin core (J) with alkyl substituted pyrrolidine side chains and linkers as SERAMs (Selective Estrogen Receptor Alpha Modulators) (Blizzard et al. (2005) Bioorg Med Chem. Lett. 15(1):107-13).

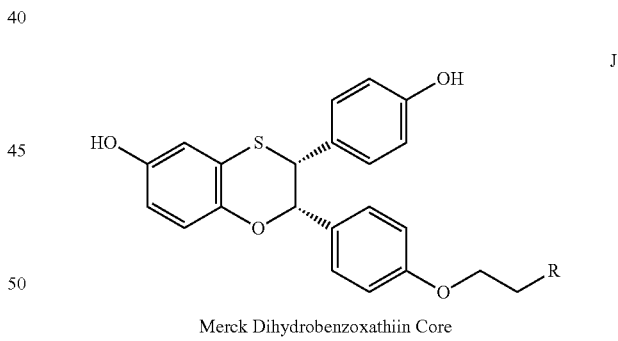

Merck Dihydrobenzoxathiin Core

The group tried to maximize the estrogen receptor αβ selectivity ratio and minimize uterine activity (e.g., maximize antagonism of uterine activity). They reported that the unbranched linker with 3-methylpyrrolidinyl and 3,4-methylpyrrolidinyl as well as the α-methyl (i.e., a methyl on the α-position of the ethylene) linker with an unsubstituted pyrrolidinyl side chains were noteworthy. Blizzard et al. concluded that minor modifications in the side chain or linker resulted in significant effects on biological activity, especially in uterine tissue.

Blizzard et al. also studied a chromane core (Blizzard et al. (2005) Bioorg Med Chem. Lett. 15(6):1675-81) (Compound K).

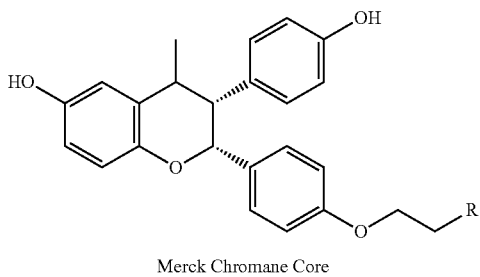

Merck Chromane Core

The Merck chromane core differs from the acolbifene core by the absence of a double bond in the oxane ring. These structures also had a hydroxyl at position 6 (not 7) of the fused benzene ring. A chromane core with a 2-methylpyrrolidine (but not a 3-methyl) with a methyl on the linker created a nearly complete anti-estrogen, (see compound 12 of the Blizzard et al. paper). Blizzard et al. commented on the differences among anti-estrogenic activities of variously substituted cores, and noted that the size and stereogenic placement of substituents is crucial for receptor potency and selectivity.

In the third publication of this series (Blizzard et al. (2005) Bioorg Med Chem. Lett. 15(17):3912-6); Blizzard et al. again studied the dihydrobenzoxathiin core and reported that their studies have resulted in the discovery that addition of a methyl group to the side chain at the appropriate position and with the right stereochemistry, either on the pyrrolidine ring or on the linker substantially increased estrogen antagonist activity in uterine tissue. Blizzard et al. also reported that the best estrogen antagonist activity in this dihydrobenzoxathiin series was determined to have a methyl group on the pyrrolidine and a methyl group on the linker, with the hydroxyl in the 6-position of the fused benzene ring. Blizzard et al. also noted that to their knowledge, their optimized side chain with two methyl groups represented the first example where a relatively small structural modification of an existing SERM resulted in a conversion of a SERM to a SERAM/SERD (Selective Estrogen Receptor alpha Modulator and Downregulator).

The Merck team then investigated whether the optimized side chain modification reported for the dihyrobenzoxathiin core was "portable" and could confer strong anti-estrogenicity when appended to different cores (Blizzard et al. (2005) Bioorg Med Chem Lett. 15(23):5214-8). Merck demonstrated that none of the three cores tested (raloxifene, bazedoxifene, or lasofoxifene) became more anti-estrogenic with either the 3-methyl pyrrolidine or the chiral side chain modifications. Blizzard et al. concluded that "The lack of a dramatic effect on the uterine profile upon incorporation of side chains A and B clearly indicates that the side chain Structure Activity Relationship of the dihydrobenzoxathiin SERAMs is not transferable to other platforms."

In yet another 2005 research publication, Gauthier, Labrie and colleagues reported the synthesis and structure-activity relationships of analogs of acolbifene (Gauthier et al. (2005) J Enzyme Inhib Med Chem, 20(2):165-77). They attempted to improve on the anti-estrogenicity of acolbifene by creating analogs in which the terminal piperidine was either replaced by pyrrolidine or substituted in various ways. All of these analogs proved to be more estrogenic than acolbifene as revealed by the rodent uterus assay. This experience suggests that improvement of the anti-estrogenicity of acolbifene will be a challenge and modifications provide unpredictable results.

Blizzard reviewed the Merck research on anti-estrogens in 2008 (Curr Top Med. Chem. 8(9):792-812). He noted that:

"Selective Estrogen Receptor Modulators (SERMs) have been the subject of extensive medicinal chemistry efforts at several pharmaceutical companies, including Merck . . . . The Merck SERM project involved a large number of talented and dedicated chemists and biologists who worked for several years to discover novel classes of SERMs with a range of selectivities . . . no drugs have yet reached the market as a result of this effort."

Indeed, the Merck effort began in the early 1990's and continued well into the 2000's, reflecting impressive science but no commercial products. Their most promising compounds, which included side chains in which the piperidine ring was replaced with a mono- or di-substituted pyrrolidine ring appended to a benzoxathiin core, especially with a 3-R methylpyrrolidine terminus, showed anti-estrogenicity, although not as complete as fulvestrant in the rodent uterus assay. A chiral methyl on atom 2 of the flexible linker also conferred improved anti-estrogenicity. The two features together in a doubly substituted side chain conferred anti-estrogenicity that was similar to fulvestrant. Unfortunately the Merck core had problematic reactive metabolites when investigated in primates, which halted clinical development.

Aragon Pharmaceuticals filed PCT/US2011/039669 (published Dec. 15, 2011 as WO2011/156518), which claimed priority to U.S. Provisional Application 61/353,531 titled "Estrogen Receptor Modulators and Uses Thereof" filed in June 2010. Aragon disclosed large genuses of benzopyran derivatives and at least 71 acolbifene analogs intended for treatment of tamoxifen resistant breast cancer. Aragon appears to have taken the prior art teachings of Merck regarding how to optimize the dihydrobenzoxathiin core, and applied the teachings to the acolbifene benzopyran core. Aragon is considering advancing a drug to the clinic for late stage progressive metastatic disease.

Bazedoxifene is a SERM, under development for prevention and treatment of postmenopausal osteoporosis (Biskobing, D. M. (2007) Clinical interventions in aging 2 (3): 299-303). Lasofoxifene is another SERM under development for the treatment of postmenopausal osteoporosis and vaginal atrophy (Gennari et al. (2006), Expert Opin Investig Drugs 15 (9): 1091-103).

U.S. Pat. No. 5,254,568 discloses benzopyrans as anti-estrogenic agents.

WO2010/145010 discloses a combination of SERM and sex steroid precursor for treating hot flashes and other symptoms.

WO2004/091488 discloses benzopyrans as estrogen receptor modulators.

U.S. Pat. No. 5,840,735 discloses benzopyrans as sex steroid activity inhibitors.

U.S. Pat. No. 6,262,270 discloses a method for the enantiomeric synthesis of acolbifene derivatives.

The object of the present invention is to provide a new improved anti-estrogenic compound for the treatment of medical disorders that are mediated or affected by an estrogen receptor and pharmaceutical compositions and uses thereof.

SUMMARY OF THE INVENTION

The present invention is based on the discovery that a specific benzopyran (in the form of a mixture of S—C2 and R—C2 diastereomers and also its pure S-diastereomer) has an unexpected combination of improved properties for the treatment of medical disorders that are modulated or affected by an estrogen receptor. It was surprisingly found that a benzopyran core with the combination of: i) a mono-substituted 3-methylpyrrolidyl in the side chain, ii) wherein the 3-methylpyrrodinyl is in the R-stereoconfiguration, iii) hydroxyl groups are positioned on the 7 and 4'-position and iv) with no methyl substitution in the linker moiety provides an optimal anti-estrogenic effect with almost no estrogenic activity. It is surprising that in none of the publications of the years of research at Merck nor in the Aragon PCT application WO2011/156518 was the optimal species disclosed or taught.

The compounds are depicted below as OP-1038 and OP-1074. The chemical name for OP-1038 is 3-(4-hydroxyphenyl)-4-methyl-2-(4-{2-[(3R)-3-methylpyrrolidin-1-yl]ethoxy}phenyl)-2H-chromen-7-ol. The chemical name for OP-1074 is (2S)-3-(4-hydroxyphenyl)-4-methyl-2-(4-{2-[(3R)-3-methylpyrrolidin-1-yl]ethoxy}phenyl)-2H-chromen-7-ol. OP-1074 exhibits essentially no estrogenic activity in the alkaline phosphatase assay in ECC-1 cells. In addition, OP-1074 is a pure anti-estrogen when tested in the agonist mode and a complete anti-estrogen when tested in the antagonist mode.

The general structure methyl-1-pyrrolidinyl can refer to 2-methyl or 3-methyl pyrrolidinyl (wherein the methyl group is attached to the second or third carbon in the pyrrolidine ring) and in each, because the carbon attached to the methyl is chiral, there are possible R and S stereoconfigurations for each. The specific benzopyrans, OP-1038 and pure S-form OP-1074 have a 3-R-methyl-pyrrolidinyl. It has been discovered, contrary to the Merck and Aragon teachings, that a single substitution in the side chain of a benzopyran, in the very specific position of a methyl in the 3-position of a pyrrolidinyl ring, and with R stereochemistry in combination with an unsubstituted linker group has excellent anti-estrogenic properties with the minimal estrogenic effect. As any degree of estrogenic activity may provide risk to a patient with estrogen-receptor positive cancer, a decrease in estrogenic effect can be therapeutically important and represents an advance in the art.

The active compound can be provided if desired as a pharmaceutically acceptable salt, solvate, hydrate, prodrug, stereoisomer, tautomer, N-oxide or $R^1$ and/or $R^2$-substituted derivative optionally in a pharmaceutically acceptable composition to treat a disorder that is modulated or affected by an estrogen receptor, including those treatable with an anti-estrogenic compound optimally with virtually no estrogenic effect.

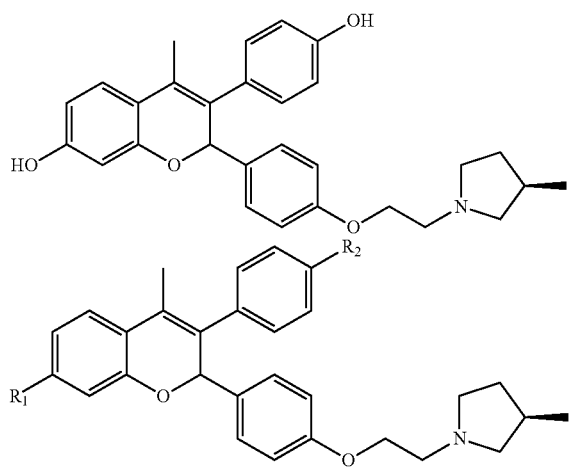

OP-1038

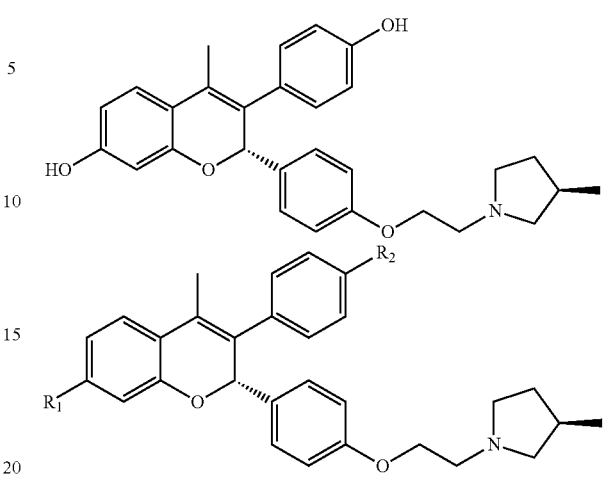

OP-1074

OP-1038 and OP-1074 have two chiral carbons and thus there are four possible diastereomers. The chiral carbon at the C2 position is in the S-configuration in OP-1074 (the same configuration in EM-652, acolbifene) and is a mixture of R and S in OP-1038.

As Merck has previously reported, minor modifications in the side chain or linker of anti-estrogenic agents have been proven to result in significant and unpredictable effects on biological activity, especially in uterine tissue. The inventors have unexpectedly discovered a single orally available compound that provides optimal anti-estrogenic activity with minimal or essentially no estrogenic effect.

The prior art, and notably the Merck results, suggest that achieving full anti-estrogenic properties requires two features in the molecule. First, the core must be modified from the original acolbifene core by moving the hydroxyl from position 7 to position 6 to resemble the two cores in which the Merck team had success—even if that might confer a diminution of binding affinity for the estrogen receptor. Second, the prior art taught that optimal anti-estrogenicity would be achieved by appending a side chain with a 2- or 3-methyl pyrrolidine terminus and a chiral methyl on the linker. That a single substitution would be insufficient (as opposed to a significant improvement, as seen here) is strongly suggested by the experience of the Merck team both with the benzoxathiin core and especially with the chromane core. When a 3-methylpyrrolidine is appended to the chromane core the subsequent compound (number 6, in Blizzard 10) is a partial anti-estrogen with substantial estrogen-like activity, 31% of that of estradiol, in the rat uterine weight gain assay.

Further, the Aragon PCT WO2011/156518 follows the teachings of Merck wherein of its 71 disclosed benzopyran species, 68 have the hydroxyls in the 6 and 4'-positions. Of the others, only one Aragon species has hydroxyls located at the 7 and 4'-positions, and that compound has a methyl in the linker as well as on the pyrrolidine ring (again following the Merck teaching) (Aragon's Compound 28). FIG. 3 illustrates that the compound of the present invention has less estrogenic activity than Aragon Compound 28.

OP-1038 and OP-1074 also induce substantial degradation of the estrogen receptor, comparable to that of fulvestrant and Aragon Compound 28.

The addition of a methyl modification to the linker of a compound with the 3-methylpyrrolidine, contrary to expectations raised by the Merck experience, actually makes the doubly modified molecule (Compound 28 of WO2011/156518) more estrogenic.

OP-1038, OP-1074 and their prodrugs (including esters, carbonates and phosphates), derivatives and their salts are complete anti-estrogens useful to treat locally advanced or metastatic breast cancer that is positive for expression of estrogen receptors, progesterone receptors or both (receptor positive advanced breast cancer). In an alternative embodiment, the compound is used to treat estrogen or progesterone receptor negative breast cancer. The compound can be used as the initial treatment of advanced breast cancer in patients who have never received previous hormonal therapy for advanced breast cancer, either by itself or in combination with one or more other anti-cancer agents, including targeted therapies. They are also useful for second line therapy for treatment after a previous hormonal therapy has failed, either by itself or in combination with another anticancer agent, for example, a targeted therapy such as an mTOR inhibitor such as everolimus.

The compounds of the invention are also useful as adjuvante therapy after surgery to prevent rucurrance. Such adjuvant use is often administered for several years, for instance 5 years, or even up to 10 years after surgery and associated chemotherapy and radiotherapy have been concluded.

The compounds of the invention are also useful for the prevention of breast cancer in women at high risk and can be taken for any desired time period, including indefinitely. For example, a patient, typically a woman, with a family history of breast cancer, or who has been determined to carry a mutation in the BRACA1 or BRACA2 gene or other genes that predispose a patient to breast cancer may choose to use such preventative treatment instead of a mastectomy or other intervention. The compounds described herein are also useful as neoadjuvants to shrink large tumors prior to surgical removal, both to enable breast conservative surgery and to reduce the risk of recurrence. In addition to breast cancer these compounds also are useful to treat other cancers and other overgrowth diseases of the female reproductive tract including ovarian, endometrial, and vaginal cancer and endometriosis. Besides these reproductive tissues the compounds are useful in treating lung cancers that are positive for estrogen or progesterone receptors.

Selective estrogen receptor modulators (SERMS) are useful for hormonal therapy for postmenopausal women in particular to treat or prevent osteoporosis. In one embodiment, a compound of the present invention is used in combination with an estrogen, SERM or partial anti-estrogen such that the complete anti-estrogen prevents adverse action of the total or partial estrogen on the uterus and other tissues.

Other objects and advantages will become apparent to those skilled in the art from a consideration of the ensuing detailed description. All variations and modifications of the disclosed invention are considered within the scope of this invention.

Figure 2:
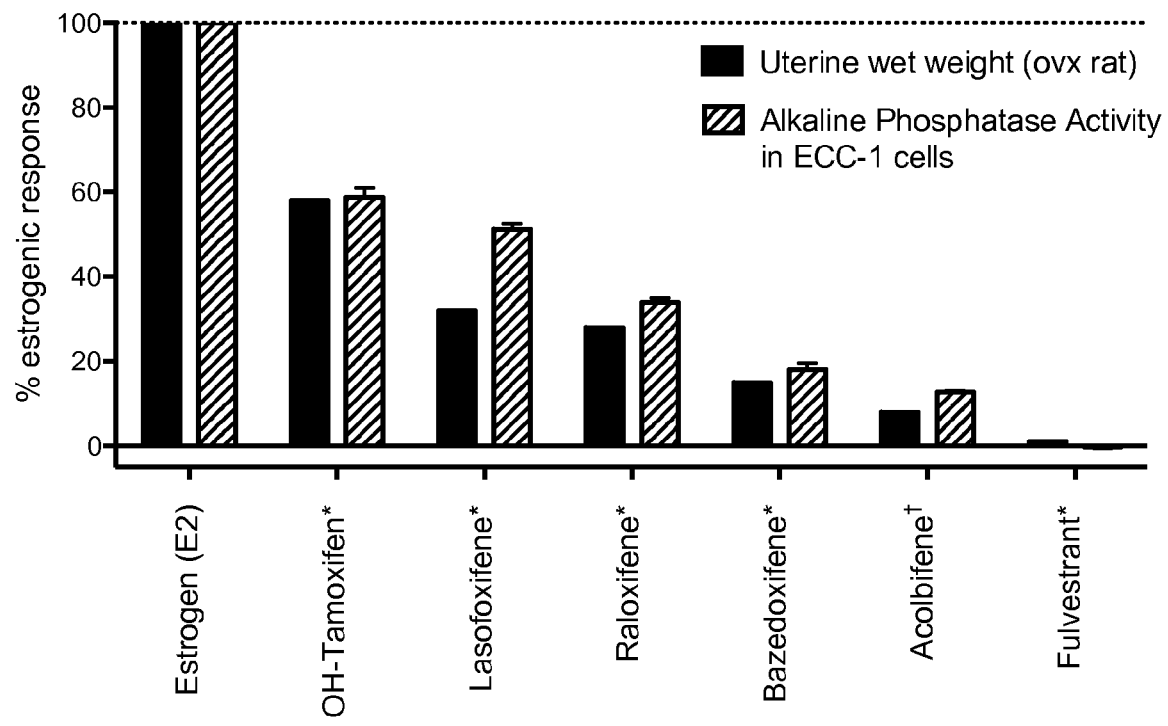

OP-1038 3-(4-hydroxyphenyl)-4-methyl-2-(4-{2-[(3R)-3-methylpyrrolidin-1-yl]ethoxy}phenyl)-2H-chromen-7-ol
OP-1039 3-(4-hydroxyphenyl)-4-methyl-2-(4-{2-[(2R)-2-methylpyrrolidin-1-yl]ethoxy}phenyl)-2H-chromen-7-ol
OP-1040 3-(4-hydroxyphenyl)-4-methyl-2-{4-[2-(pyrrolidin-1-yl)ethoxy]phenyl}-2H-chromen-7-ol
OP-1042 3-(4-hydroxyphenyl)-4-methyl-2-{4-[(2R)-2-[(3R)-3-methylpyrrolidin-1-yl]propoxy]phenyl}-2H-chromen-7-ol
OP-1046 3-(4-hydroxyphenyl)-4-methyl-2-(4-{2-[(3S)-3-methylpyrrolidin-1-yl]ethoxy}phenyl)-2H-chromen-7-ol
OP-1047 3-(4-hydroxyphenyl)-4-methyl-2-(4-{2-[(2S)-2-methylpyrrolidin-1-yl]ethoxy}phenyl)-2H-chromen-7-ol
OP-1049 3-(4-hydroxyphenyl)-4-methyl-2-{4-[(2S)-2-(pyrrolidin-1-yl)propoxy]phenyl}-2H-chromen-7-ol
OP-1050 3-(4-hydroxyphenyl)-4-methyl-2-{4-[(2S)-2-(piperidin-1-yl)propoxy]phenyl}-2H-chromen-7-ol
OP-1053 3-(4-hydroxyphenyl)-4-methyl-2-{4-[(2S)-2-[(2R)-2-methylpyrrolidin-1-yl]propoxy]phenyl}-2H-chromen-7-ol
OP-1056 3-(4-hydroxyphenyl)-2-(4-{2-[(3R)-3-methylpyrrolidin-1-yl]ethoxy}phenyl)-4-(trifluoromethyl)-2H-chromen-7-ol
OP-1060 5-fluoro-3-(4-hydroxyphenyl)-4-methyl-2-{4-[(2S)-2-[(3R)-3-methylpyrrolidin-1-yl]propoxy]phenyl}-2H-chromen-7-ol
OP-1061 5-fluoro-3-(4-hydroxyphenyl)-4-methyl-2-(4-{2-[(3R)-3-methylpyrrolidin-1-yl]ethoxy}phenyl)-2H-chromen-7-ol
OP-1074 (2S)-3-(4-hydroxyphenyl)-4-methyl-2-(4-{2-[(3R)-3-methylpyrrolidin-1-yl]ethoxy}phenyl)-2H-chromen-7-ol
OP-1075 (2R)-3-(4-hydroxyphenyl)-4-methyl-2-(4-{2-[(3R)-3-methylpyrrolidin-1-yl]ethoxy}phenyl)-2H-chromen-7-ol FIG. 2. Alkaline phosphatase (AP) activity in ECC-1 cells correlates with the uterine wet weight of ovariectomized rats, as reported previously in Scafonas, et al. (*; Scafonas et al. "Agonist-like SERM effects on ER alpha-mediated repression of MMPI promoter activity predict in vivo effects on bone and uterus. J Steroid Biochem Mol. Biol. 2008 110(3-5):197-206) and Labrie, et al. (†; Labrie et al. "The combination of a novel selective estrogen receptor modulator with an estrogen protects the mammary gland and uterus in a rodent model: the future of postmenopausal women's health?" Endocrinology. 2003 144(11):4700-6). ECC-1 cells were treated with 500 pM 17β-estradiol (E2) or 1-5 nM anti-estrogens in hormone-depleted medium for 3 days. Note that the racemic mixture of acolbifene, EM-343, was used in the in vitro AP assay. AP activity was measured by incubating a chromogenic AP substrate, p-nitrophenyl phosphate, at 40° C. for 40 minutes followed by measuring the absorbance at 405 nm. Results were from a single representative experiment and reported as the mean percent induction relative to E2 from triplicate treatments, with error bars representing SEM.

Figure 3:
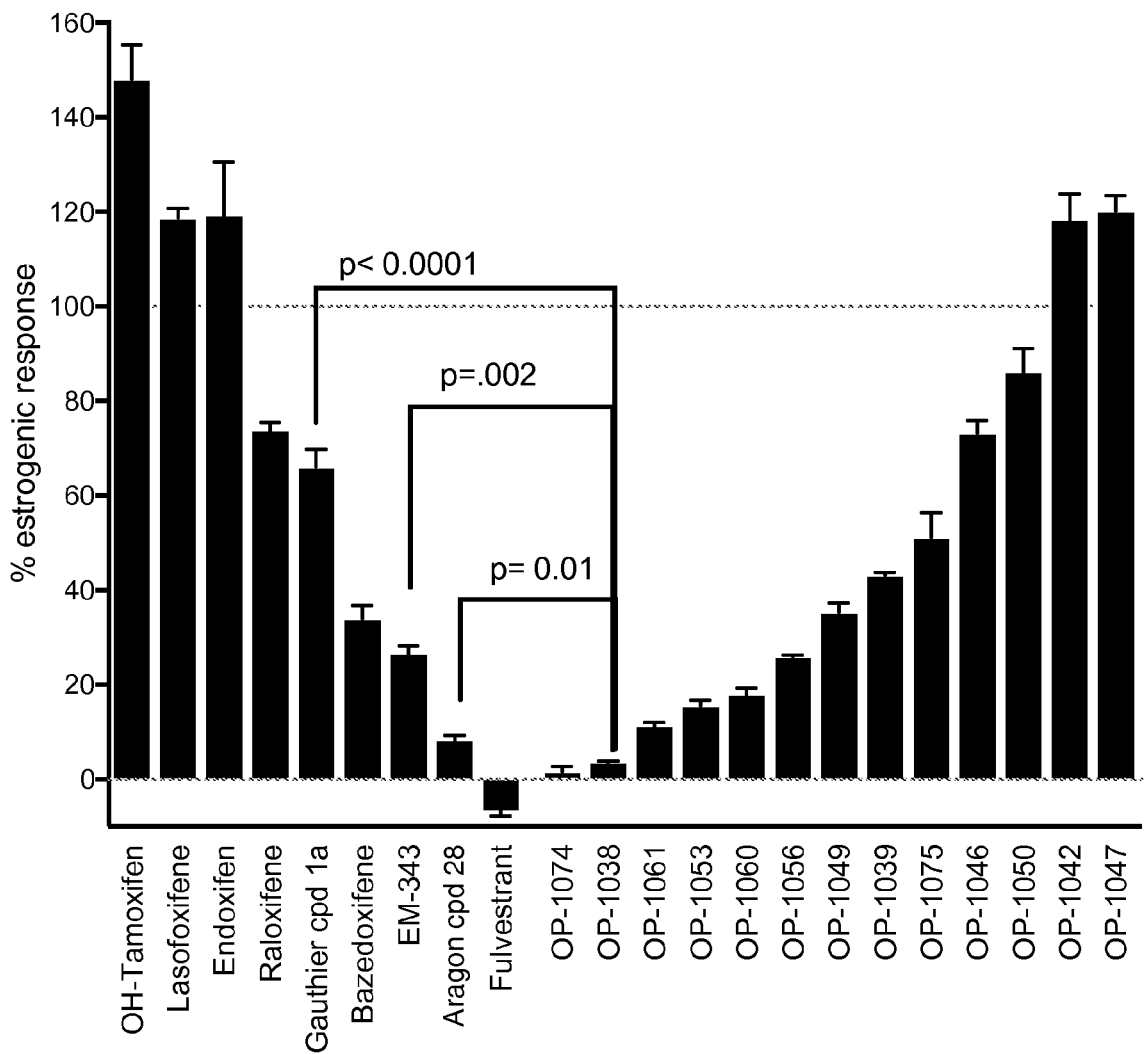

FIG. 3. OP-1038 and OP-1074 lack estrogenic activity in the alkaline phosphatase (AP) assay in ECC-1 cells. Comparison of estrogenic-like AP activity of various benzopyran compounds (right) compared to published reference compounds (left). ECC-1 cells were treated with 100 nM anti-estrogens and AP activity was measured as described in FIG. 2. Results were from a single representative experiment and reported as the mean percent induction relative to E2 from triplicate treatments, with error bars representing SEM. Note that OP-1038 was statistically different from Aragon Compound 28 (WO2011/156518), EM-343 and Gauthier compound Ia (p≤0.01 (exact p values stated in graph), calculated using Student's t-test).

Figure 4:
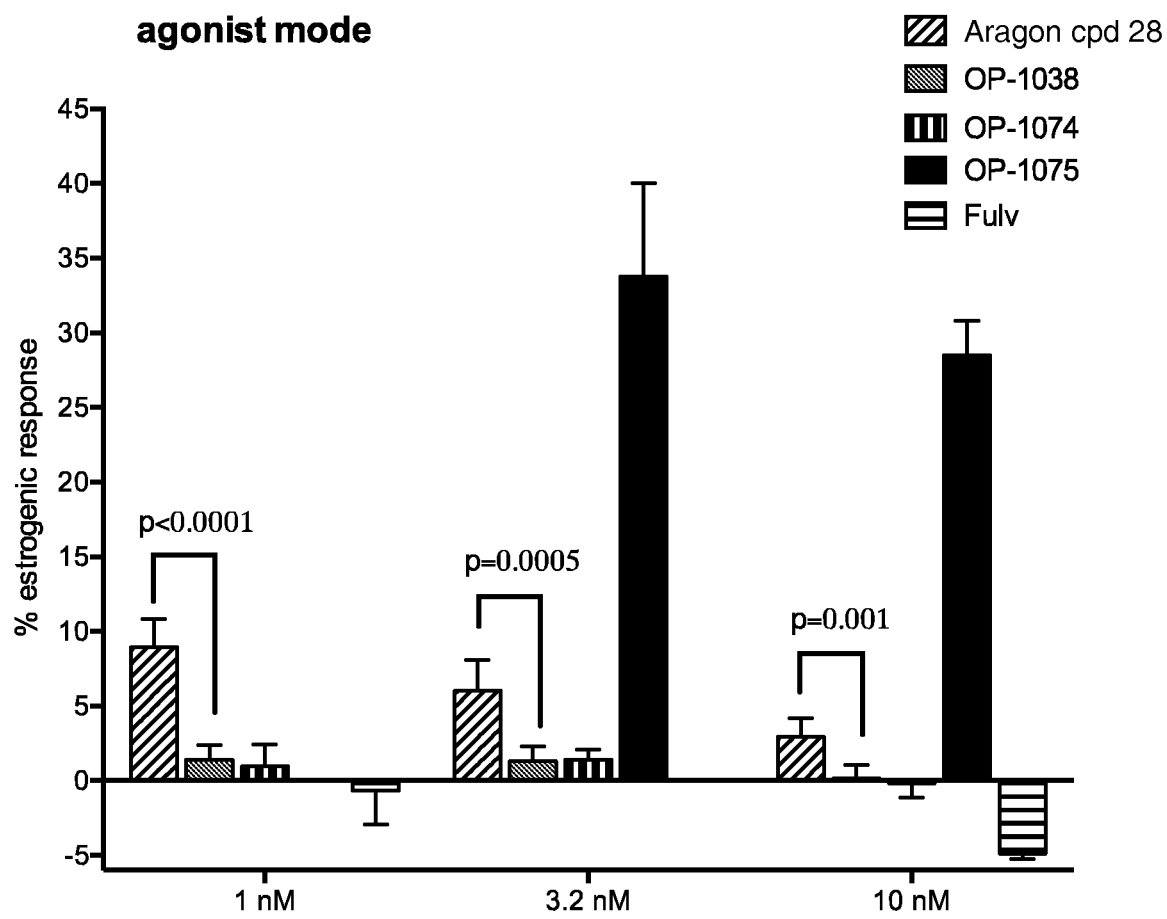

FIG. 4. OP-1038 is less estrogenic than Aragon Compound 28 at three different doses in the AP assay in ECC-1 cells. AP activity was measured as described in FIG. 2. Results were from a single representative experiment and reported as the mean percent induction relative to E2 from sextuplicate treatments, with error bars representing SEM. Note that OP-1038 was statistically different from Aragon Compound 28 at all three doses tested (($p<0.001$ (exact p values stated in graph), calculated using Student's t-test).

Figure 5:
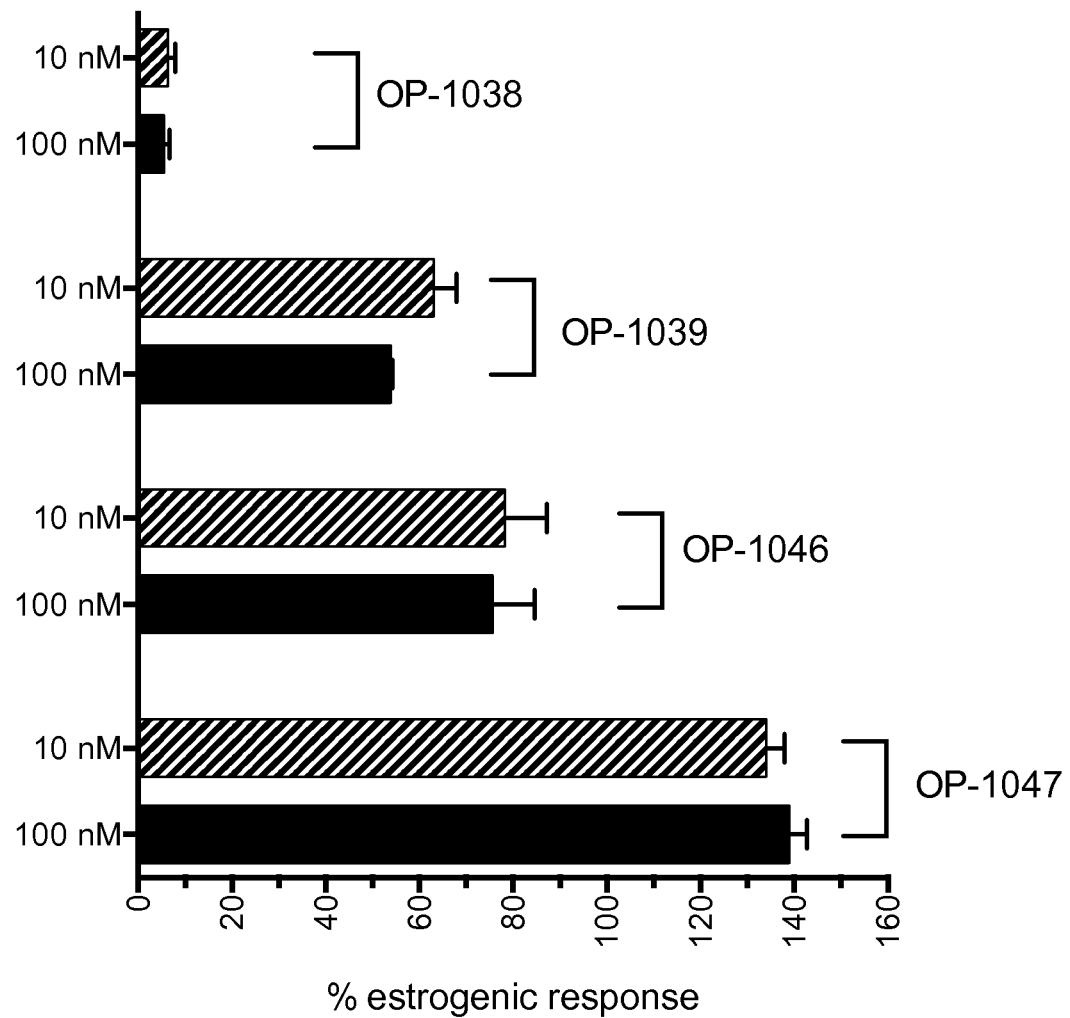

FIG. 5. OP-1038 lacks estrogenic activity in the AP assay in ECC-1 cells, in contrast to other mono-methyl substituted pyrrolidines. AP activity was measured as described in FIG. 2. Results were from a single representative experiment and reported as the mean percent induction relative to E2 from triplicate treatments, with error bars representing SEM.

FIG. 6. OP-1038 and OP-1074 inhibit E2-stimulated AP activity in ECC-1 cells. A) Comparison of inhibition of E2-stimulated AP activity of various benzopyran compounds (right) compared to published reference compounds (left). ECC-1 cells were treated with 100 nM anti-estrogens in the presence of 500 pM E2 and AP activity was measured as described in FIG. 2. Note that OP-1038 was statistically different from EM-343 and Gauthier compound Ia ($p<0.0001$ (exact p values stated in graph), calculated using Student's t-test). Results were from a single representative experiment and reported as the mean percent induction relative to E2 from triplicate treatments, with error bars representing SEM. B) Comparison of potency and efficacy of OP-1038 to Aragon Compound 28 in inhibiting E2-stimulated AP activity in ECC-1 cells. Results were from a single representative experiment and reported as the mean percent induction relative to E2 from triplicate treatments, with error bars representing SEM. IC50's were calculated using the least squares fit method. *Aragon Compound 28 was statistically different from equivalent dose of OP-1038 ($p\leq0.01$, calculated using Student's t-test). C) Detail of 100 nM dose in B indicating a statistical difference between Aragon Compound 28 at saturating dose.

Figure 7A:
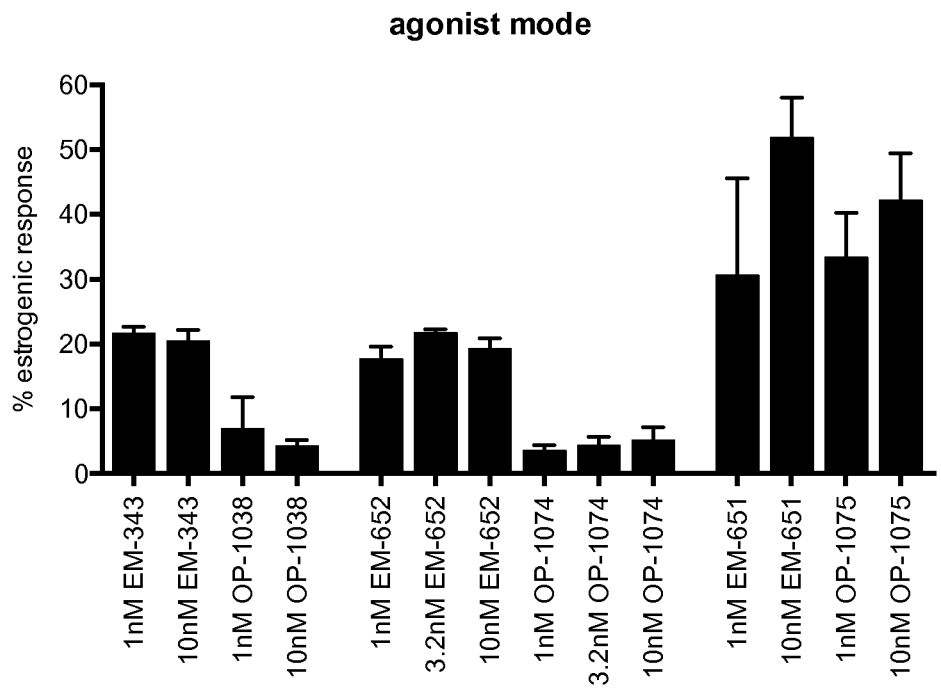
Figure 7B:
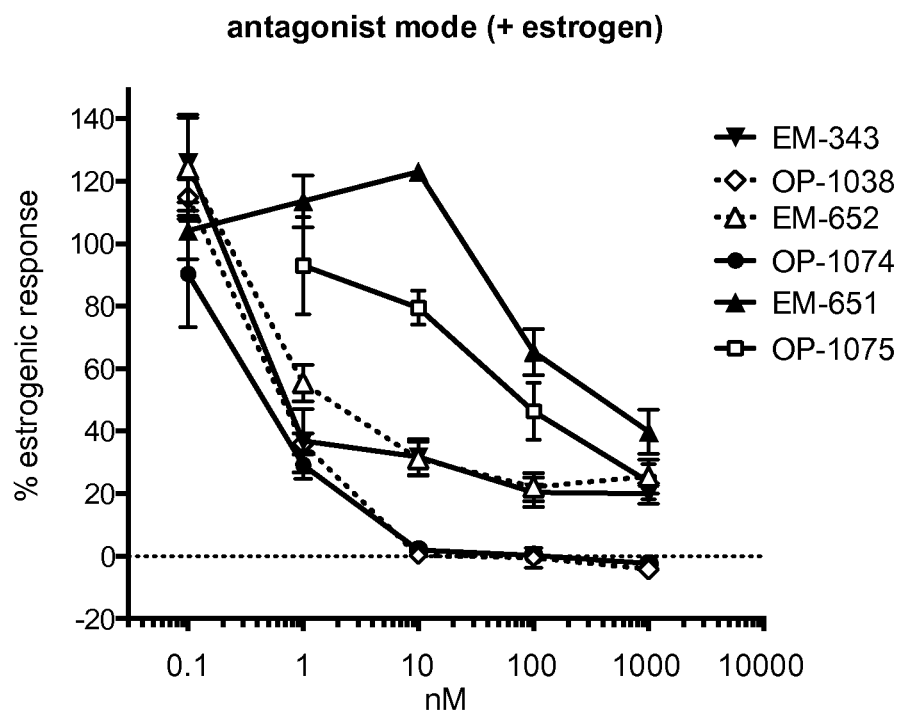
Figure 8A:
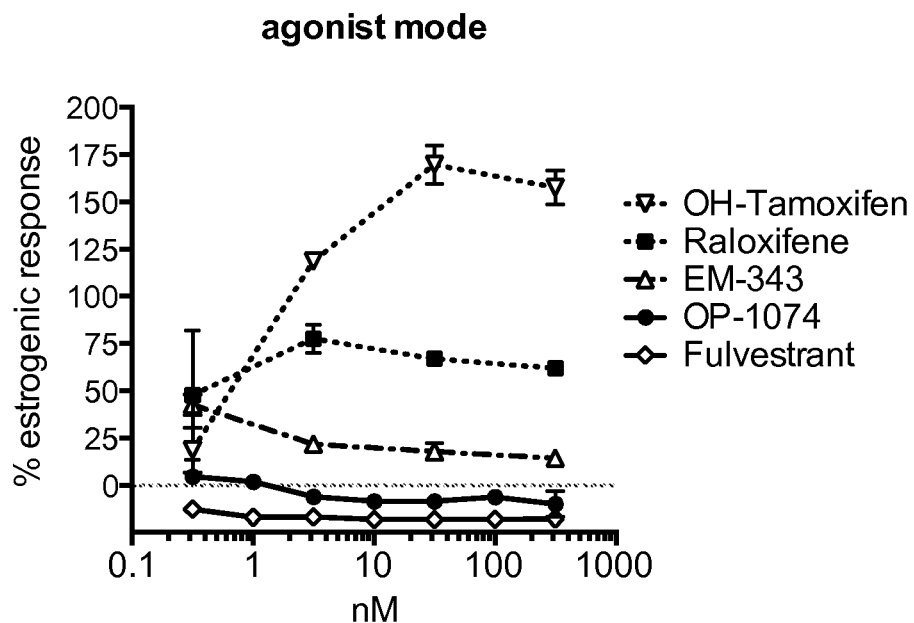
Figure 8B:
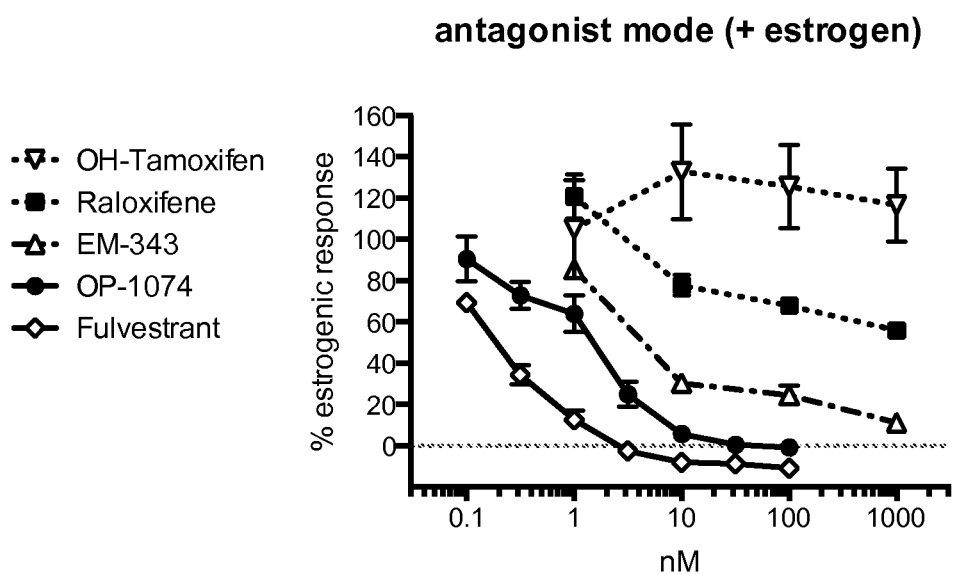
Figure 8C:
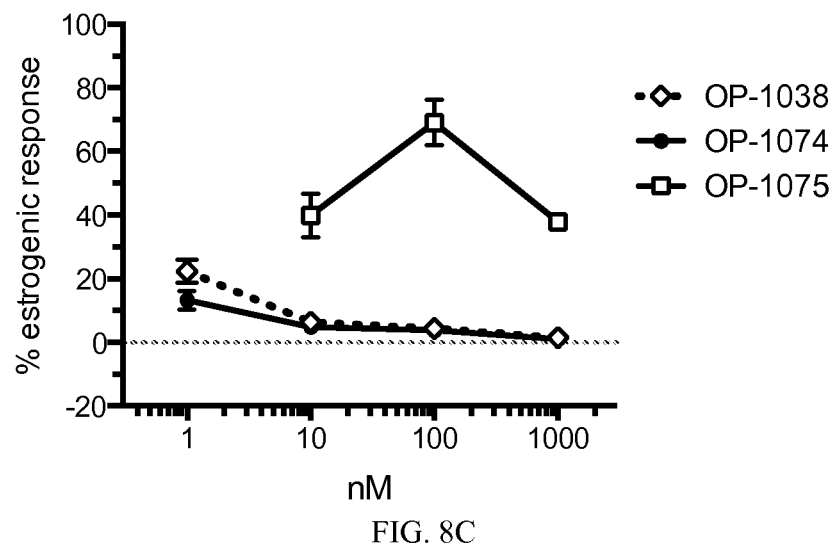
Figure 8D:
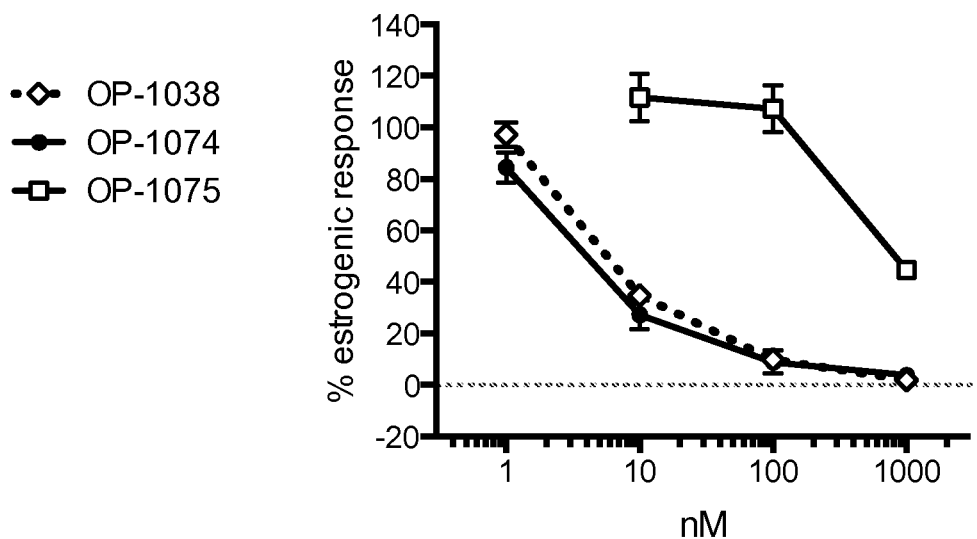

FIG. 7. Comparison of potency and efficacy of OP-1074 to EM-652 in the AP assay in ECC-1 cells. A) EM-343 and its active isomer EM-652 are more estrogenic than OP-1038 and OP-1074 in the AP assay. AP activity was measured as described in FIG. 2. Results were from a single representative experiment and reported as the mean percent induction relative to E2 from triplicate treatments, with error bars representing SEM. B) OP-1038 and OP-1074 are more anti-estrogenic than EM-343 and EM-652 in the presence of 500 pM E2. Results were from a single representative experiment and reported as the mean percent induction relative to E2 from triplicate treatments, with error bars representing SEM. IC50's were calculated using the least squares fit method.

FIG. 8. OP-1074 is a pure anti-estrogen in the agonist mode (without E2) and a complete anti-estrogen in the antagonist mode in the ECC-1 AP assay. A) and B) OP-1074, similar to fulvestrant, did not stimulate AP activity and inhibited E2-stimulated AP activity in a dose dependent manner. AP activity was measured as described in FIG. 2. Results were from a single representative experiment and reported as the mean percent induction relative to E2 from triplicate treatments, with error bars representing SEM. C) and D) OP-1074 was confirmed to be the active diastereomer of the equal mix of two diastereomers OP-1038, while the other diastereomer, OP-1075, had reduced activity. Results were from a single representative experiment and reported as the mean percent induction relative to E2 from triplicate treatments, with error bars representing SEM.

Figure 9:
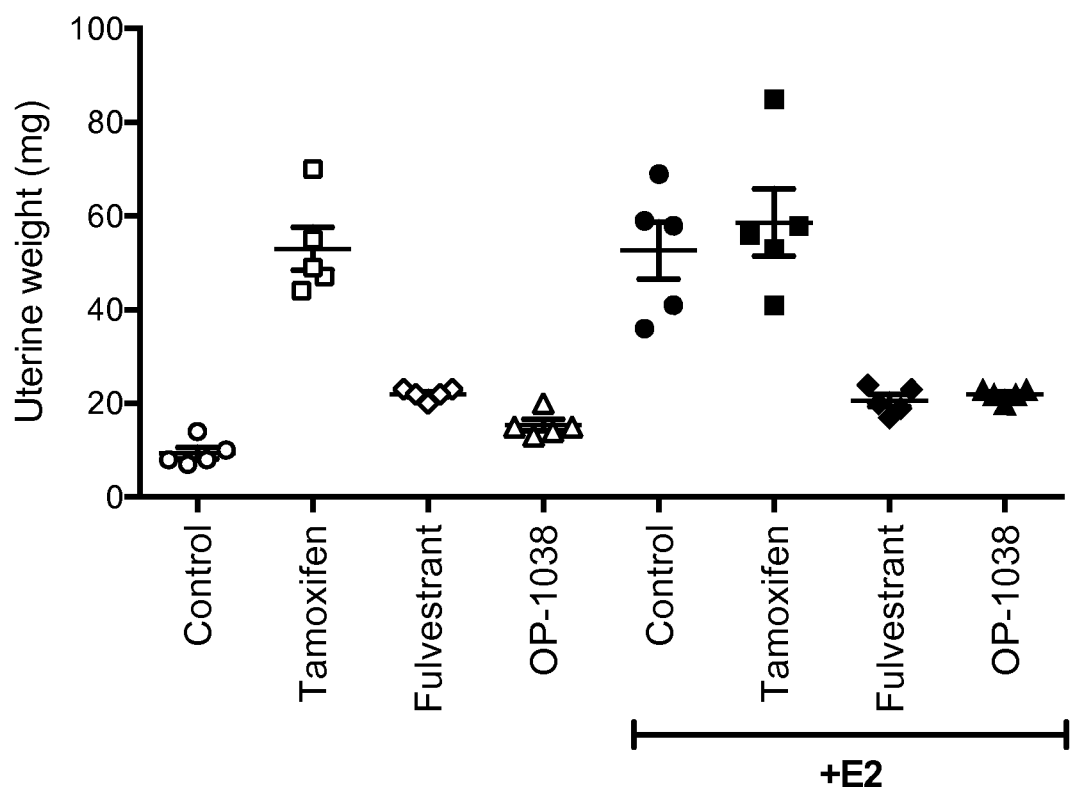

FIG. 9. OP-1074 is an essentially pure anti-estrogen when tested in the agonist mode and a complete anti-estrogen when tested in the in the antagonist mode on the mouse uterus. Uterine wet weight was measured at the end of three days after treating ovariectomized BALB/c mice q.d. with vehicle or one of the following treatments (10 mice per group): 50 mg/kg tamoxifen p.o. in 0.5% carboxymethylcellulose (CMC); 50 mg/kg fulvestrant sc in 5% ethanol; 100 mg/ml OP-1038 p.o. in 0.5% CMC. Half the animals in each group were co-treated with 0.1 µg/ml E2 sc in cottonseed oil-ethanol (95:5), or vehicle alone. Animal experiments were conducted at the University of California, San Francisco following institutional animal care and use committee protocols. OP-1038 was not significantly different from control or fulvestrant (determined by one way ANOVA at $p>0.05$) in the agonist mode. OP-1038 +E2 was not different from fulvestrant in the antagonist mode or from the control without E2.

Figure 10A:
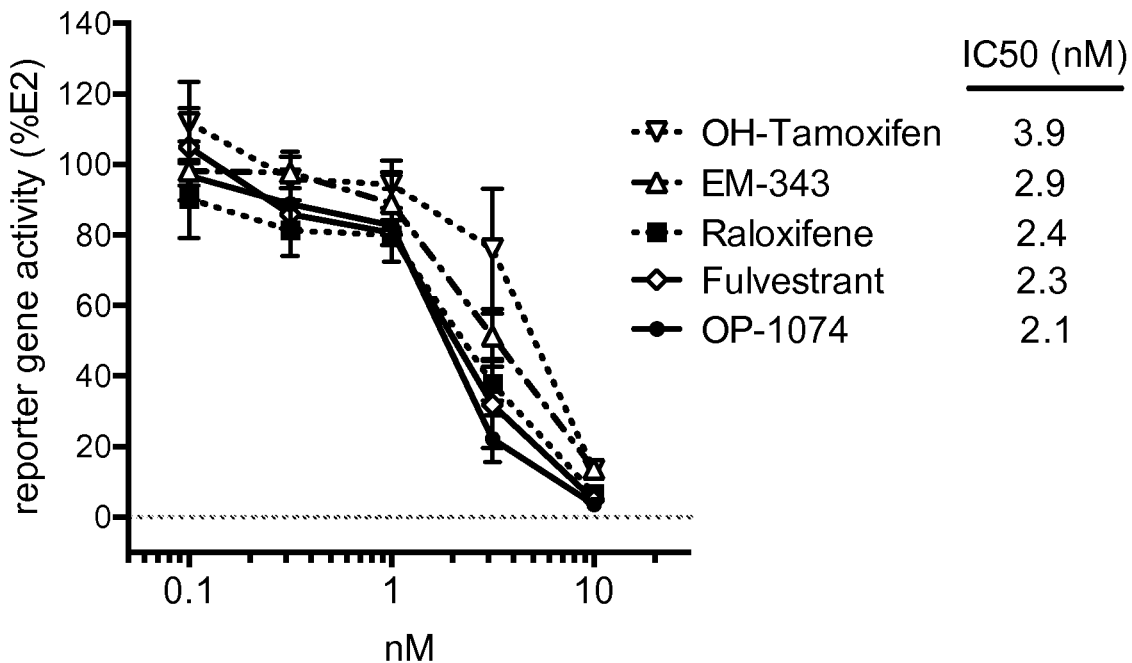
Figure 10B:
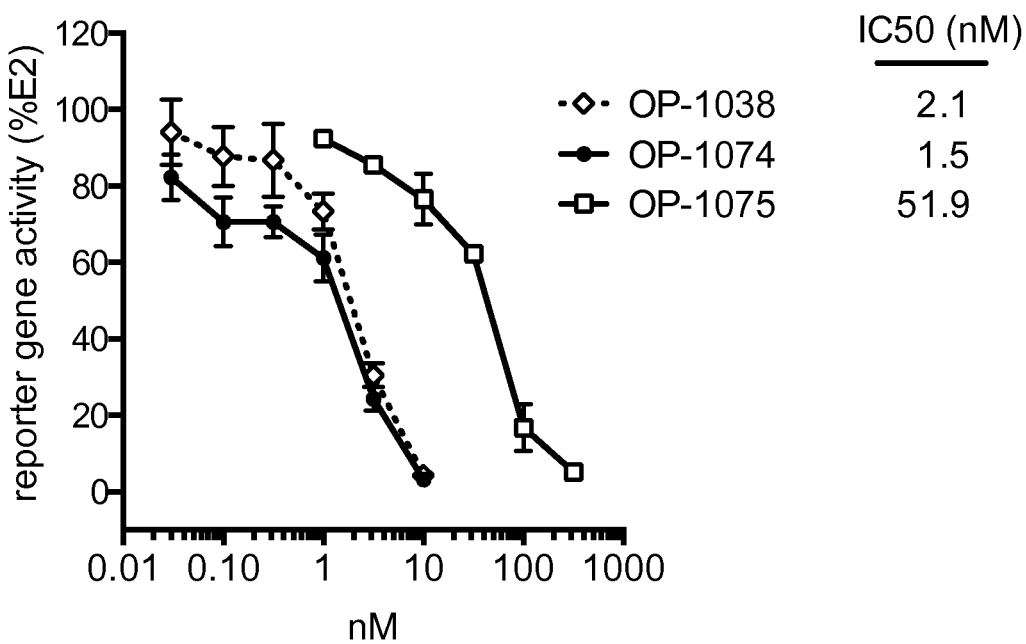

FIG. 10. OP-1038 and OP-1074 are potent antagonists of E2-stimulated estrogen response element (ERE)-regulated reporter gene activity. A) OP-1074 had similar potency to model anti-estrogens in the ERE reporter gene assay. MCF-7 cells were transiently transfected with ERE-tk109-Luc and treated with anti-estrogens in hormone-depleted medium in the presence of 100 pM E2 for 22 hours. Results were from a single representative experiment and reported as the mean percent induction relative to E2 from triplicate treatments, with error bars representing SEM. B) OP-1074 was confirmed to be the active diastereomer of the equal mix of two diastereomers OP-1038, while the other diastereomer, OP-1075, had reduced activity in the ERE reporter gene assay. Results were from a single representative experiment and reported as the mean percent induction relative to E2 from triplicate treatments, with error bars representing SEM. IC50's were calculated using the least squares fit method.

Figure 11A:
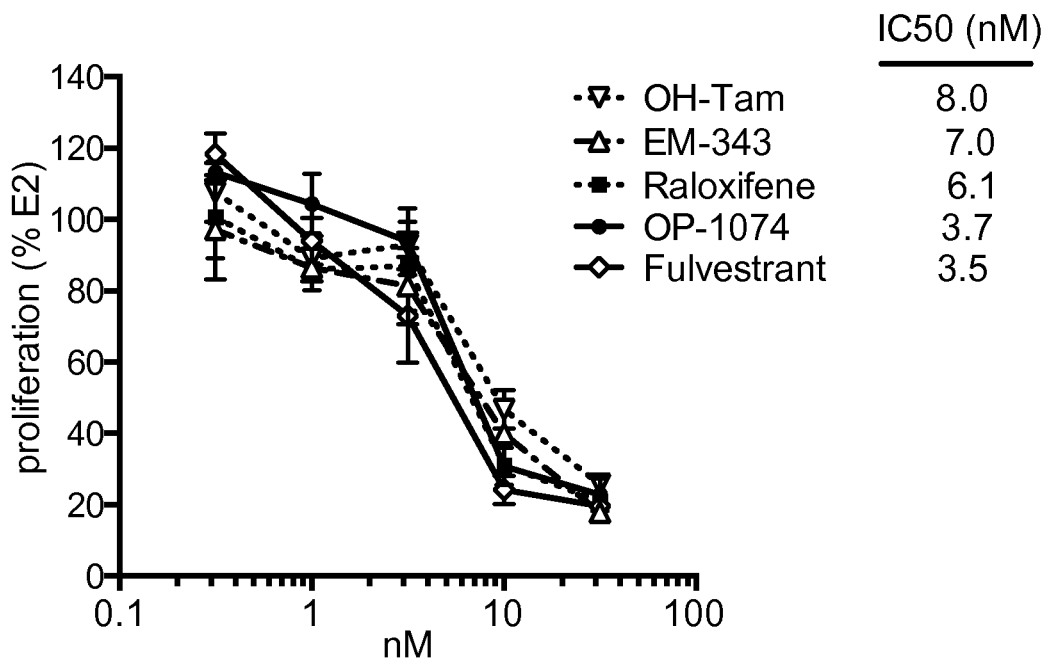
Figure 11B:
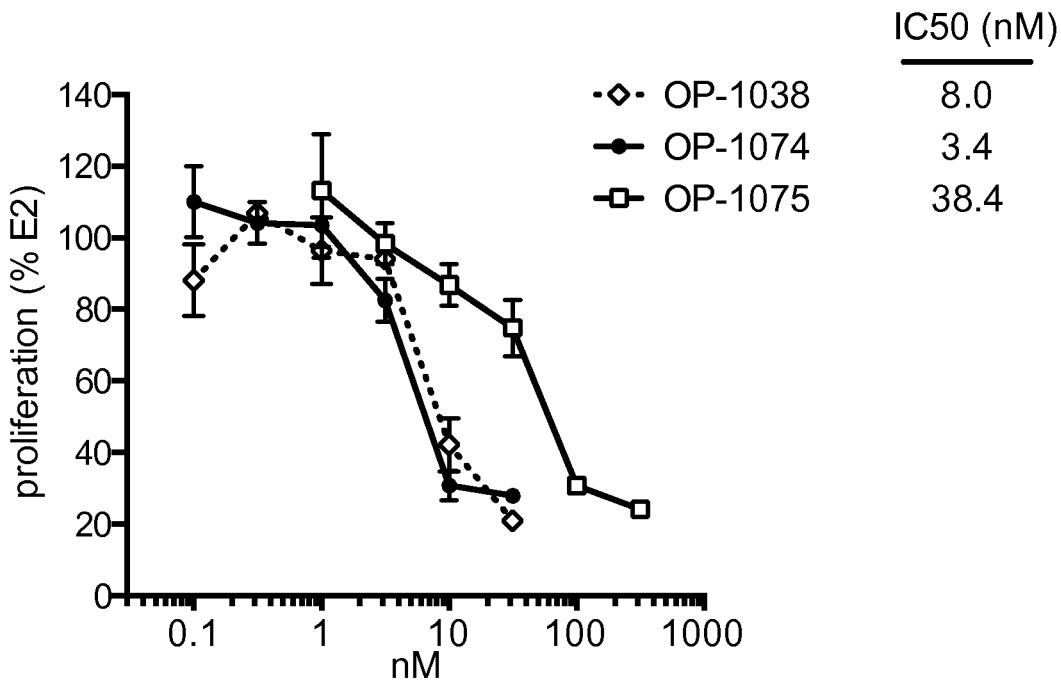

FIG. 11. OP-1038 and OP-1074 are potent antagonists of E2-stimulated proliferation in human MCF-7 breast cancer cells. A) OP-1074 had similar potency to model anti-estrogens in inhibiting E2-stimulated proliferation of breast cells in vitro. MCF-7 cells were treated with anti-estrogens in hormone-depleted medium for 6-8 days in the presence of 100 pM E2. Proliferation was measured using Cyquant fluorescent DNA-binding dye (Invitrogen, Grand Island, N.Y.). Results were from a single representative experiment and reported as the mean percent induction relative to E2 from triplicate treatments, with error bars representing SEM. B) OP-1074 was confirmed to be the active enantiomer of the diastereomer OP-1038, while the other diastereomer, OP-1075, had reduced activity in inhibiting E2-stimulated proliferation of breast cells in vitro. As shown, OP-1075 is more estrogenic than OP-1074. Results were from a single representative experiment and reported as the mean percent induction relative to E2 from triplicate treatments, with error bars representing SEM. IC50's were calculated using the least squares fit method.

Figure 12A:
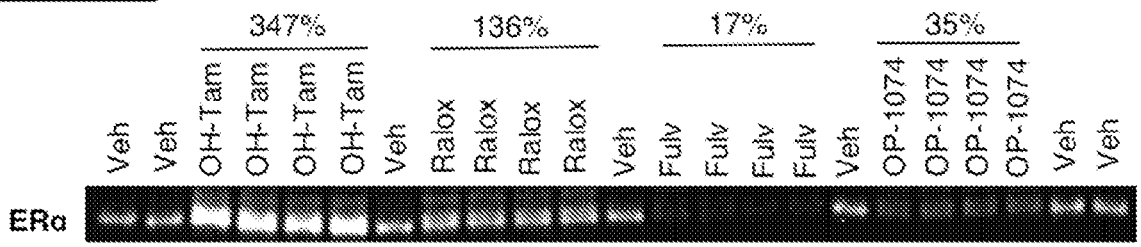
Figure 12B:
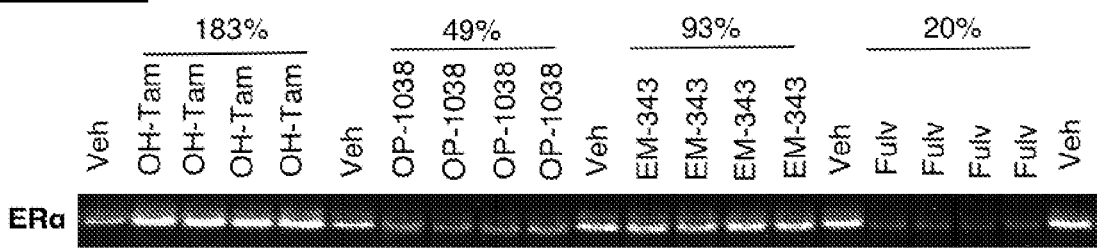
Figure 12B:
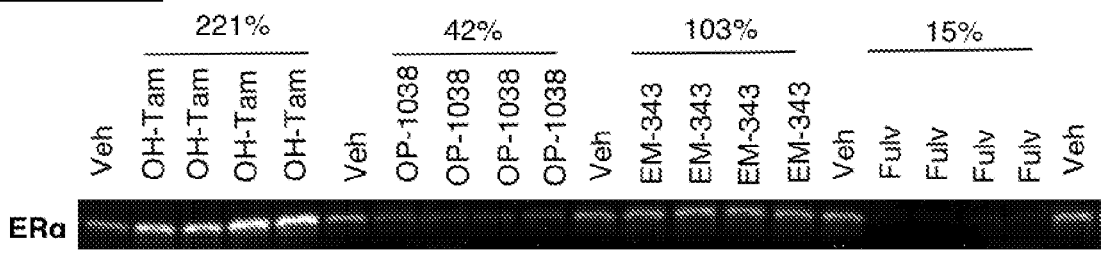

FIG. 12. OP-1074 and OP-1038 induce degradation of estrogen receptor alpha (ERα) in human breast and endometrial cells. A) ERα levels in breast cells after treatment with OP-1074 compared to treatment with model anti-estrogens. MCF-7 cells were treated with 100 nM anti-estrogen for 24 hours in serum-free medium and protein extracts immunoblotted with an antibody to ERα (D12, Santa Cruz Biotechnology, Santa Cruz, Calif.). Image is from a single representative experiment and number on top denotes the mean percent ERα expression relative to vehicle from quadruplicate treatments. B) OP-1038 induces degradation of ERα in both MCF-7 breast cells and ECC-1 endometrial cells.

FIG. 13. OP-1074 induces rapid and complete regression of MCF-7 clone 18 HER2/neu xenografts stimulated by estrogen. A) Percent change in tumor volume of human MCF-7 HER2/neu clone 18 xenografts in ovariectomized athymic nude mice implanted with estrogen pellets and treated with either tamoxifen (by oral gavage), fulvestrant (Faslodex) by s.c. injection, or OP-1074 (by oral gavage). B) Weights of the animals treated as above. C) Waterfall plot of final tumor volumes compared with volumes at the start of treatment.

DETAILED DESCRIPTION OF THE INVENTION

The present invention is based on the discovery that a specific benzopyran (in the form of a C2 equal mix of diastereomers OP-1038 and its pure S-diastereomer OP-1074) has unexpectedly improved properties for the treatment of medical disorders that are mediated, modulated or affected by an estrogen receptor, including breast cancer.

The compound can be provided if desired as a pharmaceutically acceptable salt, solvate, hydrate, prodrug, stereoisomer, tautomer, N-oxide or $R^1$ and/or $R^2$-substituted derivative or a pharmaceutically acceptable composition thereof to treat a disorder that is mediated, modulated or affected by an estrogen receptor, including those treatable with an anti-estrogenic compound with virtually no estrogenic effect.

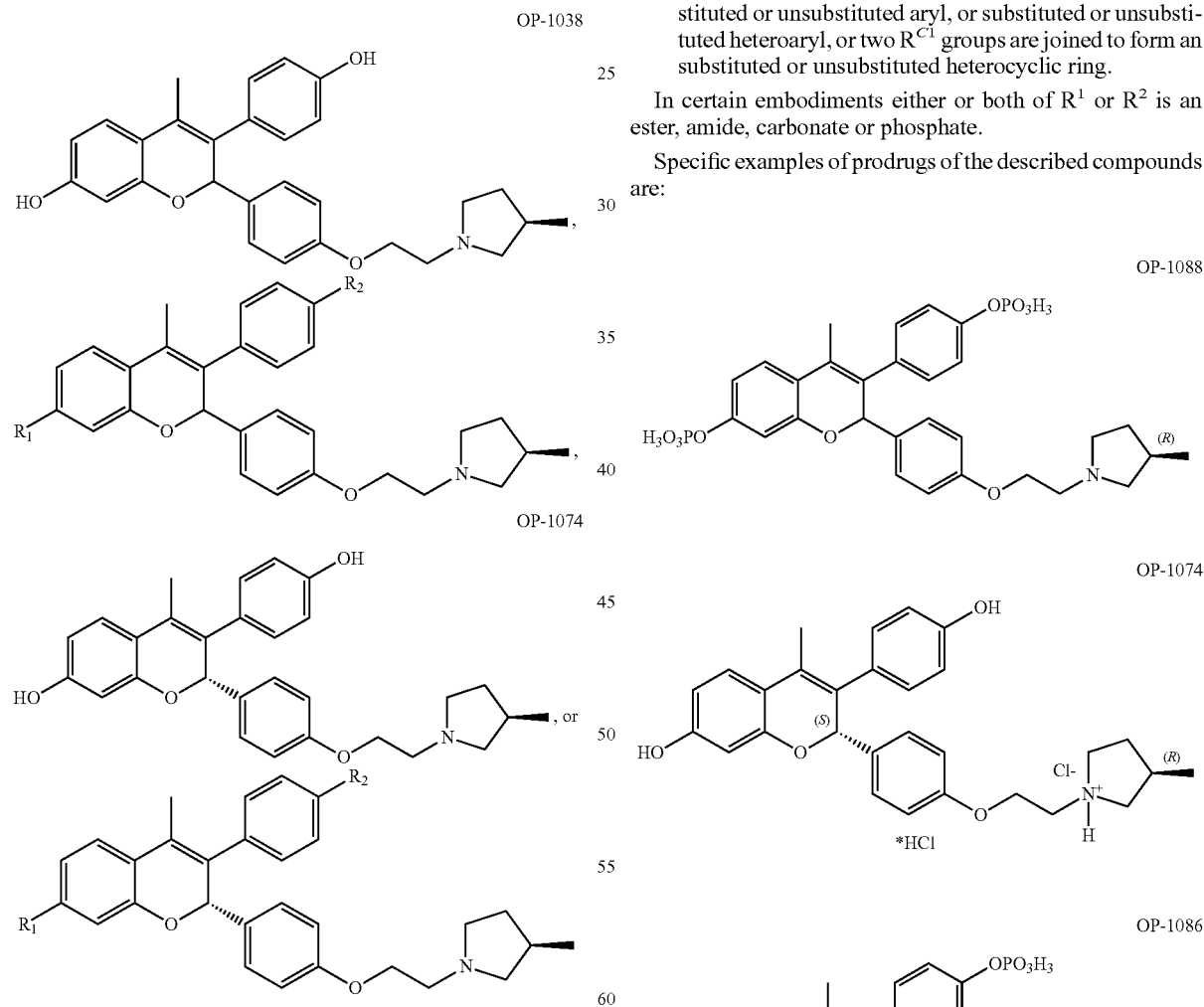

wherein $R^1$ and $R^2$ are independently either:
(i) $R^9$ which is independently selected from H, halogen (Cl, Br, I or F), natural or non-naturally occurring amino acid (bound through either the OC(O)— or C(O)O— (an ester) or the amino (through either —C(O)—N— or —N—C(O)— (an amide linkage)), $R^{10}$, —$OR^{10}$, or —$SR^{10}$ where $R^{10}$ is —C(O)$R^{C1}$, —C(=O)O$R^{C1}$, —C(=O)S$R^{C1}$, —C(=O)N($R^{C1}$)$_2$; or polyethylene glycol, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; —S(=O)$_2R^{C1}$, —S(=O)$_2$O$R^{C1}$, —S(=O)$R^{C1}$, —S(=O)O$R^{C1}$, —P(=O)$_2R^{C1}$, —P(=O)$_2$O$R^{C1}$, —P(=O)(O$R^{C1}$)$_2$, —P(=O)($R^{C1}$)$_2$, or —P($R^{C1}$)(O$R^{C1}$); or oxygen attached to an oxygen protecting group (to produce OH on administration), sulfur attached to a sulfur protecting group (to produce SH or a disulfide on administration), or nitrogen attached to a nitrogen protecting group (to produce —NH— on administration);

and $R^{c1}$ can be independently selected from hydrogen, polyethylene glycol, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{C1}$ groups are joined to form an substituted or unsubstituted heterocyclic ring.

In certain embodiments either or both of $R^1$ or $R^2$ is an ester, amide, carbonate or phosphate.

Specific examples of prodrugs of the described compounds are:

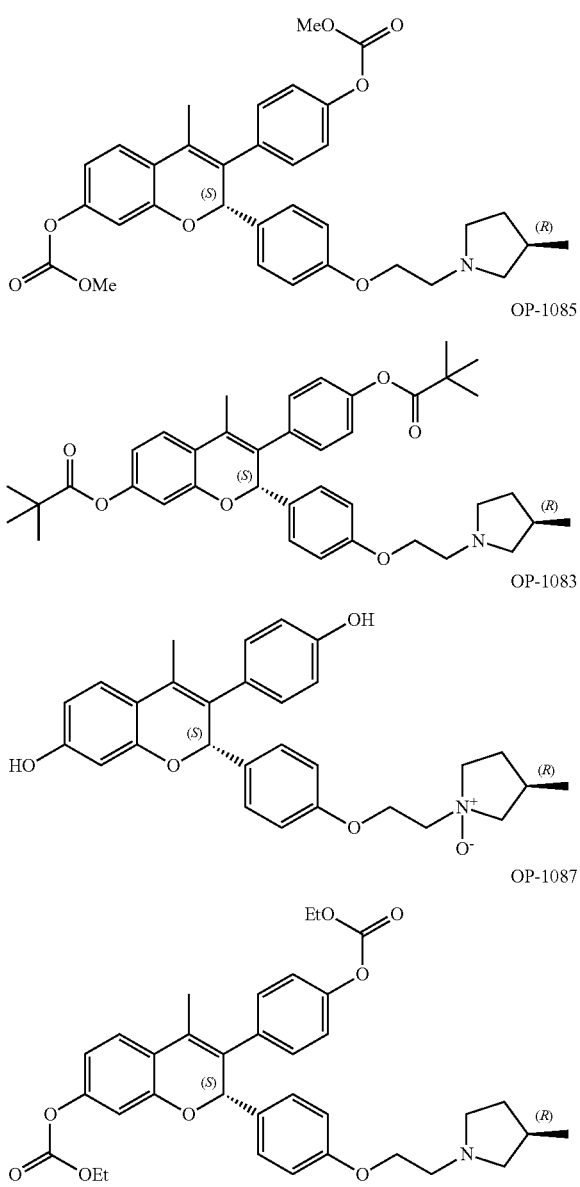

Examples of useful metabolically cleavable prodrug groups include acetyl, methoxycarbonyl, benzoyl, methoxymethyl and trimethylsilyl groups The compounds of the invention can be administered in a pharmaceutical composition suitable for oral delivery to the patient, typically a human. Alternatively, the compounds can be delivered in a carrier suitable for topical, transdermal (including by patch), intravenous, parenteral, intraortal, subcutaneous or other desired delivery route, including any method of controlled delivery, for example, using degradable polymers, or with nano or microparticles, liposomes, layered tablets or other structural frameworks which slow delivery.

In yet another aspect, the compounds of the invention can be used to prevent a disorder modulated through the estrogen receptor, which comprises administering to a patient in need of such prevention, a prophylactically effective amount of a compound or pharmaceutical composition.

The compounds of the invention can be in the form of a salt. They can be administered as a pharmaceutically acceptable salt, for example, a pharmaceutically acceptable acid addition salt, including a hydrochloride, hydroiodide, hydrobromide, nitrate, sulfate, bisulfate, phosphate, acetate, lactate, citrate, tartrate, succinate, maleate, fumarate, benzoate, para-toluenesulfonate and the like.

The compounds are used to treat or prevent a disorder modulated by the estrogen receptor in an animal, typically a mammal, and most typically a human.

In yet another aspect, the present invention provides a combination of a compound of the instant invention, and another pharmacologically active agent.

The compounds can also be used as adjunctive therapy or combination therapy with another active agent. For example, a therapeutically effective amount of the compound can be used in combination with another anti-cancer agent, especially for estrogen receptor positive breast cancer, but in some embodiments, for estrogen receptor negative breast cancer.

Additional embodiments within the scope provided herein are set forth in non-limiting fashion elsewhere herein and in the examples. It should be understood that these examples are for illustrative purposes only and are not to be construed as limiting in any manner.

Pharmaceutical Compositions

In one aspect, the invention provides a pharmaceutical composition comprising a pharmaceutically effective amount of a compound of the present invention and a pharmaceutically acceptable carrier.

The compounds provided herein are administered for medical therapy in a therapeutically effective amount. The amount of the compound administered will typically be determined by a physician, in the light of the relevant circumstances, including the condition to be treated, the chosen route of administration, the compound administered, the age, weight, and response of the individual patient, the severity of the patient's symptoms, and the like.

The pharmaceutical compositions provided herein can be administered by a variety of routes including oral, topical, parenteral, rectal, transdermal, subcutaneous, intravenous, intramuscular, and intranasal with a pharmaceutical carrier suitable for such administration. In one embodiment, the compound is administered in a controlled release formulation.

The compositions for oral administration can take the form of bulk liquid solutions or suspensions, or bulk powders. Typically, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (as a nonlimiting example, from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art.

Transdermal compositions are typically formulated as a topical ointment or cream containing the active ingredient(s), for example in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a suitable delivery polymeric composition, or a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can be administered by a transdermal device. Transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical *Sciences*, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences*.

In certain embodiments, the formulation comprises water. In another embodiment, the formulation comprises a cyclodextrin derivative. In certain embodiments, the formulation comprises hexapropyl-β-cyclodextrin. In a more particular embodiment, the formulation comprises hexapropyl-β-cyclodextrin (10-50% in water).

The present invention also includes pharmaceutically acceptable acid addition salts of compounds of the compounds of the invention. The acids which are used to prepare the pharmaceutically acceptable salts are those which form non-toxic acid addition salts, i.e. salts containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate non-limiting representative pharmaceutical compositions that may be prepared in accordance with this invention for the purpose of illustration only. The present invention is specifically not limited to the following pharmaceutical compositions.

Formulation 1

Tablets

A compound of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2

Capsules

A compound of the invention may be admixed as a dry powder with a starch diluent in an approximate 1:1 weight ratio. The mixture is filled into 250 mg capsules (125 mg of active compound per capsule).

Formulation 3

Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4

Tablets

A compound of the invention can be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press. In other embodiments, there is between 10 and 500 mg of active compound in the oral tablet.

Formulation 5

Injection

A compound of the invention can be dissolved or suspended in a buffered sterile saline injectable aqueous medium to a concentration of approximately 5, or 10, or 15, or 20, or 30 or 50 mg/mL.

Formulation 6

Tablets

A compound of the invention may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Formulation 7

Tablets

A compound of the invention may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Formulation 8

Tablets

A compound of the invention may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Formulation 9

Tablets

A compound of the invention may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Formulation 10

Tablets

A compound of the invention may be admixed as a dry powder with a dry gelatin binder in an approximate 1:2 weight ratio. A minor amount of magnesium stearate is added as a lubricant. The mixture is formed into tablets (5-1000 mg of active compound per tablet) in a tablet press.

Use of Compounds in Medical Therapy

OP-1038, OP-1074 and their prodrugs (including esters, carbonates and phosphates), derivatives and their salts as described herein are complete anti-estrogens useful to treat any disorder modulated, mediated or affected by the estrogen receptor.

In one embodiment, the compound is used in combination or alternation with another anti-cancer agent for the treatment of cancer, as described more fully below. In another embodiment, the compound in combination or alternation with estrogen or a partial estrogen receptor angatonist for the treatment of a postmenopausal disorder, also described below.

In one embodiment, local, a compound of the present invention is use to treat local, advanced or metastatic breast cancer that is positive for expression of estrogen receptors, progesterone receptors or both (receptor positive advanced breast cancer). In an alternative embodiment, the compound is used to treat estrogen or progesterone receptor negative breast cancer. The compound can be used as the initial treatment of advanced breast cancer in patients who have never received previous hormonal therapy for advanced breast cancer, either by itself or in combination with one or more other anti-cancer agents described below or otherwise known to those skilled in the art. They are also useful for second line therapy for treatment after a previous hormonal therapy has failed, either by itself or in combination with another anticancer agent, for example, a targeted therapy such as an mTOR inhibitor such as everolimus.

The compounds of the invention are also useful as adjunctive therapy after or instead of chemotherapy, radiation or surgery. Such adjuvant use is often used for several years, perhaps 5 years, after chemotherapy or other therapies have been concluded, but may optimally be continued for additional years.

The compounds of the invention are also useful for the prevention of breast cancer in women at high risk and can be taken for any desired time period, including indefinitely. For example, a patient, typically a woman, with a family history of breast cancer, or who has been determined to carry a mutation in the BRACA1 or BRACA2 gene gene or other genes that predispose a patient to breast cancer may choose to use such preventative treatment instead of a mastectomy or other intervention. The compounds described herein are also useful as neoadjuvants to shrink large tumors prior to surgical removal, both to enable breast conservative surgery and to reduce the risk of recurrence. In addition to breast cancer these compounds also are useful in treating other cancers and other overgrowth diseases of the female reproductive tract including ovarian, endometrial, and vaginal cancer and endometriosis. Besides these reproductive tissues the compounds are useful in treating lung cancers that are positive for estrogen or progesterone receptors.

Selective estrogen receptor modulators (SERMS) are useful for hormonal therapy for postmenopausal women in particular to treat or prevent osteoporosis. In one embodiment, a compound of the present invention is used in combination with an estrogen, SERM or partial anti-estrogen whereby the complete anti-estrogen prevents adverse action of the total or partial estrogen on the uterus and other tissues.

The present compounds are used as therapeutic or prophylactic agents for the treatment of conditions in mammals, particularly humans that are modulated by estrogen receptors.

An oral complete anti-estrogen is useful for treating locally advanced or metastatic breast cancer, preventing recurrence or early breast cancer after surgery, and preventing breast cancer in women at high risk. It is useful for treating all estrogen-dependent cancers of the reproductive tract including endometrial and ovarian cancers. It has potential uses in the treatment of lung and bronchial cancers that express estrogen receptors. Selective estrogen receptor modulators (SERMS) such as tamoxifen, raloxifene, lasofoxifene, and bazedoxifene additionally have application as hormone replacement therapy to prevent osteoporosis and other disorders such as hot flashes, etc. in post-menopausal women, a use that depends on their partial estrogen like action, for example, on bone. The compounds described herein can be employed in combination with an estrogen or a selective estrogen receptor modulator to block the unwanted estrogenic activity of the therapy. The complete anti-estrogen is dosed in the amount to prevent the adverse action of the estrogen or estrogen receptor modulator on the uterus and mammary gland yet allowing the beneficial action of estrogen on bone and vasomotor symptoms.

The compounds of the present invention can be administered for the treatment of cancer, and in particular breast cancer in combination or association with Herceptin, Tykerb, CDK4/6 inhibitor such as PD-0332991, mTOR inhibitor such as Novartis' everolimus and other rapamycin analogs such as rapamycin and temsirolimus, Millennium's MLN0128 TORC1/2 inhibitor, an EFGR-family inhibitor such as trastuzumab, pertuzumab, trastuzumab, emtansine, erlotinib, gefitinib, neratinib and similar compounds, a PI3 Kinase Inhibitor such as perifosene, CAL101, BEZ235, XL147, XL765, GDC-0941, and IPI-145, a histone deacetylase inhibitor such as vorinostat, romidepsin, panobinostat, valproic acid, etinostat, and belinostat.

In another method of treatment aspect, provided herein is a method of treating a mammal susceptible to or afflicted with a condition related to estrogen receptor.

In another embodiment, the compounds of the present invention are provided for use in medical therapy, including for any of the conditions described herein. The use of the present compounds in the manufacture of a medicament for the treatment or prevention of one of the aforementioned conditions and diseases is also provided.

Injection dose levels range are provided in any desired dosage, for example, from about 0.1 mg/kg/hour to at least 10 mg/kg/hour, all for from about 1 to about 120 hours and especially 24 to 96 hours. In one embodiment, a preloading bolus of from about 0.1 mg/kg to about 10 mg/kg or more may also be administered to achieve adequate steady state levels. The maximum total dose is not expected to exceed about 2 g/day for a 40 to 80 kg human patient.

For oral dosing, any dose is appropriate that achieved the desired goals. In one example, suitable daily dosages are between about 0.1-4000 mg, more typically between 5 mg and 1 gram, more typically between 10 mg and 500 mg, and administered orally once-daily, twice-daily or three times-daily, continuous (every day) or intermittently (e.g., 3-5 days a week). For example, when used to treat any disorder described herein, the dose of the compounds of this invention usually ranges between about 0.1 mg, more usually 10, 50, 100, 200, 250, 1000 or up to about 2000 mg per day.

For the prevention and/or treatment of long-term conditions, such as neurodegenerative and autoimmune conditions, the regimen for treatment usually stretches over many months or years. Oral dosing may be preferred for patient convenience and tolerance. With oral dosing, one to five and especially two to four and typically three oral doses per day are representative regimens. Using these dosing patterns, non-limiting dosages might range from about 0.01 to about 20 mg/kg of the compound provided herein, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of cancer, a neurodegenerative, autoimmune or inflammatory condition, the compounds provided herein will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds provided herein can be administered as the sole active agent or they can be administered in combination with other agents. Administration in combination can proceed by any technique apparent to those of skill in the art including, for example, separate, sequential, concurrent and alternating administration.

General Synthetic Procedures

The compounds provided herein can be prepared from readily available starting materials using the following general methods and procedures. See, e.g., Synthetic Schemes below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography or HPLC. The following schemes are presented with details as to the preparation of representative substituted benzopyrans that have been listed herein. The compounds provided herein may be prepared from known or commercially available starting materials and reagents by one skilled in the art of organic synthesis.

The diastereomerically or enantiomerically pure compounds provided herein may be prepared according to any techniques known to those of skill in the art. For instance, they may be prepared by chiral or asymmetric synthesis from a suitable optically pure precursor or obtained from a racemate or mixture of diastereomers by any conventional technique, for example, by chromatographic resolution using a chiral column, TLC or by the preparation of diastereoisomers, separation thereof and regeneration of the desired enantiomer or diastereomer. See, e.g., "Enantiomers, Racemates and Resolutions," by J. Jacques, A. Collet, and S. H. Wilen, (Wiley-Interscience, New York, 1981); S. H. Wilen, A. Collet, and J. Jacques, *Tetrahedron*, 2725 (1977); E. L. Eliel *Stereochemistry of Carbon Compounds* (McGraw-Hill, N.Y., 1962); and S. H. Wilen *Tables of Resolving Agents and Optical Resolutions* 268 (E. L. Eliel ed., Univ. of Notre Dame Press, Notre Dame, Ind., 1972, *Stereochemistry of Organic Compounds*, Ernest L. Eliel, Samuel H. Wilen and Lewis N. Manda (1994 John Wiley & Sons, Inc.), and *Stereoselective Synthesis A Practical Approach*, Mihaly Nogradi (1995 VCH Publishers, Inc., NY, N.Y.).

In certain embodiments, a diastereomerically pure compound of formula (I) may be obtained by reaction of the racemate or mix of diastereomers with a suitable optically active acid or base. Suitable acids or bases include those described in Bighley et al., 1995, *Salt Forms of Drugs and Adsorption*, in *Encyclopedia of Pharmaceutical Technology*, vol. 13, Swarbrick & Boylan, eds., Marcel Dekker, New York; ten Hoeve & H. Wynberg, 1985, *Journal of Organic Chemistry* 50:4508-4514; Dale & Mosher, 1973, *J. Am. Chem. Soc.* 95:512; and *CRC Handbook of Optical Resolution via Diastereomeric Salt Formation*, the contents of which are hereby incorporated by reference in their entireties.

Enantiomerically or diastereomerically pure compounds can also be recovered either from the crystallized diastereomer or from the mother liquor, depending on the solubility properties of the particular acid resolving agent employed and the particular acid enantiomer or diastereomer used. The identity and optical purity of the particular compound so recovered can be determined by polarimetry or other analytical methods known in the art. The diasteroisomers can then be separated, for example, by chromatography or fractional crystallization, and the desired enantiomer or diastereomer regenerated by treatment with an appropriate base or acid.

The other enantiomer or diasteromer may be obtained from the racemate or mix of diastereomers in a similar manner or worked up from the liquors of the first separation.

In certain embodiments, enantiomerically or diastereomerically pure compound can be separated from racemic compound or a mixture of diastereomers by chiral chromatography. Various chiral columns and eluents for use in the separation of the enantiomers or diastereomers are available and suitable conditions for the separation can be empirically determined by methods known to one of skill in the art. Exemplary chiral columns available for use in the separation of the enantiomers provided herein include, but are not limited to CHIRALPACK® IC, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

General processes for preparing compounds of the instant invention are provided as further embodiments of the invention and are illustrated in the following Schemes.

Synthesis of Intermediates

The various intermediates useful for preparation of the compounds of the invention can be prepared in accordance with methods described in the art and using the appropriate reagents, starting materials, and purification methods known to those skilled in the art.

Representative Intermediate Synthesis 1

Representative Synthesis of 4-(2-(methylpyrrolidin-1-yl)ethyl)benzaldehyde analogs

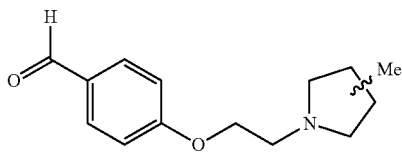

The intermediate methylpyrrolidine derivatives can be prepared by following the representative method described below.

R)-1,4-Dibromo-2-methylbutane (2'

To a solution of R-2-methylbutane-1,4-diol (1') (5 g, 48 mmol) in pyridine (5 mL) at 0° C. is added PBr$_3$ (9 g, 33 mmol) and the resulting yellow paste is stirred at room temperature for 30 minutes. The reaction mixture is heated at 100° C. for two hours. The cooled mixture is treated with water (50 mL) and extracted with hexanes (3×50 mL). The combined organic extracts are washed with 5% sodium hydroxide, concentrated sulfuric acid and water and concentrated to yield a yellow oily residue. This residue is distilled at 75-85° C. (3 mm Hg) to yield 2' as a clear colorless oil (4.5 g 42% yield).

R)-2-(3-Methylpyrrolidin-1-yl)ethanol (4'

To a solution of 2' (4.5 g, 19 mmol) in acetonitrile (200 mL) and potassium carbonate (5.5 g, 30.5 mmol) is added ethanolamine (1.2 mL, 19 mmol) and the resulting suspension is heated at reflux for 48 hours. The cooled solution is filtered and concentrated. This residue is dissolved in DCM (100 mL) and washed with 5% aqueous sodium hydroxide (2×50 mL), brine, dried over anhydrous sodium sulfate, filtered, and concentrated to yield a pale yellow oil. This oil is distilled (100-110, 3 mm Hg) to yield 4 as a clear colorless oil (1.4 g, 30% yield).

R)-4-(2-(3-Methylpyrrolidin-1-yl)ethoxy)benzaldehyde (6' a

To a solution of 4' (1.4 g, 10.9 mmol), p-hydroxybenzaldehyde, 5', (2.0 g, 16.3 mmol) and triphenylphosphine (4.3 g, 16.3 mmol) in dichloromethane (20 mL) is added diisopropylazodicarboxylate (2.3 mL, 16.3 mmol) dropwise at 0° C. over 30 minutes and then allowed to warm to room temperature and stirred for an additional two hours. The solution is washed with water, brine, dried over anhydrous sodium sulfate, filtered, and concentrated to yield a pale yellow oil. This oil is purified by silica gel column chromatography using a gradient of 0 to 5% methanol in dichloromethane to yield 6' a as a clear colorless oil (1.0 g, 39% yield).

MS Calculated $C_{14}H_{19}NO_2+H^+$=235; Observed 234.

The following intermediates are or can be prepared following the method described for 6'a and using the appropriate reagents, and starting materials.

Scheme 1

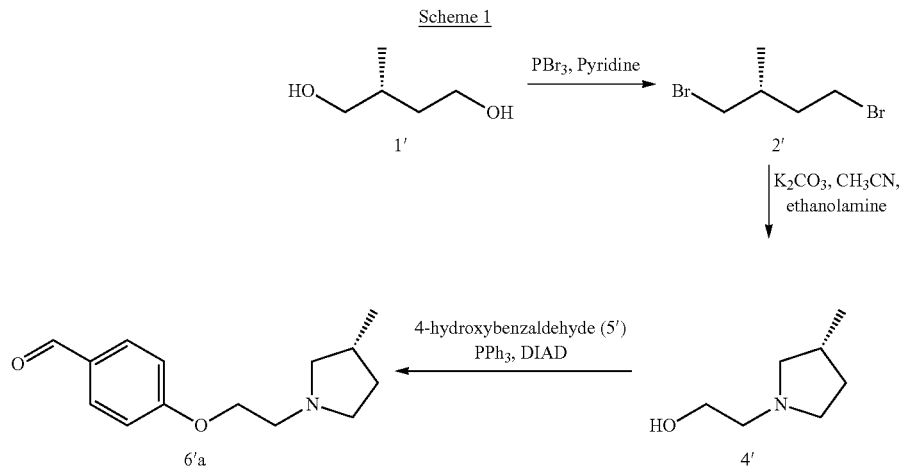

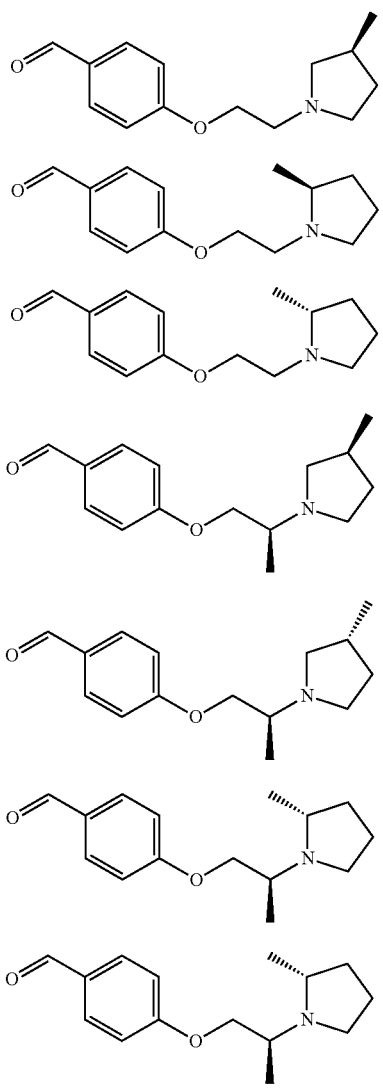

Representative Intermediate Synthesis 2

Representative Synthesis of
1-((2-Chloro-1-methyl)ethyl)-3-alkyl pyrrolidine
analogs

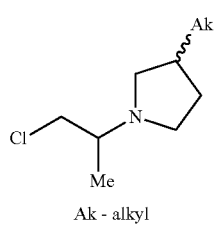

Ak - alkyl

The intermediate chloroethylalkylpyrrolidine derivatives can be prepared by following the representative method described in *Bioorganic & Medicinal Chemistry Letters* (2005) 15 3912-3916.

The synthesis of a representative pyrrolidine derivative, (R)-1-((S)-2-chloro-1-methyl-ethyl)-3-methyl-pyrrolidine is given below.

Intermediate A

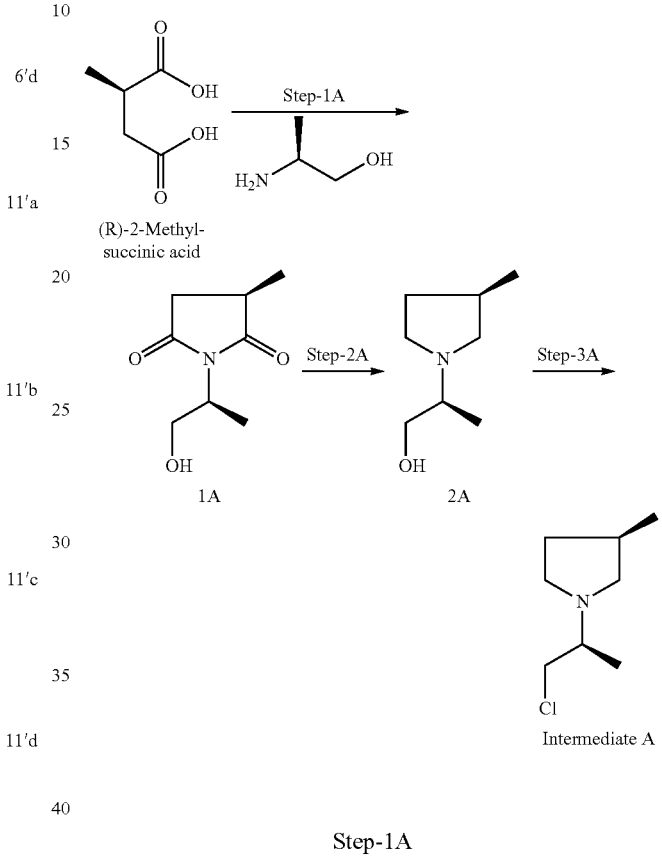

Intermediate A

Step-1A

A solution of (R)-2-methyl succinic acid (1 g, 7.57 mmol) in 40 mL of toluene was heated at 100° C. and (S)-2-Amino-propan-1-ol (0.59 mL, 7.57 mmol) was added slowly to the reaction mixture. After the completion of addition, the reaction mixture was further heated at 130° C. for 16 h. The reaction mixture was cooled to room temperature, concentrated under vacuum to get the crude product, which was purified by chiral preparative HPLC to get pure 1A. Yield: 0.6 g, 46%.

Step-2A

A solution of Intermediate 1A (0.5 g, 2.92 mmol) in dry ether (10 mL) was added in drops to a cooled suspension of LAH (0.433 g, 11.7 mmol) in dry diethyl ether at 0° C. After completion of addition, the reaction mixture was gradually allowed to reach room temperature and stirred for 12 h. The reaction was monitored by TLC (20% MeOH in DCM). After completion of reaction, the reaction mixture was cooled to 0° C., quenched successively with water (0.5 mL), 10% NaOH (1 mL) and water (1.5 mL). The solid precipitated was filtered through celite and the filtrate was concentrated under vacuum to get the product which was used as such for next step. Yield: 290 mg, 70%.

Step-3A

To a solution of Intermediate 2A (0.3 g, 2.1 mmol) in 1,2 dichloroethane (10 mL), thionyl chloride (0.18 mL, 2.5 mmol) was added drop wise at 0° C. Then the reaction mixture was gradually heated to 80° C. for 2 h. The excess solvent and thionyl chloride was concentrated under reduced pressure to get the crude Intermediate A, which was taken as such for next step (product formation was confirmed by LCMS). Yield: 300 mg, 88%.

Intermediate B

The synthesis of a representative pyrrolidine derivative, (R)-1-((R)-2-chloro-1-methyl-ethyl)-3-methyl-pyrrolidine (Intermediate B) is given below (*Bioorganic & Medicinal Chemistry Letters* 15 (2005) 3912-3916).

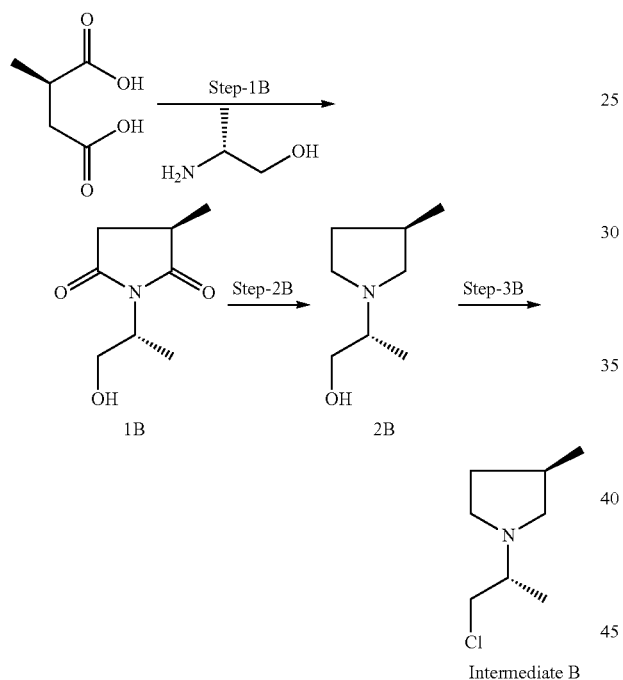

Scheme 3 / Intermediate B

Step-1B

A solution of (R)-2-methyl succinic acid (1 g, 7.5 mmol) in 40 mL of toluene was heated at 100° C. and (R)-2-aminopropan-1-ol (0.59 ml, 7.5 mmol) was added slowly to the reaction mixture. After complete addition, the reaction mixture was further heated at 130° C. for 16 hrs. After the completion of reaction, the reaction mixture was cooled to room temperature, concentrated under vacuum to get the crude product, which was purified by chiral preparative HPLC to get pure 1B (600 mg, 60%).

Step-2B

A solution of Intermediate 1B (0.5 g, 2.9 mmol) in dry ether (10 mL) was added in drops to a cooled suspension of LAH (0.433 g, 11.6 mmol) in dry diethyl ether at 0° C. After completion of addition, the reaction mixture was gradually allowed to reach room temperature and stirred for 12 h. The reaction was monitored by TLC (20% MeOH in DCM). After completion of reaction, the reaction mixture was cooled to 0° C., quenched successively with water (0.5 mL), 10% NaOH (1 mL) and water (1.5 mL). The precipitated solid was filtered through celite and the filtrate was concentrated under vacuum to get the product (2B) which was used as such for next step (product formation confirmed by $^1$H NMR). Yield: 300 mg, 70%.

Step-3B

To a solution of Intermediate 2B (0.3 g, 2 mmol) in 1,2 dichloroethane (10 mL), thionyl chloride (0.18 mL, 2.5 mmol) was added drop wise at 0° C. The reaction mixture was gradually heated to 80° C. for 2 h. After completion of reaction, the excess solvent and thionyl chloride were removed under reduced pressure to get the crude Intermediate B, which was taken as such for next step (product formation was confirmed by LCMS). Yield: 300 mg, 88%.

The following intermediates are or can be prepared following the method described for Intermediate A and Intermediate B, and using the appropriate reagents, and starting materials.

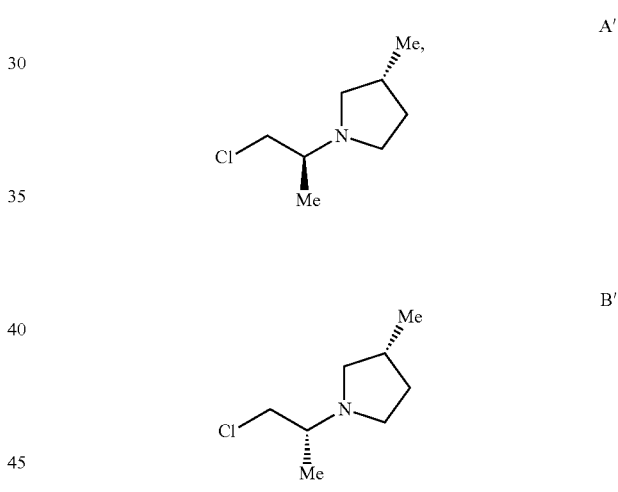

A'

B'

Representative Intermediate Synthesis 3

Representative Synthesis of 1-((2-Chloro-1-methyl)ethyl) pyrrolidine analogs

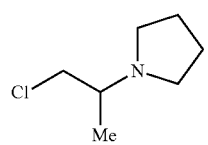

The intermediate chloroethylpyrrolidine derivatives can be prepared by following the representative method described in *Bioorganic & Medicinal Chemistry Letters* (2005) 15 3912-3916.

Intermediate C

The synthesis of a representative pyrrolidine derivative, 1-((S)-2-Chloro-1-methyl-ethyl)-pyrrolidine (Intermediate C) is given below.

Scheme 4

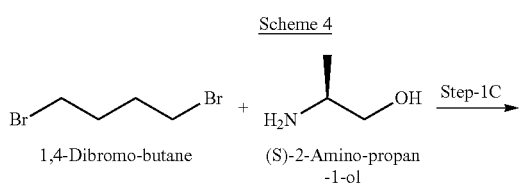

1,4-Dibromo-butane    (S)-2-Amino-propan-1-ol

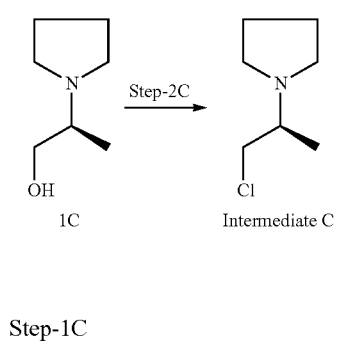

1C      Intermediate C

Step-1C

To a solution of 1,4 dibromo butane (500 mg, 2.31 mmol) in acetonitrile (8 mL) was added $K_2CO_3$ (0.64 g, 4.62 mmol) followed by (S)-2-amino propanol-1 (0.18 g, 2.31 mmol) in acetonitrile (2 mL) at room temperature. The reaction mixture was refluxed for 18 h. After completion of reaction (by TLC, 20% MeOH in DCM), the reaction mixture was allowed to reach room temperature and then filtered. The filtrate was concentrated under vacuum to get the crude 1C (300 mg) which was taken for next step without any further purification (product formation confirmed by $^1$H NMR).

Step-2C

To a solution of Intermediate 1C (300 mg, 2.3 mmol) in 1,2 dichloroethane (10 mL) was added $SOCl_2$ (0.2 mL, 2.7 mmol) drop wise and then slowly heated to 80° C. for 2 h. After completion of reaction (by TLC), excess solvent and thionyl chloride were removed under vacuum to get Intermediate C (300 mg, 87%), which was taken as such for next step (product formation was confirmed by LCMS). Yield: 300 mg, 87%.

The following intermediate is or can be prepared following the method described for Intermediate C, and using the appropriate reagents, and starting materials.

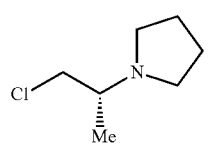

C'

Representative Intermediate Synthesis 4

Representative Synthesis of 1-((2-Chloro-1-methyl)ethyl) pyrrolidine analogs

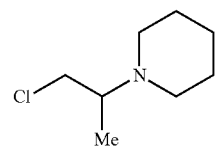

The intermediate chloroethylpyrrolidine derivatives can be prepared by following the representative method described below.

Intermediate D

The synthesis of a representative pyrrolidine derivative, 1-((S)-2-Chloro-1-methyl-ethyl)-piperidine (Intermediate D) is given below.

Scheme 5

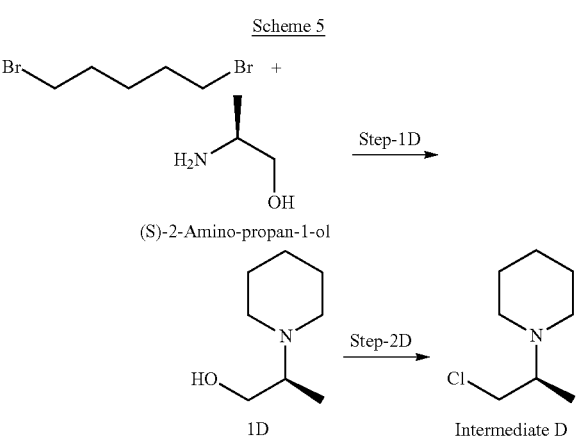

(S)-2-Amino-propan-1-ol

1D      Intermediate D

Step-1D

To a solution of 1,5 dibromo pentane (500 mg, 2.18 mmol) in acetonitrile (8 mL), was added $K_2CO_3$ (0.9 g, 6.55 mol) followed by (S)-2-amino propanol-1 (163 mg, 2.18 mmol) in acetonitrile (2 mL) at room temperature. The reaction mixture was heated to reflux for 18 hrs. After completion of reaction (by TLC), the reaction mixture was cooled to room temperature, filtered and the filtrate was concentrated to get the crude product (1D) which was taken as such for next step. Yield: 300 mg.

Step-2D

To a solution of Intermediate 1D (300 mg, 2.1 mmol) in 1,2 dichloroethane (10 mL) was added $SOCl_2$ (0.2 mL, 2.5 mmol) drop wise and then slowly heated to 80° C. for 2 h. After completion of reaction (by TLC), excess solvent and thionyl chloride were removed under vacuum to get Intermediate D (300 mg, 88%), which was taken as such for next step (product formation confirmed by LCMS).

The following intermediate is or can be prepared following the method described for Intermediate C, and using the appropriate reagents, and starting materials.

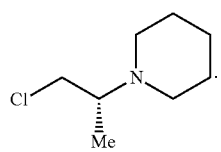

Representative Intermediate Synthesis 5

The intermediate benzopyran derivatives can be prepared by following the representative method described below.

Intermediate E

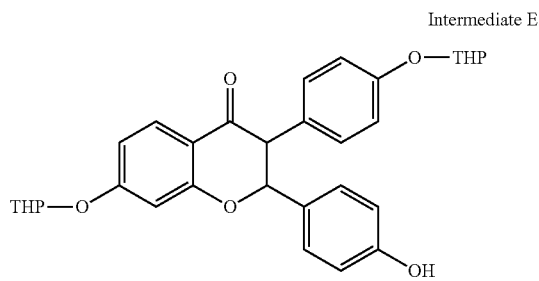

THP = tetrahydropyranyl

Scheme 6

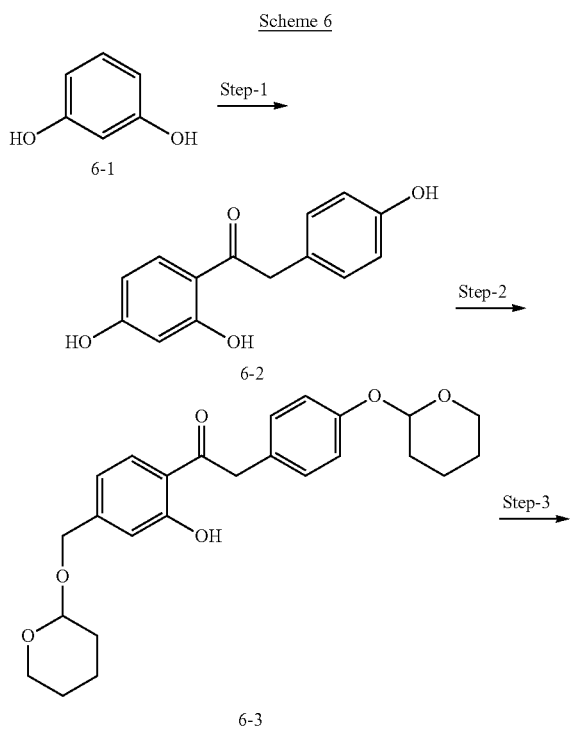

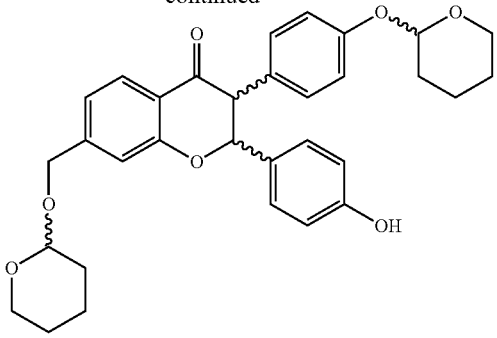

6-4
Intermediate E

Step-1

A suspension of resorcinol (6-1) (40 g, 0.363 mol) and 4-hydroxyphenylacetic acid (49 g, 0.326 mol) in BF$_3$.etherate (1.09 mol, 138 mL) was refluxed for 15 min under argon atmosphere (the reaction mixture became clear solution). The reaction was monitored by TLC (30% pet ether in ethyl acetate was used as eluting solvent). After completion of the reaction, the reaction mixture was cooled in an ice bath and then poured into an excess of ice-water. The resulting yellow precipitate obtained was collected by filtration and washed with 20% Pet ether/ethyl acetate followed by 25% ethanol-water to give Intermediate 6-2 as off-white solid. Yield 45 g, 51%.

Step-2

To a suspension of Intermediate 6-2 (15 g, 0.061 mol) in 3,4-dihydro-2H-pyran (52 g, 0.61 mol) was added p-toluene-sulfonic acid monohydrate (584 mg, 3 mmol) at −10° C. The reaction mixture was stirred for 45 min at 0° C. The reaction was monitored by TLC (30% pet ether in ethyl acetate as eluting solvent). After completion of reaction, the reaction mixture was treated with saturated sodium bicarbonate and diethyl ether. The organic phase was separated, washed with saturated sodium bicarbonate, brine and dried over sodium sulfate. The solvent was concentrated under reduced pressure to get crude compound, which was purified by flash column chromatography (silica gel, pet ether/ethyl acetate as solvents) to get pure Intermediate 6-3 as white solid. Yield: 17 g, 67%.

Step-3

A solution of Intermediate 6-3 (6 g, 0.015 mol), 4-hydroxy-benzaldehyde (1.59 g, 0.013 mol) and piperidine (370 mg, 4.0 mmol) in benzene (100 mL) was refluxed using Dean-Stark apparatus for 16 h. The reaction was monitored by TLC (using 25% ethyl acetate in Pet ether as eluting solvent). After completion of reaction, the reaction mixture was cooled to room temperature and the solvent was removed under reduced pressure to get crude product. The crude product was purified by flash column chromatography (silica gel, Pet ether/ethyl acetate as solvent system) to get Intermediate 6-4 (Intermediate E) as white solid. Yield: 1.6 g, 21%.

Synthesis of Representative Compounds

Synthesis of OP-1038 (Alkylation Method)

Scheme 5

Step-4:

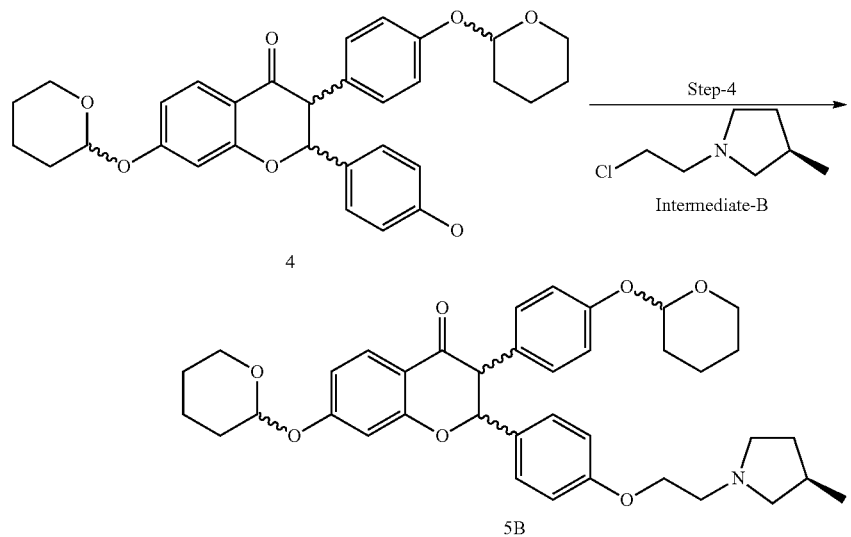

To the stirred solution of Intermediate-4 (0.25 g 0.48 mmol) in dry acetone (10 mL) was added cesium carbonate (0.47 g, 1.4 mmol) at 0° C. and stirred for 10 min. A solution of (R)-1-(2-chloro-ethyl)-3-methyl-pyrrolidine hydrochloride (Intermediate-B) (90 mg, 0.58 mmol) in 2 mL acetone was added at 0° C. After completion of addition, the reaction mixture was gradually heated to reflux and maintained for 18 h. The reaction mixture was filtered, washed with acetone and concentrated to get Intermediate-5B as yellow oil. The crude product was taken as such for next step (product formation was confirmed by LCMS). Yield: 0.210 g (crude) 68%.

Scheme 6

Step-5:

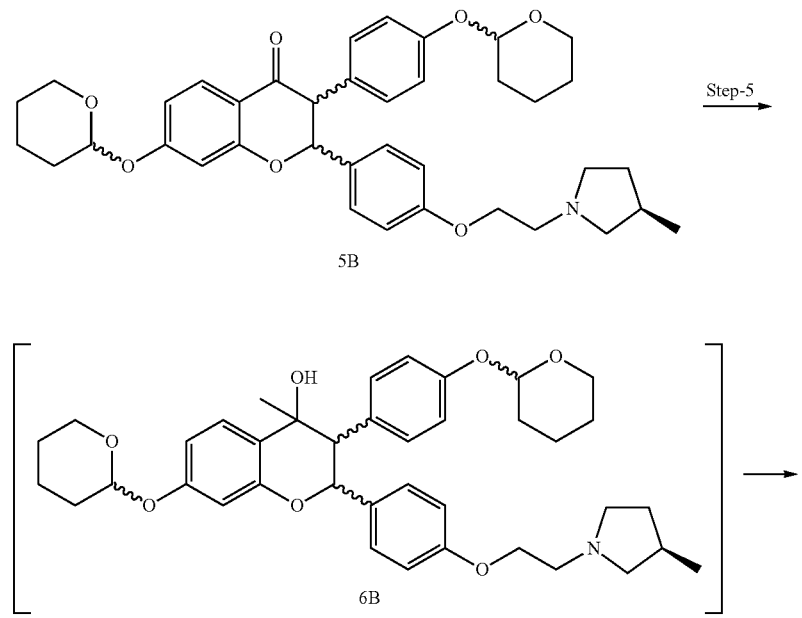

-continued

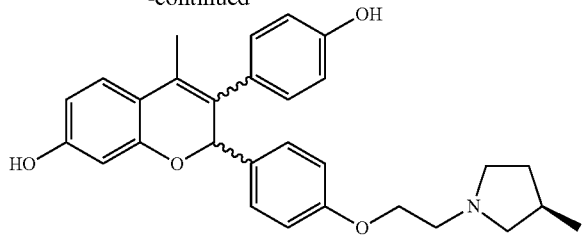

To a cooled (0° C.) solution of Intermediate-5B (200 mg, 0.31 mmol) in dry THF (5 mL), CH₃MgI (1.2 mL, 1.5 M solution in THF, 1.55 mmol) was added drop wise. After completion of addition, the reaction mixture was slowly allowed to reach room temperature and stirred for 6 h. Then reaction mixture was cooled to 0° C., quenched with ammonium chloride solution (10 mL) and extracted with EtOAc (3×10 mL). The combined organic layer was dried over anhydrous sodium sulphate, filtered and concentrated under vacuum to get crude intermediate 6B as yellow oil. This was taken in acetic acid (9 mL) and water (1 mL) and heated to 90° C. for 2 h. The reaction mixture was cooled to room temperature and concentrated under vacuum to remove the solvents. The residue was taken in EtOAc and quenched with saturated NaHCO₃ solution at 0° C. The organic layer was separated and aqueous layer extracted with EtOAc (2×10 mL). The combined organic layer was dried over anhydrous sodium sulphate, filtered and concentrated to get the crude product. The crude product was purified by flash column chromatography (silica gel, EtOAc/Pet ether) followed by preparative HPLC to get pure OP-1038 as beige colored solid. Yield: 25 mg, 18%.

Following the general method above and using the appropriate reagents and starting materials OP-1039, OP-1042, OP-1049, OP-1050, and OP-1053 were synthesized.

Synthesis of OP-1060 and OP-1061

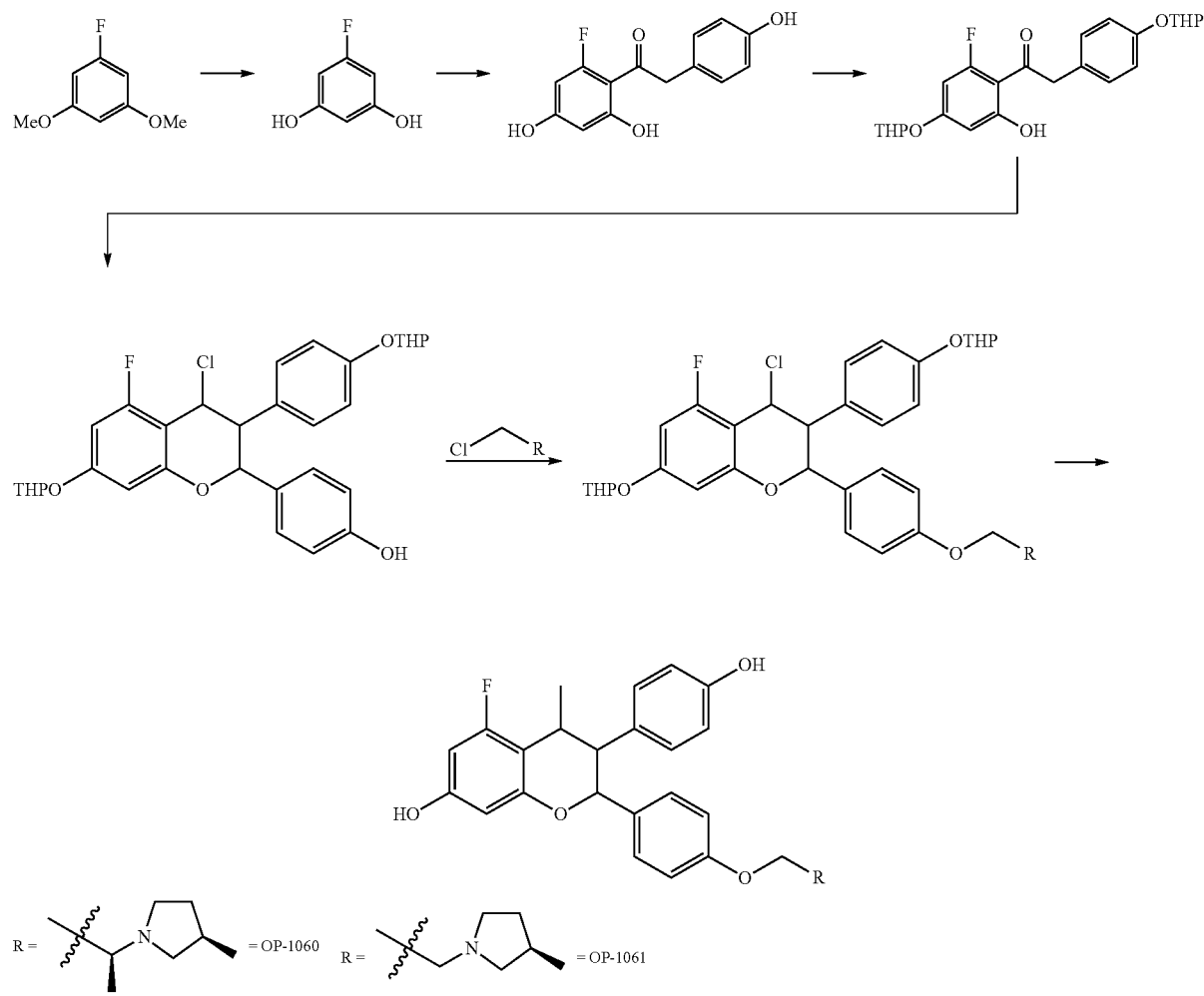

Step-1

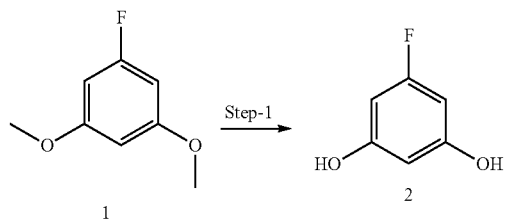

A solution of dimethoxy fluorobenzene (1) (10 g, 64 mmol) in dry dichloromethane (40 mL) was cooled to −30° C. To the cooled solution was added a solution of $BBr_3$ (35.93 mL, 384 mmol) in 60 mL of DCM slowly (in drops) over 30 min. After completion of addition, the reaction mixture was allowed to reach 25° C. and stirred for 12 h. After completion of reaction (by TLC using 30% ethyl acetate and pet ether as eluting solvent), reaction mixture was cooled to 0° C. and then slowly quenched with water and stirred for 30 min at 25° C. The reaction mixture was extracted with dichloromethane (3×100 mL) and the combined organic layer was washed with sodium bicarbonate, dried over $Na_2SO_4$ and concentrated to get the product (2) as light brown solid. Yield: 8 g (97%)

Step-2

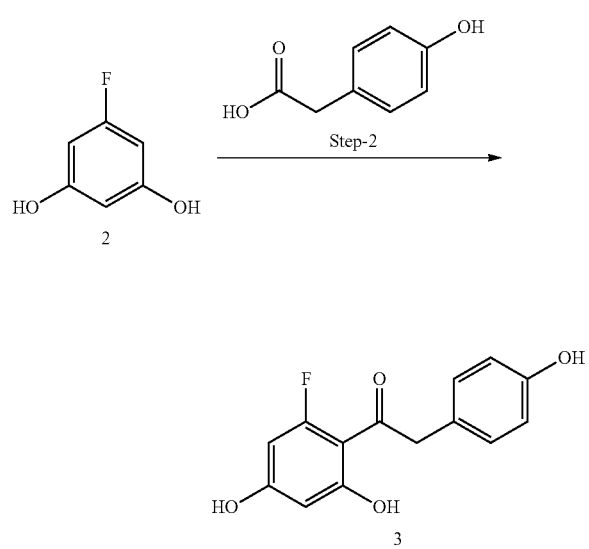

A mixture of Fluoro resorcinol (2) (9 g, 70 mmol) and 4-hydroxyphenylaceticacid (9.62 g, 63 mmol) in $BF_3$-$Et_2O$ (26.7 ml, 210 mmol) were stirred under reflux for 15 min T. After completion of the reaction (monitored by TLC, using 30% ethyl acetate and pet ether as eluting solvent) the reaction mixture was cooled in an ice bath and poured into excess of ice-water and extracted with ethyl acetate (3×100 mL). The combined ethyl acetate layer was dried over anhyd $Na_2SO_4$ and concentrated under vacuum to get the crude product as mixture of regioisomers. Preparative HPLC purification afforded the require isomer (3) as beige colored solid. Yield: 4.5 g (25%).

Step-3

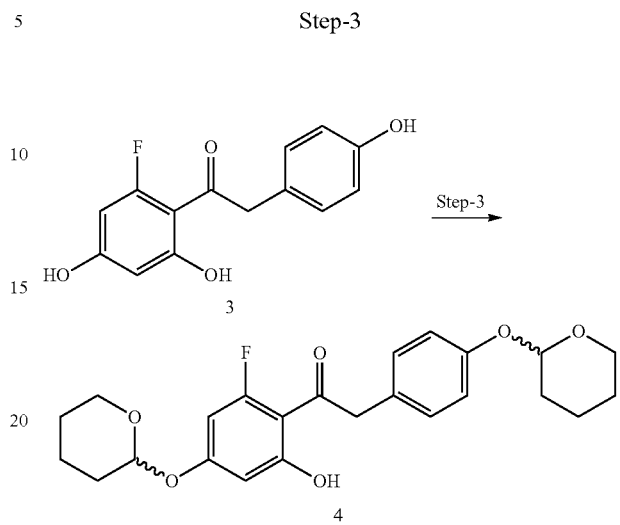

A suspension of Intermediate 3 (6 g, 23 mmol) in 3,4-dihydro-2H-pyran (23.28 mL, 270 mmol) was treated with catalytic amount (2 drops) of conc.HCl at −10° C. The reaction mixture was stirred for 45 min at 0° C. After completion of reaction (by TLC using 30% pet ether and ethyl acetate as eluting solvent), the reaction mixture was treated with saturated sodium bicarbonate and diethyl ether (100 mL). The organic layer was separated, dried over sodium sulfate and evaporated under reduced pressure to get the crude product as yellow oil. This was recrystallized from with hexane and diethyl ether to get compound 4 as white solid. Yield: 3.4 g (34%).

Step-4

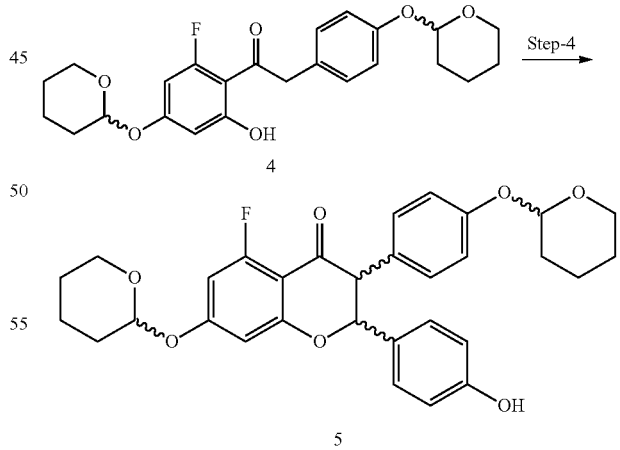

A solution of bis-THP ether Intermediate 4 (5 g, 11.6 mmol), 4-hydroxybenzaldehyde (1.27 g, 10.4 mmol) and piperidine (0.114 mL, 11.6 m) in benzene (50 mL) was stirred and refluxed using a Dean-Stark apparatus for 16 h. After cooling to room temperature, the solvent was removed under reduced pressure to get crude product. The crude material was purified by column chromatography (silica gel, pet ether/ethyl acetate) to get Intermediate 5 as a pale yellow solid. Yield: 2 g (32%).

Synthesis of OP-1060

Step-5A

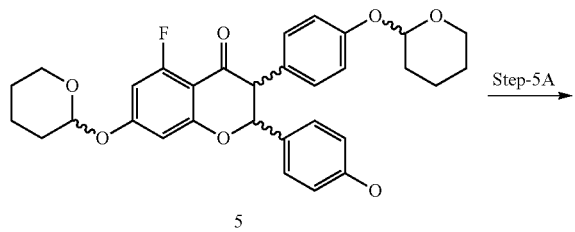

5

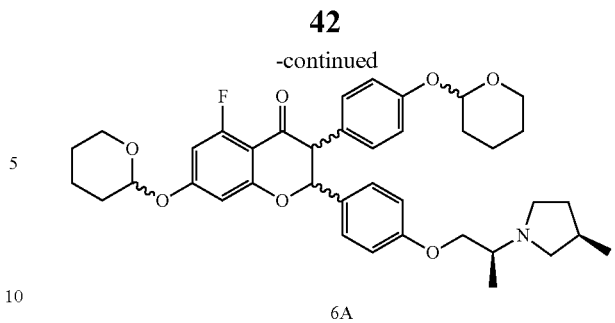

6A

To the stirred solution of Intermediate 5 (500 mg, 0.93 mmol) in dry acetone (15 mL), cesium carbonate (911 mg, 2.8 mmol) was added at 0° C. The reaction mixture was stirred for 10 min at 0° C., and (R)-1-((S)-2-Chloro-1-methyl-ethyl)-3-methyl-pyrrolidinehydrochloride (3A) (185 mg, 0.93 mmol) was added and heated to 60° C. for 19 h. After completion of reaction (by TLC using ethyl acetate and 10% methanol as eluting solvent), the reaction mixture was filtered, washed with acetone and concentrated to get the crude product. The crude product was purified by column chromatography (silica gel, pet ether/ethyl acetate) to get pure Intermediate 6A as yellow solid. The product formation was confirmed by LCMS. Yield: 200 mg (30%)

Step-6A & Step-7A

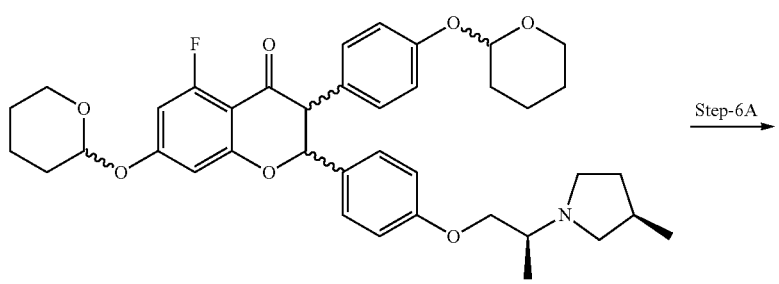

6A

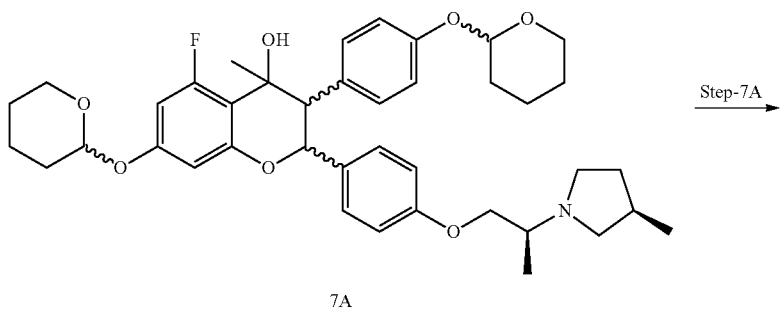

7A

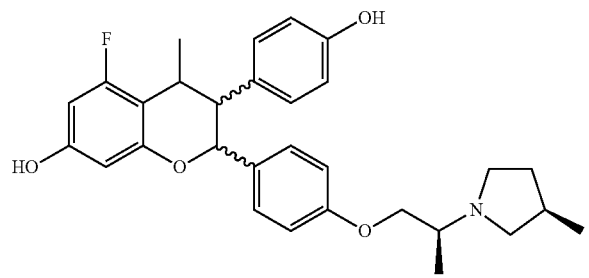

OP-1060

To a cooled solution (−5° C.) of Intermediate 6A (300 mg, 0.45 mmol, 1 eq) in dry THF (5 mL) was added MeMgBr (1.4M in THF, 3.20 mL, 4.50 mmol) slowly in drops. After completion of addition, the reaction mixture was allowed to reach 25° C. and stirred for 6 h. After completion of reaction (monitored by LCMS), the reaction mixture was quenched with satd ammonium chloride solution and extracted with ethylacetate (3×2 o mL). The combined organic layer was dried over anhydrous sodium sulphate and concentrated under vacuum to get the crude Intermediate 7 as yellow oil (the product was confirmed by LCMS). The crude Intermediate 7A was dissolved in acetic acid (9 mL) and water (1 mL) and heated to 90°C for 3 h. After completion of reaction (by TLC, using 20% MeOH and ethyl acetate as eluting solvent), the reaction mixture was cooled to 25° C. and concentrated under vacuum. The residue obtained was taken in EtOAc and quenched with saturated NaHCO$_3$ solution at 0° C. The organic layer was separated and aqueous layer extracted with EtOAc (2×10 mL). The combined organic layer was dried over anhydrous sodium sulphate, filtered and concentrated to get the crude product. The crude product was purified by flash column chromatography (silica gel, EtOAc/Pet ether) followed by preparative HPLC to get pure OP-1060 as beige colored solid. Yield: 60 mg (27%).

Following the above procedure and using the appropriate reagents and starting materials, OP-1061 was also synthesized.

Synthesis of OP-1056

3-(4-Hydroxyphenyl)-2-(4-(2-((R)-3-methylpyrrolidin-1-yl)ethoxy)phenyl)-4-(trifluoromethyl)-2H-chromen-7-ol

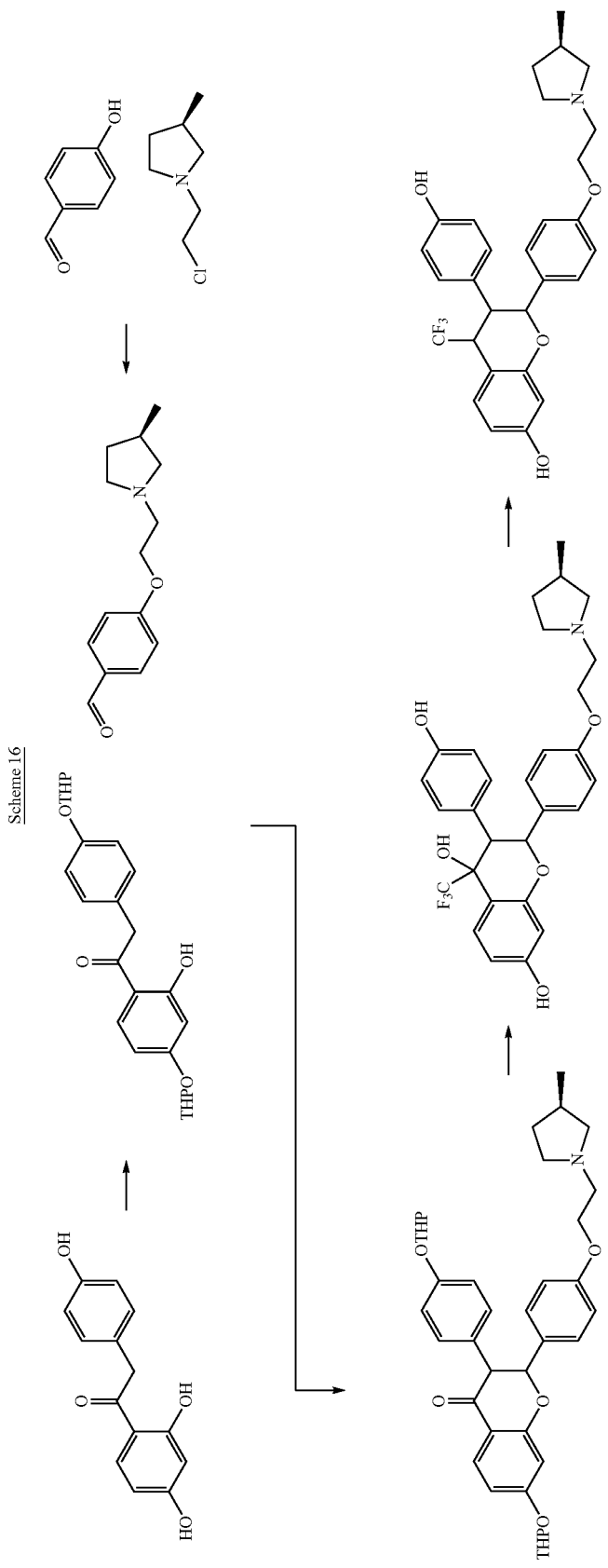

2-(4-(2-((R)-3-Methylpyrrolidin-1-yl)ethoxy)phenyl)-7-((tetrahydro-2H-pyran-2-yl)oxy)-3-(4-((tetrahydro-2H-pyran-2-yl)oxy)phenyl)chroman-4-one (8')

To a solution of 6' (1.0 g, 4.3 mmol), resorcinol derivative 7' (2.1 g, 5.1 mmol) and piperidine (0.17 mL, 1.7 mmol) in toluene (150 mL) is heated at reflux with azeotropic removal of water for 24 hours. The solution is concentrated and the residue is purified by silica gel column chromatography using a gradient of 0 to 8% methanol in dichloromethane to yield 8' as a brown viscous oil (1.4 g, 52% yield).

MS Calculated $C_{38}H_{45}NO_7+H'=628$; Observed 628.

3-(4-Hydroxyphenyl)-2-(4-(2-((R)-3-methylpyrrolidin-1-yl)ethoxy)phenyl)-4-(trifluoromethyl)chroman-4,7-diol (9')

To a solution of 8' (1.0 g, 1.6 mmol), trimethyl(trifluoromethyl)silane (1.1 mL, 7.5 mmol) is added cesium fluoride (0.045 g, 0.29 mmol) and the solution is stirred at room temperature for 48 hours. The reaction mixture is concentrated and the residue is dissolved in ethyl acetate (100 mL) and washed with brine, dried over anhydrous sodium sulfate, filtered, and concentrated to yield a brown residue that is purified by silica gel column chromatography with using a gradient of 0 to 8% methanol in dichloromethane to yield 9' as a yellow solid (0.5 g, 59% yield).

MS Calculated $C_{29}H_{30}F_3NO_5+H^+=530$. Observed 530.

3-(4-Hydroxyphenyl)-2-(4-(2-((R)-3-methylpyrrolidin-1-yl)ethoxy)phenyl)-4-(trifluoromethyl)-2H-chromen-7-ol (10') (OP-1056)

To a solution of 9' (0.5 g, 0.94 mmol) in tetrahydrofuran (2 mL) is added triethylamine (6.6 mmol, 0.91 mL) and trifluoroacetic anhydride (2.8 mmol, 0.39 mL) simultaneously at 0° C. and the solution is allowed to warm to room temperature with stirring for 16 hours. The solution is concentrated and the residue is dissolved in ethyl acetate (100 mL) and washed with brine, dried over anhydrous sodium sulfate, filtered, and concentrated to yield a brown residue that is purified by silica gel column chromatography with using a gradient of 0 to 10% methanol in dichloromethane to yield a yellow solid. This solid was further purified by preparative HPLC to yield, after lyophylization (0.024 g, 4.9% yield).

MS Calculated $C_{29}H_{28}F_3NO_4+H^+=512$. Observed 512.

The syntheses of representative compounds of this invention can be carried out in accordance with the representative methods set forth below and using the appropriate reagents, starting materials, and purification methods known to those skilled in the art.

Synthesis of 3-(4-hydroxyphenyl)-4-methyl-2-(4-{2-[(3R)-3-methylpyrrolidin-1-yl]ethoxy}phenyl)-2H-chromen-7-ol (OP-1038) and Separation and Purification of Stereoisomers (OP-1074 and OP-1075)

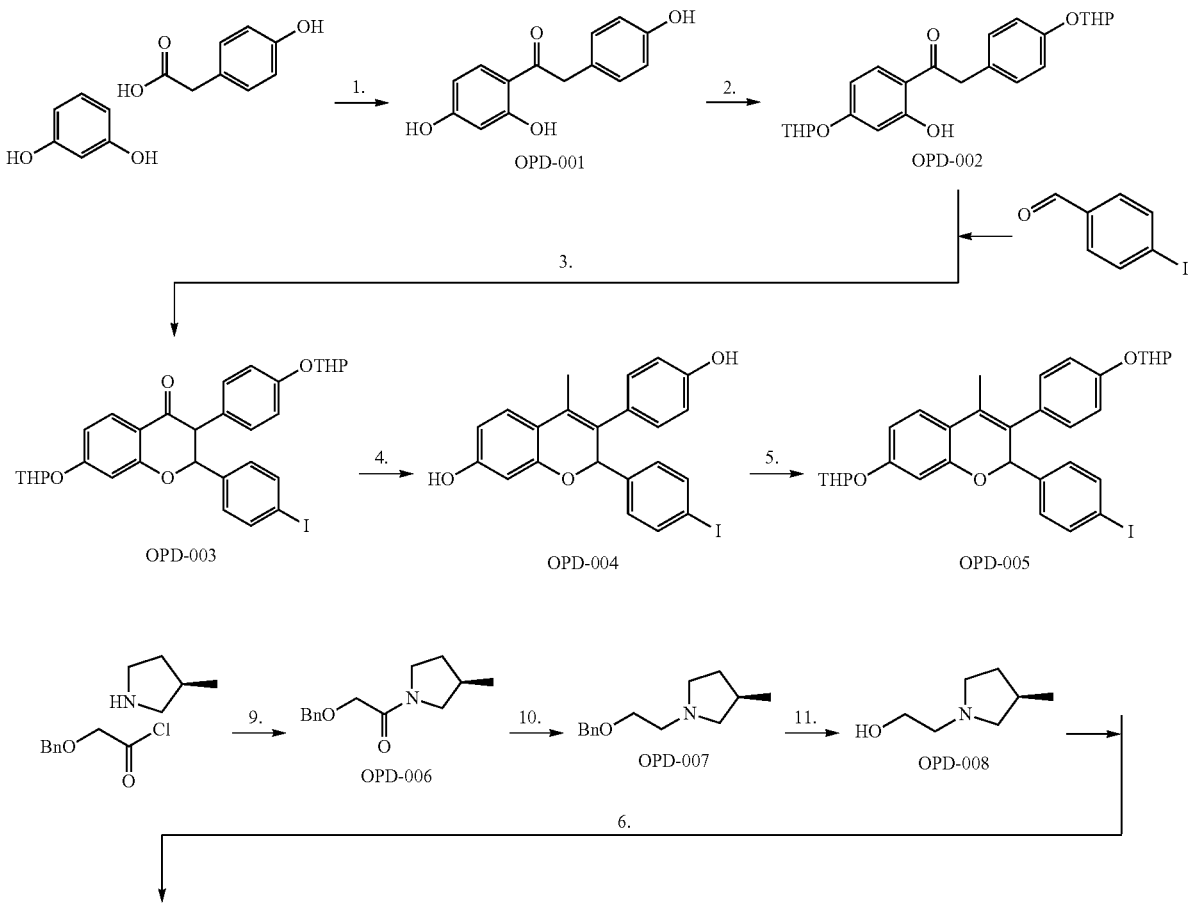

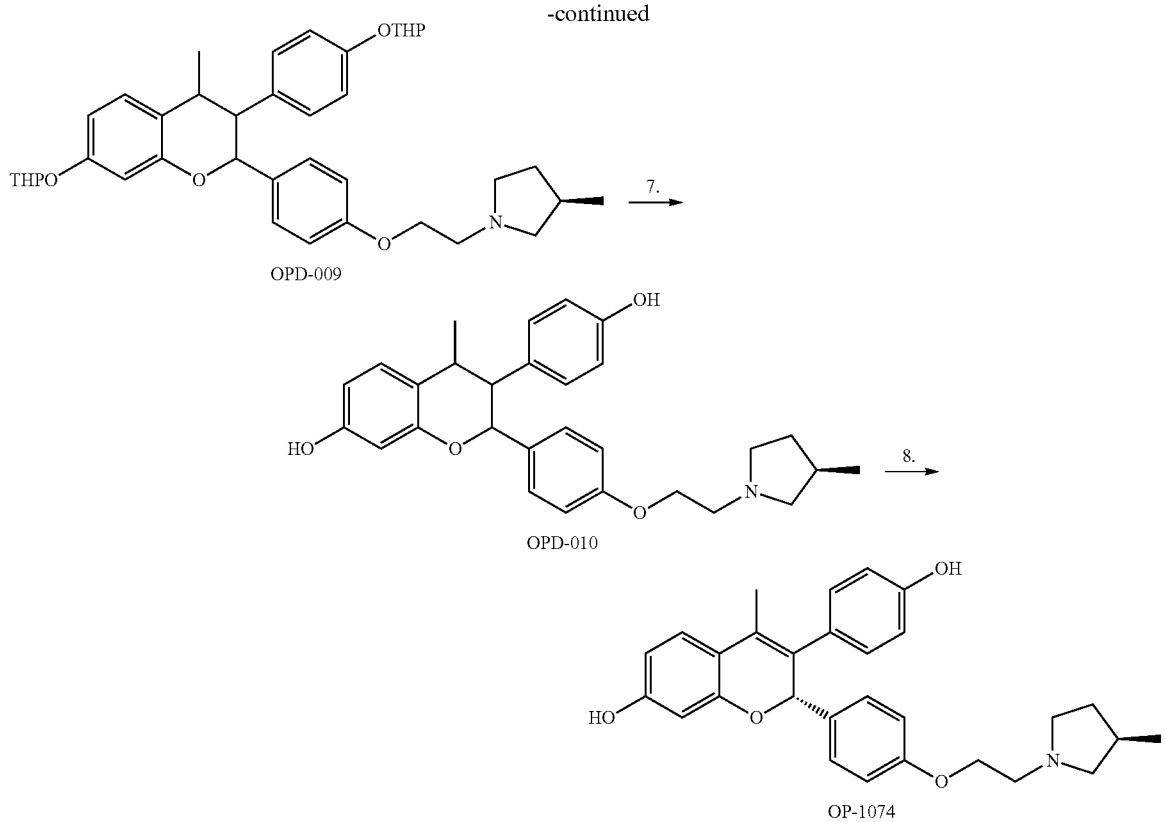

Step 1

Reaction to Produce 1-(2,4-Dihydroxyphenyl)-2-(4-hydroxyphenyl)ethanone

Resorcinol (1,3-dihydroxybenzene) (62.000 g, 563.1 mmol, 1.0 equiv.) and 4-Hydroxyphenylacetic acid (94.237 g, 619.4 mmol, 1.1 equiv.) were added to a 3 neck 2 L round bottomed flask fitted with a paddle, a pressure equalizing addition funnel and a thermometer and a heating mantle. Toluene (350 mL) was added to the flask to give a suspension. The reaction purged with nitrogen and the addition funnel filled with Boron trifluoride etherate (198.201 ml, 1578.0 mmol, 2.8 equiv.) via canula. The reaction was stirred at 150 rpm and boron trifluoride etherate was added in portions of 3-4 mL and the reaction heated. During addition the internal temperature rose to 100° C. The reaction went through various changes in color from yellow to dark red. After complete addition of boron trifluoride etherate the addition funnel was removed and replaced with a condenser. The reaction was stirred for 1.5 h at an internal temperature of 108° C. A sample was taken and HPLC analysis indicated the reaction was complete. The reaction was cooled and stirring stopped to give a biphasic solution. A 12% aqueous solution of sodium acetate (41 g, 336 mL) was slowly added to the reaction with stirring. The reaction was stirred for 16 hours. A precipitate formed overnight and was collected in a sintered glass funnel. The solid was dried on a vacuum oven for 16 h to give the product as a white powder (119.67 g, 87.0%).

Step 2

Reaction to Produce 1-(2-hydroxy-4-((tetrahydro-2H-pyran-2-yl)oxy)phenyl)-2-(4-((tetrahydro-2H-pyran-2-yl)oxy)phenyl)ethanone 1-(2,4-Dihydroxyphenyl)-2-(4-hydroxyphenyl)ethanone (119.000 g, 487.2 mmol, 1.0 equiv.) and ethyl acetate (400 mL) was added to a 2 L 3 neck round bottomed flask equipped with a stir bar a thermometer, a condenser and a nitrogen inlet. The flask was flushed with nitrogen for 2 minutes and 3,4-dihydro-2H-pyran (222.252 ml, 2436.1 mmol, 5.0 equiv.) was added from a graduated cylinder. The suspension was flushed with nitrogen for 2 minutes and p-toluenesulfonic acid (0.378 g, 2.2 mmol, 0.0 equiv.) was added to the reaction. An exothermic reaction took place and the temperature rose from 20 to 33° C. over 5 minutes. The yellow suspension became a red solution within 1 minute of PTSA addition. The reaction was stirred for 66 h at room temperature. The reaction was monitored by HPLC at 4, 5 and 6 hours. The chromatograms indicated the reaction was 74%, 90% and 100% complete at the time indicated respectively. TEA (5 mL) was added to the cream colored slurry to stop the reaction. The slurry was transferred to a round bottomed flask (2 L) and the three neck flask rinsed with ethyl acetate. The slurry was concentrated on a rotovap to give a cream colored powdery solid. The solid was transferred to a 2 L Erlenmeyer flask. Isopropyl alcohol (IPA) was used to rinse the flask. The solid was recrystallized from IPA (1.4 L). The suspension was cooled in an ice bath for 30 minutes and the solid collected by vacuum filtration. The solid was rinsed with ice cold IPA until the filtrate was colorless and dried in a vacuum oven to give a white powder (162.24 g). The mother liquor and washes were combined and concentrated to an orange oil (38.09 g).

Step 3

Reaction to Produce 2-(4-iodophenyl)-7-((tetrahydro-2H-pyran-2-yl)oxy)-3-(4-((tetrahydro-2H-pyran-2-yl)oxy)phenyl)chroman-4-one 1-(2-hydroxy-4-((tetrahydro-2H-pyran-2-yl)oxy)phenyl)-2-(4-((tetrahydro-2H-pyran-2-yl)oxy)phenyl)ethanone (16.228 g, 39.34 mmol) was added to a 3 neck 1 L RB flask. 2-Butanol (380 mL, 0.197 M) and 4-iodobenzaldehyde (51.700 g, 222.8 mmol, 1.0 equiv.) was added to the flask to give a suspension. Piperidine (7.300 ml, 73.9 mmol, 0.3 equiv.) and 1,8-Diazabicyclo[5.4.0]undec-7-ene (11.300 ml, 75.6 mmol, 0.3 equiv.) was added to the suspension. The flask was fitted with a Dean-Stark apparatus and condenser, a thermometer, a stirrer shaft and heated in an oil bath at 130° C. to give an orange solution (became a solution when the internal temperature was 80° C.). Half the solvent (190 mL) was collected over 1.5 hours. The Dean-Stark trap was removed and the condenser was placed on the flask the reaction heated for a further 1 hour. The solution gradually darkens to an orange color. The oil bath was cooled to 90° C. and 380 mL of isopropyl alcohol was added in one portion. The reaction mixture became a cloudy white suspension and redissolved to give a solution in less than a minute at 90° C. The heating to the bath was set to 50° C. and the flask was allowed to gradually cool to 50° C. A precipitate started to form at 60° C. and gave a suspension at 50° C. A thick oily mass falls out of solution ~55-53° C. Vigorous agitation with overhead stirrer (300 rpm) was required to prevent the oily mass from solidifying into one solid as seen with small scale reactions equipped with stir bar. The reaction was left to stir until the mixture cooled to room temperature. The oily mass solidified into a cake even with vigorous agitation. The mother liquor was decanted and fresh isopropanol (100 mL) was added to the flask to rinse the solid. The liquid was decanted and combined with the mother liquor. The mother liquor was concentrated to a dark red oil (27.13 g) and DCM (150 mL) was added to the flask to give a red solution. Silica gel (55 g) was added to solution and concentrated to dryness. The silica gel mixture was poured into a 600 mL sintered glass funnel filled with silica gel (50 g). The solids were washed with ethyl acetate (1.2 L) and the filtrate concentrated to an orange oil (137.61 g crude). The oil was dissolved into boiling 80% IPA/water (1.2 L) and the solution allowed to cool to room temperature and stand overnight to give a cake. The cake was filtered and washed with cold IPA (100 mL). The mother liquor was partially concentrated on a rotovap to give a tan powder. This process was repeated until an oil could not be washed away from the powder. The product was pooled and dried in a vacuum oven to give an impure tan powder (118.25 g, 85.6%).

Step 4a

Reaction to Produce 2-(4-iodophenyl)-4-methyl-7-((tetrahydro-2H-pyran-2-yl)oxy)-3-(4-((tetrahydro-2H-pyran-2-yl)oxy)phenyl)chroman-4-ol To a solution of 90.0% 2-(4-iodophenyl)-7-((tetrahydro-2H-pyran-2-yl)oxy)-3-(4-((tetrahydro-2H-pyran-2-yl)oxy)phenyl)chroman-4-one (104.891 g, 150.7 mmol, 1.0 equiv.) in THF (1.2 L) at 5° C., was added Methylmagnesium chloride 3.0 M solution in THF (160.000 ml, 480.0 mmol, 3.2 equiv.) by addition funnel over 30 minutes. The temperature did not rise about 8° C. during the addition. The reaction was removed from the ice bath and stirred at room temperature and stirred for another hour. TLC (20% ethyl acetate in hexanes) showed the reaction had no starting material. The solution was cooled in an ice bath, and carefully quenched with saturated ammonium chloride (35 mL). Ethyl acetate (1.2 L) and water (1.2 L) were added to the reaction mixture, and the layers were separated. The aqueous layer was extracted with EA (1 L). The combined organic layer was washed with brine (1 L), dried over anhydrous $Na_2SO_4$, filtered and concentrated in vacuo to yield a pale yellow foam (111.26 g crude). This material was used without further purification.

Step 4b

Reaction to Produce 3-(4-hydroxyphenyl)-2-(4-iodophenyl)-4-methyl-2H-chromen-7-ol 2-(4-iodophenyl)-4-methyl-7-((tetrahydro-2H-pyran-2-yl)oxy)-3-(4-((tetrahydro-2H-pyran-2-yl)oxy)phenyl)chroman-4-ol (96.820 g, 150.7 mmol, 1.0 equiv.) and 80% acetic acid in $H_2O$ (686 mL) was added to a 2 L RB flask. The suspension was degassed, flushed with nitrogen and heated at 90° C. for 1.5 hours. TLC analysis (1:2 EA/Hex) of the reaction showed no starting material was present. The solvent was removed to give a red oil. The red oil was dissolved into ethyl acetate (500 mL) and washed with saturated sodium bicarbonate solution (3×1 L). The organic layers was washed with brine (1 L), filtered and concentrated to give a red oil (109.32 g, crude). The oil was loaded onto 100 g of silica gel and chromatographed in 40 g portions on silica gel (100 g cartridge, 5-30% EA/Hex). Fractions containing spots with Rf 0.55 (33% EA/Hex) were pooled and concentrated to a light red glass (53.37 g). The glass was mixed with DCM (200 mL) and sonicated to give a pink suspension. The solid was filtered through a sintered glass funnel washed with a 20% DCM in Hexanes solution (250 mL) and dried in a vacuum oven overnight (32.41 g). The mother liquor was concentrated to a glass and the process repeated a second time to give a pink solid (4.2784 g). The impure mixed fractions were pooled and concentrated to a glass (16.71 g). The glass was dissolved into DCM (75 mL) and pink crystals formed on standing (7.0862 g). This process was repeated to give a second crop of pink crystals (2.3643). The mother liquors from both the pure and impure fractions were combined and chromatographed with the same method (2×100 g cartridges). The fractions with Rf 0.55 were pooled and concentrated to give a red oil (17.388 g) which did not solidify. The oil was not combined with previous batches but reprotected in a separate reaction.

Gradient method: (5-30% EA/Hex) 5% EA hold for 2 minutes, gradient to 15% over 3 minutes and hold at 15% EA/Hex for 7 minutes, gradient to 30% over 7 minutes and hold at 30% EA/Hex for 17 minutes. Fractions with Rf 0.55 (33% EA/Hex) were pooled and concentrated to a light pink oil which was triturated with DCM.

Step 5

Reaction to Produce 2-(4-iodophenyl)-4-methyl-7-((tetrahydro-2H-pyran-2-yl)oxy)-3-(4-((tetrahydro-2H-pyran-2-yl)oxy)phenyl)-2H-chromene To a solution of 3-(4-hydroxyphenyl)-2-(4-iodophenyl)-4-methyl-2H-chromen-7-ol (41.860 g, 91.7 mmol, 1.0 equiv.) and pyridinium para-toluene sulfonate (4.822 g, 19.3 mmol, 0.2 equiv.) in DCM (200 mL) was added 3,4-dihydro-2H-pyran (49.226 ml, 539.6 mmol, 5.9 equiv.). The reaction was stirred at room temperature overnight (17 h). TLC showed major desired product. The reaction was diluted with DCM (200 mL), washed with saturated NaHCO3 (200 mL), water (200 mL), brine (200 mL), dried over Na2SO4, filtered and concentrated to give a red viscous residue. The residue adsorbed onto silica gel (75 g) was purified on a silica gel column (4×100 g, 0-20% EA/Hex) to give a white solid which was triturated with methanol and dried in a vacuum oven at 40° C. for 16 h to afford the titled compound as a white powder (51.67 g 90.2%).

$^1$H NMR (300 MHz, CDCl$_3$): δ 7.53 (d, J=5.4 Hz, 2H)), 7.18 (d, J=8.7 Hz, 1H), 7.06 (aprent t, J=7.8 Hz, 4H), 6.71 (s, 1H), 6.59 (d, J=2.4 Hz, 1H), 6.45 (d, J=2.4 Hz, 1H), 5.15 (s, 2H), 4.59 (s, 2H), 4.63 (d, J=5.7 Hz, 2H), 3.98 (s, 3H), 3.84 (s, 3H).

Step 6

Reaction to Produce -(3R)-3-methyl-1-(2-(4-(4-methyl-7-((tetrahydro-2H-pyran-2-yl)oxy)-3-(4-((tetrahydro-2H-pyran-2-yl)oxy)phenyl)-2H-chromen-2-yl)phenoxy)ethyl)pyrrolidine A mixture of 2-(4-iodophenyl)-4-methyl-7-((tetrahydro-2H-pyran-2-yl)oxy)-3-(4-((tetrahydro-2H-pyran-2-yl)oxy) phenyl)-2H-chromene (16.800 g, 26.9 mmol, 1.0 equiv.), (R)-2-(3-methylpyrrolidin-1-yl)ethanol (10.416 g, 80.6 mmol, 3.0 equiv.), 1,10-Phenanthroline (0.970 g, 5.4 mmol, 0.2 equiv.), and Cesium carbonate (17.530 g, 53.8 mmol, 2.0 equiv.) in butyronitrile (84 mL) was charged into a 250 mL round bottom flask which was evacuated and backfilled with argon (3×), Copper(I) iodide (5.123 g, 26.9 mmol, 1.0 equiv.) was added to the suspension and evacuated and backfilled with argon (3×). The reaction mixture was heated in an oil bath at 120° C. After 91 h of heating the reaction was cooled to room temperature and the mixture filtered through a pad of Celite (3 cm) which was successively washed with DCM (200 mL), EA (200 mL) and MeOH (200 mL). The filtrate was collected and concentrated. The residue was adsorbed onto silica gel (25 g) purified with silica gel (100 g cartridge, 0-30% MeOH/DCM) [TLC: 5% MeOH/DCM, 4 major spots, Rf (SM:0.95), 0.9, 0.83, (prod. 0.43)]. The fractions containing product were pooled and concentrated to give a brown foam (13.64 g, 81.0%).

Gradient method 0% MeOH 4 minutes, gradient to 1% MeOH/DCM over 3 minutes, hold at 1% MeOH/DCM for 10 minutes, gradient to 5% MeOH/DCM over 3 minutes, hold at 5% MeOH/DCM for 12 minutes, gradient to 25% MeOH/DCM over zero minutes, hold at 25% MeOH/DCM for 15 minutes. Many fractions contained a mixture of the starting material and product all fractions were pooled, concentrated, and rechromatographed on silica gel (loaded onto 15 g and 100 g cartridge) and gradient eluted with this gradient method (0% MeOH 4 minutes, gradient to 1% MeOH/DCM over 3 minutes, hold at 1% MeOH/DCM for 20 minutes, gradient to 5% MeOH/DCM over 5 minutes, hold at 5% MeOH/DCM for 20 minutes). Fractions 74 to 126 were pooled and concentrated to a brown oil which solidified to foam (13.64 g, 81%) (Late eluting fractions from the first column contained a spot which corresponded to the aminoalcohol. These fractions were pooled and concentrated to give a red black liquid (6.38 g).

Step 7

Reaction to Produce 3-(4-hydroxyphenyl)-4-methyl-2-(4-{2-[(3R)-3-methylpyrrolidin-1-yl] ethoxy}phenyl)-2H-chromen-7-ol (OP-1038)

(3R)-3-methyl-1-(2-(4-(4-methyl-7-((tetrahydro-2H-pyran-2-yl)oxy)-3-(4-((tetrahydro-2H-pyran-2-yl)oxy)phenyl)-2H-chromen-2-yl)phenoxy)ethyl)pyrrolidine (15.130 g, 24.2 mmol, 1.0 equiv.) was dissolved into 80% acetic acid/water (150 mL). The solution was heated in an oil bath at 90° C. for 1 hour. HPLC analysis of the reaction mixture indicated the reaction was complete. The dark red solution was concentrated to a dark red oil. The oil was suspended into ethyl acetate (600 mL) and washed with saturated NaHCO3 (3×300 mL). The combined aqueous layer was extracted with ethyl acetate (2×100 mL). The combined organic layer was washed with brine (2×200 mL), dried over anhydrous magnesium sulfate, filtered and concentrated to give a red oil (14.03 g, crude). The oil was adsorbed onto silica gel (30 g) and chromatgraphed on silica gel (2×100 g cartridge) with 0-10% MeOH in DCM. Fractions containing the product were pooled and concentrated to give a red colored foam (6.68 g). Impure fractions were concentrated and repurified with the same conditions to give an additional 0.9496 g of red foam which was combined with the previous foam. Total yield 7.6296 g, 69.0%.

Gradient method 0% MeOH/DCM for 5 minutes, gradient to 10% MeOH/DCM over 20 minutes, hold at 10% MeOH/DCM for 10 minutes. TLC conditions (UV and 12): 10% MeOH/DCM 5 spots 0.64, 0.48, (product) 0.31, 0.21, 0.07. HPLC: 100% purity (0-90% acetonitrile/water). LC_MS: [M+1]+=458.3.

Step 8

OP-1038 was separated into its diastereomers (2S)-3-(4-hydroxyphenyl)-4-methyl-2-(4-{2-[(3R)-3-methylpyrrolidin-1-yl]ethoxy}phenyl)-2H-chromen-7-ol (OP-1074) and (2R)-3-(4-hydroxyphenyl)-4-methyl-2-(4-{2-[(3R)-3-methylpyrrolidin-1-yl]ethoxy}phenyl)-2H-chromen-7-ol (OP-1075) using a Diacel, Chiralpak IC column at room temperature in isocratic mode with 80% hexanes, 20% 2-propanol with 0.1% dimethylethylamine or 0.1% diethyl amine as a modifier. This method was used at analytical and preparative scale.

Step 9

Reaction to Produce (R)-2-(benzyloxy)-1-(3-methylpyrrolidin-1-yl)ethanone (R)-3-methylpyrrolidine hydrochloride (20.000 g, 164.5 mmol, 1.0 equiv.) was added to a round bottom flask and dissolved into anhydrous DCM (45 mL). Freshly distilled Diisopropylethylamine (60.157 ml, 345.4 mmol, 2.1 equiv.) and freshly activated 4 Å molecular sieves (~21 g) was added to the solution and stirred for 10 minutes. 2-(Benzyloxy) acetyl chloride (31.881 g, 172.7 mmol, 1.1 equiv.) dissolved into DCM (50 mL) was added to the reaction at room temperature dropwise via syringe over 20 minutes with a room temperature water bath for cooling. After complete addition the reaction was stirred for 17 hours. TLC analysis (1:1, EA/Hex, Rf: 0.83, 0.33, 0.05) showed no presence of acid chloride. The reaction poured into a separatory funnel and the organic layer washed successively with 1 M HCl (2×200 mL), saturated sodium bicarbonate (200 mL) and brine (200 mL). The organic layer was dried over anhydrous MgSO4, filtered and concentrated to an orange oil (42.40 g). The oil was loaded onto silica gel (30 g) and the mixture split into ~18 g portions and chromatographed on silica gel (4×100 g cartridges) with a gradient method 10-80% EA/Hex. Fraction with Rf 0.33 spot were pooled and concentrated to give a yellow oil (34.02 g, 88.7%).

Gradient method: 10% EA/Hex hold 5 minutes, gradient to 80% EA/Hex over 15 minutes, hold at 80% EA/Hex for 10 minutes. Fractions with Rf 0.33 were pooled and concentrated.

Step 10

Reaction to Produce (R)-1-(2-(benzyloxy)ethyl)-3-methylpyrrolidine

Aluminum trichloride (54.513 g, 408.8 mmol, 3.0 equiv.) was dissolved into anhydrous THF (750 mL) and cooled in an ice bath. Lithium aluminum hydride (35.688 g, 940.3 mmol, 6.9 equiv.) was added in small portions via a powder addition funnel to the above suspension over 35 minutes and stirred for an additional 10 minutes. The suspension was cooled to −78° C. for 15 minutes and a solution of (R)-2-(Benzyloxy)-1-(3-methylpyrrolidin-1-yl)ethanone (33.980 g, 136.3 mmol, 1.0 equiv.) in anhydrous THF (150 mL) was added dropwise to the cold suspension via a pressure equalizing addition funnel over 20 minutes. The reaction was kept at −78° C. for 1 hour and stirred at room temperature for 1 hours. The reaction was carefully quenched with 6 N HCl solution (100 mL) and stirred for 17 h to give grey suspension. A solution 6 N NaOH (216 mL) was added to the mixture to give a white suspension after stirring for 30 minutes. The mixture was filtered through a pad of Celite (4 cm). The solids were washed with DCM (5×500 mL). The filtrate was poured into a reparatory funnel and the layers separated (~200 mL aqueous layer recovered). The aqueous layer was extracted with DCM (3×100 mL). The organic layers were combined and washed with brine (500 mL), dried over anhydrous sodium sulfate, filtered and concentrated to a yellow liquid (33.43 g). This liquid was loaded onto silica gel (25 g) and chromatographed through silica gel (2×100 g cartridge) with 50-100% ethyl acetate in hexanes followed by 10-40% methanol in dichloromethane to give a yellow oil (29.17 g, quant).

Gradient method: 50% EA/Hex 4 minutes, gradient to 100% EA over 6 minutes, hold at 100% EA for 5 minutes, Solvent change to 10% MeOH in DCM hold for 0 minutes, gradient to 40% MeOH in DCM over 1 minute, hold at 40% MeOH in DCM for 8 minutes. The fractions were pooled and concentrated to a yellow oil (29.17 g, quant).

Step 11

(R)-1-(2-(benzyloxy)ethyl)-3-methylpyrrolidine (10.000 g, 45.6 mmol, 1.0 equiv.) (0.4822 g; 0.7137 g) was added to a 400 mL Parr flask, methanol (60 mL) was added and the solution cooled in an ice bath for 10 minutes. 20% Pd(OH)$_2$ on Carbon, 50% H2O (6.403 g, 45.6 mmol, 1.0 equiv.) was added to the cooled solution and flushed with nitrogen. Hydrochloric acid (6 M, 7.6 mL) was added to mixture. The flask was pressurized with hydrogen to 30 psi shaken for 1 minute and the hydrogen released. This was repeated twice more and pressurized to 100 psi with hydrogen. This suspension was shaken for 16 hours. A sample was taken and the TLC (10% MeOH in DCM) indicated the reaction was incomplete and additional catalyst (2.0 g) was added to the mixture. The reaction was treated in a similar manner described above and shaken on the hydrogenator for an additional 30 hours. Celite (5 g) was added to the Parr flask and the mixture filtered through a pad of Celite (2 cm). The solid was washed wth methanol (2×250 mL). The filtrate was concentrated on a rotovap to dryness to give a red oil (7.81 g). The oil was taken up in methanol (50 mL) and 25% sodium methoxide in methanol (9.9 mL, 45.5 mmol, 1 equiv) was added to the methanolic solution to give a white suspension. The mixture was concentrated to dryness and taken up into anhydrous DCM (35 mL). The suspension was centrifuged at 3K rpm for 5 minutes. The clear solution was collected and the solid resuspended into DCM (35 mL). This process was repeated a total of 4 times. The combined solution was concentrated to a yellow liquid (5.6341 g, 95.6%).

Following the general method above and using the appropriate reagents and starting materials, OP-1046 and OP-1047 were synthesized.

Synthesis of HCl Salts of OP-1038 and OP-1074

3-(4-hydroxyphenyl)-4-methyl-2-(4-{2-[(3R)-3-methylpyrrolidin-1-yl]ethoxy}phenyl)-2H-chromen-7-ol (OP-1038; 0.020 g, 0.0 mmol, 1.0 equiv.) or (2S)-3-(4-hydroxyphenyl)-4-methyl-2-(4-{2-[(3R)-3-methylpyrrolidin-1-yl]ethoxy}phenyl)-2H-chromen-7-ol (OP-1074; 0.020 g, 0.0 mmol, 1.0 equiv.) (Compound 33) was placed into a 1 dram vial and dissolved into methanol (0.2 mL). 4 M HCl in methanol (200 µL) was added to the solution and stirred for 15 minutes. The yellow solution was concentrated a yellow orange solid (0.022 g and 0.0206 respectively).

Synthesis of OP-1083

OP-1083 was prepared by air oxidation on OP-1074, followed by chromatographic separation of OP-1083 and OP-1074. The mixture of OP-1074 and OP-1083 (560 mg) was dissolved in methanol (15 mL) and mixed with silica gel (3 g). The mixture was dried to give a dark red powder. This powder was loaded into a cartridge and chromatographed on silica gel (4 g cartridge) with 0-25% methanol in dichloromethane to give OP-1074 as an orange solid (0.261 g, 46.6%) and OP-1083 as an orange solid (41.1 mg, 15%)

Method: 0% MeOH for 4 min, gradient to 5% MeOH/DCM over 5 minutes, hold at 5% for 6 minutes, gradient to 10% MeOH/DCM over 2 minutes, hold at 10% MeOH/DCM for 8 minutes, gradient to 25% MeOH/DCM over 0 minutes, hold at 25% for 5 minutes.

Synthesis of OP-1084

(2S)-3-(4-hydroxyphenyl)-4-methyl-2-(4-{2-[(3R)-3-methylpyrrolidin-1-yl]ethoxy}phenyl)-2H-chromen-7-ol (0.020 g, 0.0 mmol, 1.0 equiv.) was added to a 30 mL vial and suspended into anhydrous ethyl acetate (20 mL). Diisopropylethylamine (19 ul, 0.1 mmol, 2.5 equiv.) was added to the suspension and the solution was cooled in an ice bath for 5 minutes. Ethyl chloroformate (10 ul, 0.1 mmol, 2.3 equiv.) was added to the reaction via a gas tight syringe. The reaction immediately became a cloudy white suspension. The reaction was removed from the ice bath and stirred at room temperature for 16 h. The reaction was concentrated to dryness and dissolved into a minimum of DCM to load onto a 4 g silica gel cartridge. The crude material was eluted with 0-15% MeOH/DCM to give the desired product as a pale yellow film (0.006.8 g, 27%).

TLC (5% MeOH/DCM): 4 spots, 0.84, 0.42, 0.26 (Product), 0.16 (Mono carbonate). Gradient method: 0% MeOH/DCM hold for 2 minutes, gradient to 5% MeOH/DCM over 5 minutes, hold at 5% MeOH/DCM for 3 minutes, gradient to 15% MeOH/DCM over 3 minutes, hold at 15% MeOH/DCM for 2 minutes. Fractions 16-19 pooled: 6.8 mg LCMS (m/z): 602; HPLC (254 nm): 95.65%.

Synthesis of OP-1085

(2S)-3-(4-hydroxyphenyl)-4-methyl-2-(4-{2-[(3R)-3-methylpyrrolidin-1-yl]ethoxy}phenyl)-2H-chromen-7-ol (0.035 g, 0.1 mmol, 1.0 equiv.) was added to a dry 1 dram vial equipped with a stir bar under a stream of N2. The vial was sealed with a septum and freshly distilled Pyridine (400 ul, 5.0 mmol, 113.6 equiv.) was added to the vial via syringe to give pink red solution. The vial was cooled in a 0° C. ice/water bath for 10 minutes and Trimethylacetyl Chloride (100 ul, 0.8 mmol, 10.6 equiv.) was added via a GC syringe in one portion to the solution. The solution immediately became a light yellow color and was stirred for 30 minutes at 0° C. The reaction was allowed to reach room temperature over 30 min and stirred at room temperature for 1 h. A sample was analyzed by LCMS to show the presence of a mixture of mono ester and diester. The reaction mixture was concentrated to dryness and dissolved into a minimum amount of DCM and chromatographed on silica gel (4 g cartridge) with 0-25 MeOH/DCM. The fractions containing product were pooled and concentrated to a give a pale yellow film (9.2 mg, 33%).

Gradient: 0% MeOH/DCM for 2 minutes, gradient to 2.5% MeOH/DCM over 4 minutes, hold at 2.5% MeOH/DCM for 5 minutes, gradient to 10% MeOH/DCM over 1 minute, hold at 10% MeOH/DCM for 4 minutes, gradient to 25% MeOH/DCM over 2 minutes, hold at 25% for 7 minutes. Fractions 11-17 and 19-28 pooled. LCMS (m/z): M+1, 626; HPLC (254 nm): 98.0%.

Synthesis of OP-1086 and OP-1088

Pyridine (2000 ul, 24.8 mmol, 113.6 equiv.) was added to a dry 1 dram vial with a stir bar. The vial was cooled in a −15° C. dry ice methanol/water bath. Phosphorus oxychloride (71 ul, 0.8 mmol, 3.5 equiv.) was added via a GC syringe in one portion to the solution. The solution was stirred for 5 minutes then the solid 3-(4-hydroxyphenyl)-4-methyl-2-(4-{2-[(3R)-3-methylpyrrolidin-1-yl]ethoxy}phenyl)-2H-chromen-7-ol (OP-1038; 0.100 g, 0.2 mmol, 1.0 equiv.) or (2S)-3-(4-hydroxyphenyl)-4-methyl-2-(4-{2-[(3R)-3-methylpyrrolidin-1-yl]ethoxy}phenyl)-2H-chromen-7-ol (OP-1074; 0.100 g, 0.2 mmol, 1.0 equiv.) was added in one portion under a stream of N2. The reaction stirred at this temperature for 1.5 h. The solution became slurry after ~45 minutes. The reaction was allowed to reach room temperature over 45 min and stirred at room temperature for 2 h. A sample was quenched with water and analysis showed the mass of the desired product. The reaction mixture was concentrated to dryness. The crude mixture was suspended into 2 N HCl (5 mL). The suspension was sonicated and centrifuged at 5000 rpm for 6 minutes. The supernatant was decanted and the solid resuspended into 5 mL of 2 N HCl and the process was repeated. The solid was dried under vacuum to give 129 mg of the crude product. The solid was suspended into water (2 mL) and 6 N sodium hydroxide solution (174 μL, 1 mmol, 5 equiv) was added to give an orange solution. This was purified by Preparative LC with acetonitrile and water to give the product as a tan solid.

Synthesis of OP-1087

(2S)-3-(4-hydroxyphenyl)-4-methyl-2-(4-{2-[(3R)-3-methylpyrrolidin-1-yl]ethoxy}phenyl)-2H-chromen-7-ol (0.020 g, 0.0 mmol, 1.0 equiv.) was added to a 30 mL vial and suspended into anhydrous ethyl acetate (20 mL). Diisopropylethylamine (19 ul, 0.1 mmol, 2.5 equiv.) was added to the suspension and the solution was cooled in an ice bath for 5 minutes. Methyl chloroformate (7 ul, 0.1 mmol, 2.2 equiv.) was added to the reaction via a gas tight syringe. The reaction immediately became a cloudy white suspension. The reaction was removed from the ice bath and stirred at room temperature for 16 h. The reaction was concentrated to dryness and dissolved into a minimum of DCM to load onto a 4 g silica gel cartridge. The crude material was eluted with 0-15% MeOH/DCM to give the desired product as a pale yellow film (0.0096 g, 40%).

TLC (5% MeOH/DCM): 4 spots, 0.95, 0.55, 0.38 (Product), 0.25 (Mono carbonate).

Gradient method: 0% MeOH/DCM hold for 2 minutes, gradient to 5% MeOH/DCM over 5 minutes, hold at 5% MeOH/DCM for 3 minutes, gradient to 15% MeOH/DCM over 3 minutes, hold at 15% MeOH/DCM for 2 minutes. Fractions 11-15 pooled: 9.6 mg. LCMS (m/z): 574; HPLC (254 nm): 95.08%.

Exemplary Compounds of the Invention

Figure 1A:
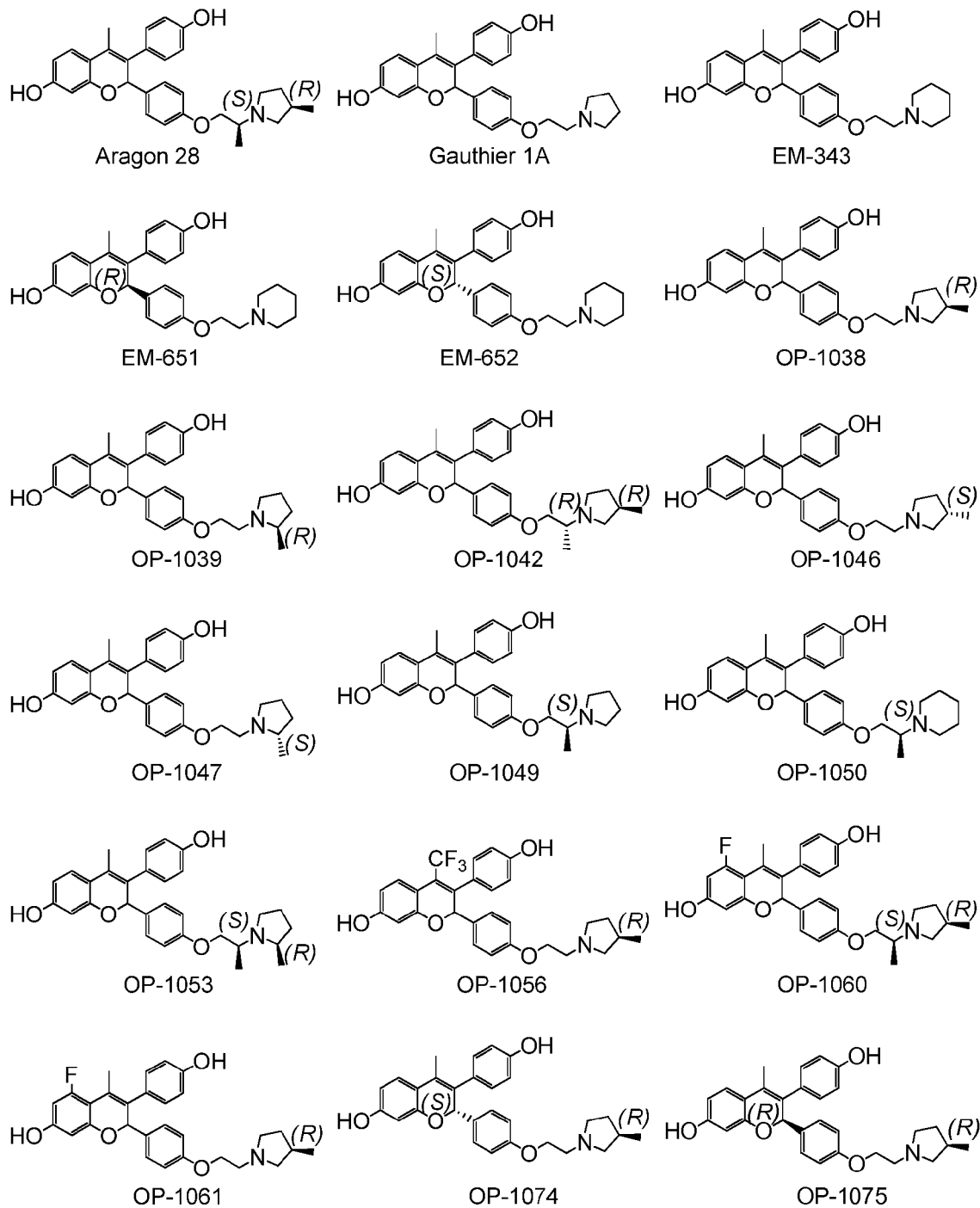
FIG. 1. Representative compounds of the present invention (FIG. 1A) as well as representative prodrugs and salts of OP-1038 and OP-1074 (FIG. 1B). The IUPAC names of the compounds are.
Figure 1B:
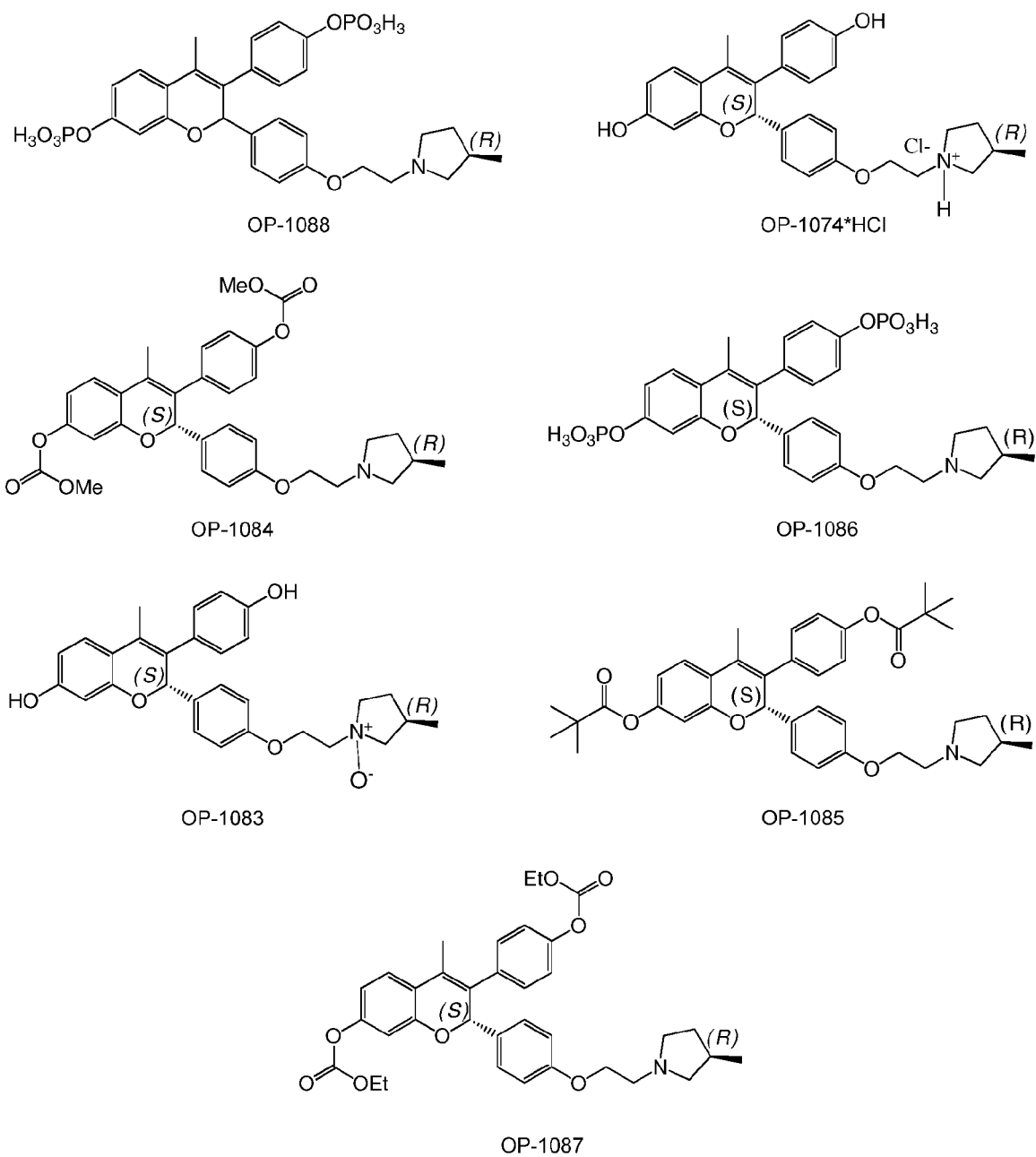

FIGS. 1A and 1B depicts the structure of compounds, with stereochemistry as defined herein, which have been or can be prepared according to the synthetic methods described herein. FIG. 1A also shows the structure of representative reference compounds used for comparison, including Aragon 28 (Example 28 of WO2011/156518); Gauthier 1A (Gauthier et al. "Synthesis and structure-activity relationships of analogs of EM-652(acolbifene), a pure selective estrogen receptor modulator. Study of nitrogen substitution" Journal of Enzyme Inhibition and Medicinal Chemistry, 2005; 20(2): 165-177); EM-343, EM-651 and EM-652 (Acolbifene). FIG. 1B depicts representative prodrugs and salts of OP-1038 and OP-1074.

Assays

Compounds provided herein can be evaluated using various in vitro and in vivo assays; examples of which are described below.

The following biological examples are offered to illustrate the compounds, pharmaceutical compositions and methods provided herein and are not to be construed in any way as limiting the scope thereof.

Figure 6A:
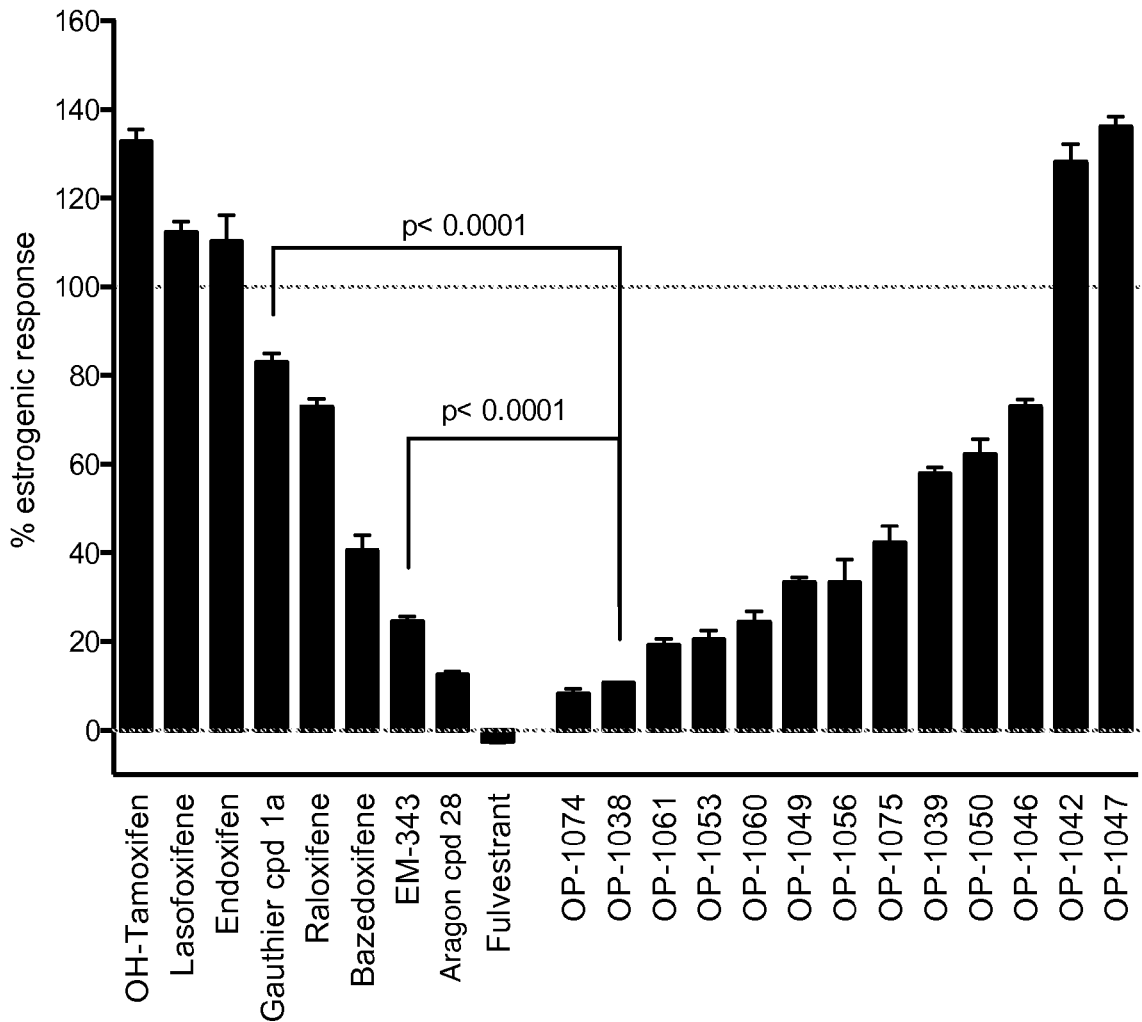
Figure 6B:
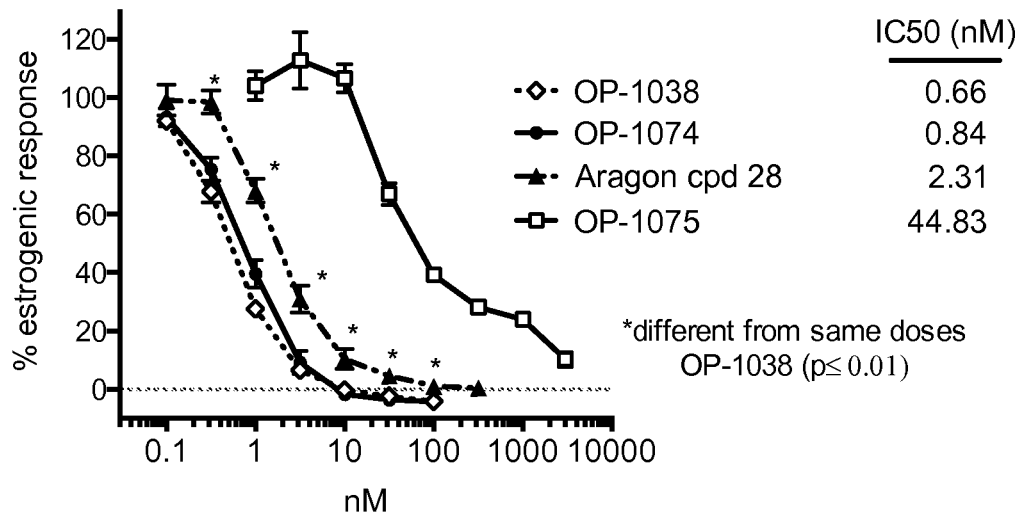
Figure 6C:
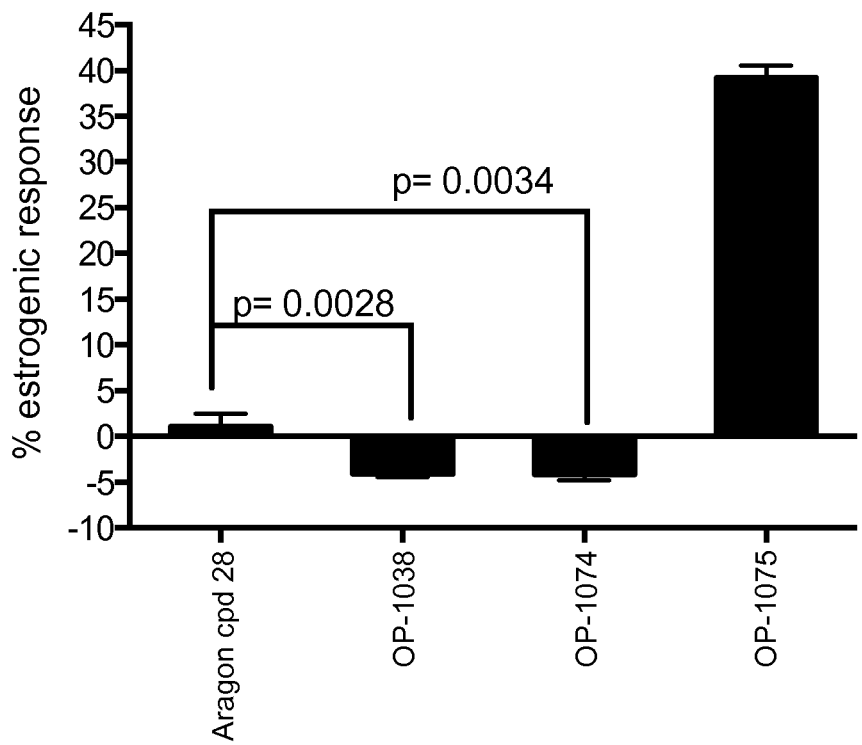

Demonstration of the Superiority of OP-1038 and OP-1074 Using Sensitive In Vitro Estrogenicity Assays Method for performing the alkaline phosphatase (AP) assay. ECC-1 cells (American Type Culture Collection, Manassus, Va.) were maintained in RPMI medium plus 10% fetal bovine serum at 37° C. At the beginning of the assay trypsinized cells were resuspended in RPMI medium plus 5% charcoal dextran stripped serum (CDSS, (Hyclone, Logan, Utah)) and plated at a density of 25-50 k cells per well into a 96-well plate for at least 6 hours. Compounds were diluted in serum-free medium and added 1:1 to plated cells in replicate wells (2.5% CDSS final). Plates were incubated for 3 days at 37° C. and subsequently frozen at −80° C. to lyse cells after removing the medium. Thawed plates were incubated with a chromogenic substrate of AP, p-nitrophenyl phosphate (Invitrogen, Grand Island, N.Y.), for 40 minutes at 40° C. Absorbance was read at 405 nm using a plate spectophotometer. This assay is shown to correlate with the in vivo studies comparing uterine wet weight in ovariectomized rats following treatment with a number of anti-estrogens as shown in FIG. 2. This AP assay is used herein for a number of studies as described in FIGS. 3 through 8. Specifically, FIG. 3 demonstrates that OP-1038 and OP-1074 lack estrogenic activity in the alkaline phosphatase assay in ECC1 cells as compared to a number of other anti-estrogens. FIG. 4 demonstrates that OP-1038 is less estrogenic than the Aragon Compound 28 at a number of doses tested in the AP assay. FIG. 5 demonstrates that OP-1038 lacks estrogenic activity in the AP assay, in contrast to other mono-methyl substituted pyrrolidines. FIG. 6A demonstrates that OP-1038 and OP-1074 inhibit estrogen-stimulated AP in ECC-1 cells. FIGS. 6B and 6C demonstrates that OP-1038 is more potent than Aragon Cpd. 28 in inhibition of E2-stimulated AP activity in ECC-1 cells. FIG. 7 demonstrates that OP-1038 is more potent than EM-652 in the AP assay in ECC-1 cells. In vivo activity comparing uterine wet weight in ovariectomized rats was then confirmed for OP-1038 and OP-1074 as shown in FIG. 9.

Compounds of invention are tested for their inhibitory activity of estrogen according to the assay methods described in Hodges-Gallagher, L., Valentine, C. V., El Bader, S. and Kushner, P. J. (2007) "Histone Deacetylase Inhibitors Enhance the Efficacy of Hormonal Therapy Agents on Breast Cancer Cells and Blocks Anti-estrogen-Driven Uterine Cell Proliferation" Breast Cancer Res Treat, November; 105(3): 297-309. Specifically, an estrogen-responsive reporter gene (ERE-tk109-Luc) was transiently transfected into MCF-7 cells and treated with anti-estrogens in triplicate in the presence of 100 pM 17β-estradiol (E2) for 18-22 hours. Luciferase activity was normalized to activity of E2 alone and IC50's were calculated using the least squares fit method. This method is also described in legend for FIG. 10. OP-1038 and OP-1074 are potent antagonists of estrogen-stimulated ERE-regulated reporter gene activity. OP-1038 and OP-1074 have improved potency for inhibition of E2 induced transcription compared to tamoxifen, EM-343 and raloxifene.

Proliferation in MCF-7 was measured using a fluorescent DNA binding dye 6-8 days after treatment in triplicate with anti-estrogens in the presence of 100 pM E2 and as described in the legend to, and depicted in FIG. 11. OP-1038 and OP-1074 are potent antagonists of estrogen in MCF-7 cells. OP-1038 and OP-1074 have improved potency for inhibition of E2 stimulated proliferation over tamoxifen, EM-343, and raloxifene.

ERα expression was detected in MCF-7 cell lysates treated with 100 nM anti-estrogens in serum-free medium for 22-24 hours and immunoblotted with an antibody specific to ERα as described in the legend to, and depicted in FIG. 12. OP-1074 and OP-1038 induce degradation of estrogen receptor-alpha in human breast and endometrial cells in a manner comparable to fulvestrant.

OP-1038 and OP-1074 inhibit E2 induced transcription, E2 stimulated proliferation and they induce degradation of the estrogen receptor-alpha in a manner comparable to Aragon Compound 28.

Mammary Tumor Xenograft Study

The purpose of this study is to examine the ability of OP-1074, to slow or shrink a tamoxifen resistant tumor (MCF-7 HER2/neu Clone 18) xenograft growing on ovariectomized athymic nude mice under stimulation from exogenous estrogen. Clone 18 cells grown in culture are implanted along with 0.18 mg estradiol/90 day release pellets (Innovative Research, Sarasota Fla.) into 55 mice to initiate the experiment. When the tumors have reached 250 cubic millimeters the mice are divided into four groups of 10 mice each and dosing initiated. The four groups are:

1) No hormonal treatment—this group receives daily gavage with vehicle.

2) Tamoxifen citrate 100 mg/kg daily by oral gavage in vehicle.

3) Faslodex 100 mg/kg delivered daily by subcutaneous injection.

4) OP-1074 100 mg/kg twice daily by oral gavage in vehicle with the exception of two weekends in which dosing was once daily.

Figure 13A:
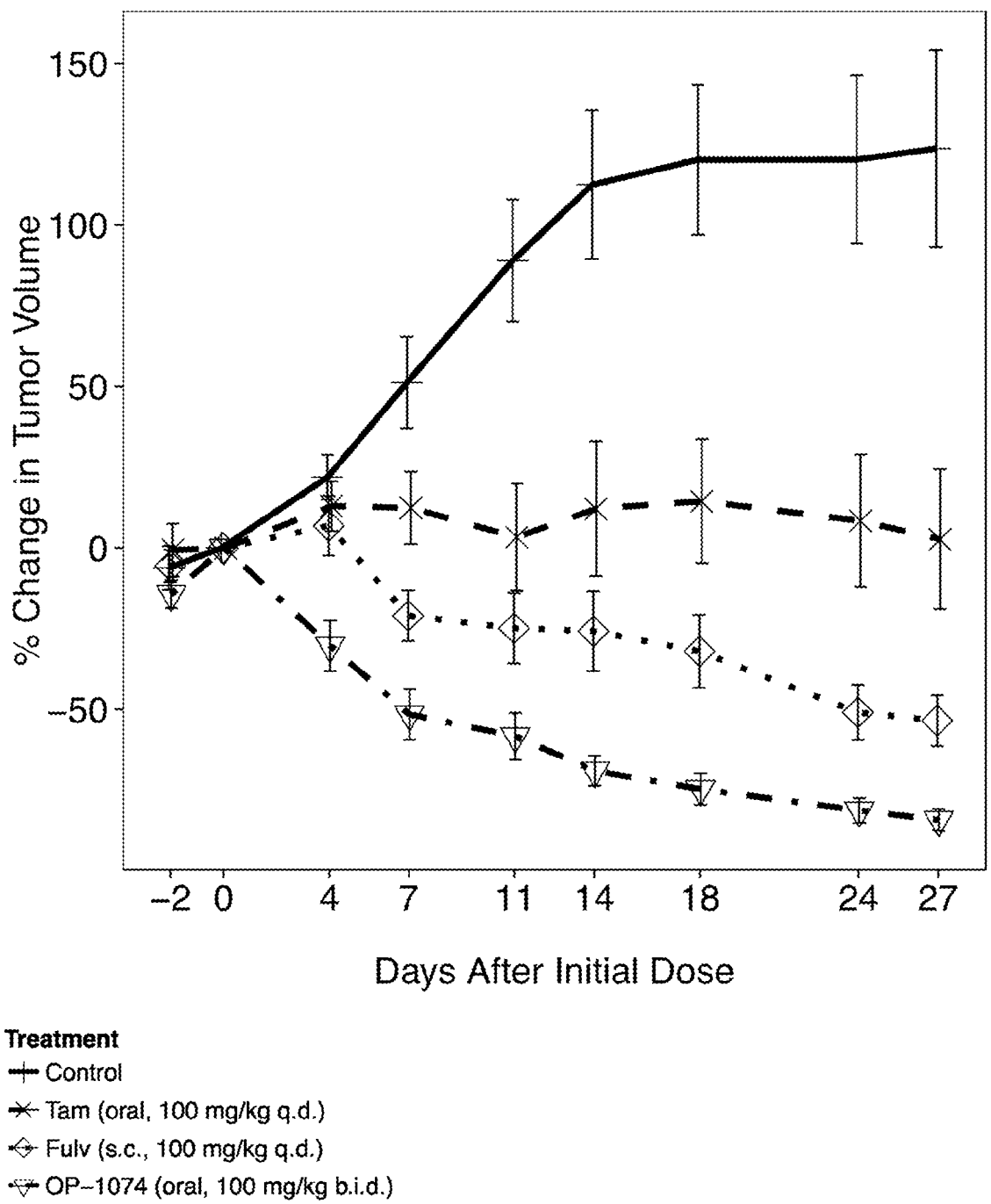
Figure 13B:
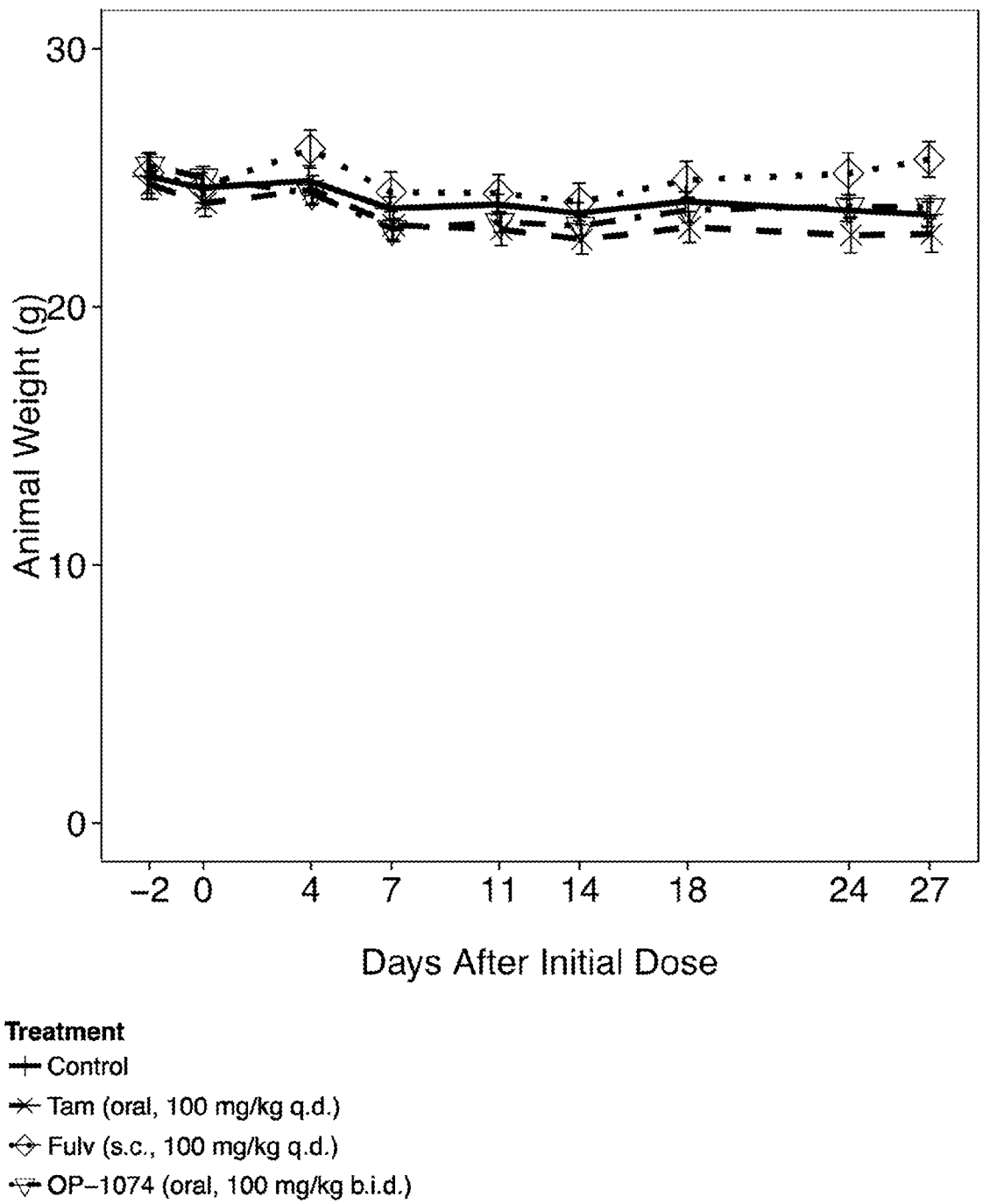
Figure 13C:
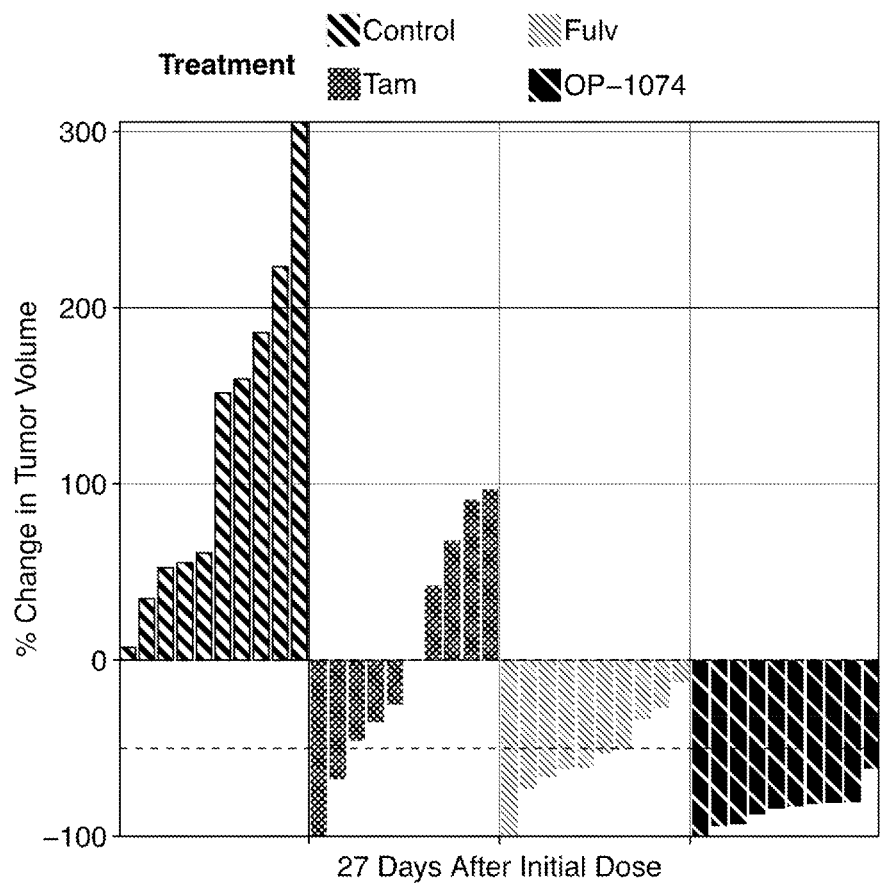

Results are shown in FIGS. 13A, 13B and 13C. OP-1074 induces rapid and complete regression of MCF-7 Clone 18 HER2/neu xenografts growing on nude mice stimulated by estrogen.

Single Dose Oral Pharmacokinetics Study in Female Rats

The oral bioavailabilty in rats of OP-1038 was determined in the following study. 3 rats (female Sprague Dawley, non-fasted) were dosed by oral gavage (5 mg/kg body weight) in 0.5% CMC in water with a comparison to intravenous dosing (3 mg/kg body weight). Plasma was collected at the following hourly time points from rats in both groups (0, 0.08, 1.0, 2.0, 4.0, 8.0, 16.0, 24.0, 48.0 and 96.0 hours post dosing). Plasma concentrations of OP-1038 were determined by HPLC. The results are shown in Table 2 below. OP-1038 is shown to be orally bioavailable.

TABLE 2

PK data for OP-1038
Single Dose Oral Pharmacokinetics Study
in Female S.D. Rats

| Parameters | OP-1038 |
|---|---|
| Route of administration | Oral |
| Dose (mg/kg) | 5.00 |
| $C_{max}$ (ng/mL) | 24.8 ± 3.00 |
| $T_{max}$ (h) | 2.33 ± 1.53 |
| $AUC_{last}$ (h*ng/mL) (0 to 96 h) | 603 ± 46.7 |
| $AUC_{inf}$ (h*ng/mL) | 671 ± 44.8 |
| AUCextrap (%) | 10.1 ± 6.26 |
| $T_{1/2}$ (h) | 28.5 ± 11.6 |
| $MRT_{last}$ | 25.9 ± 3.37 |
| $V_{ss}$ (L/kg) | — |
| CL (mL/min/kg) | — |
| F % (Oral bioavailability) | 18.9% |

DEFINITIONS

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); and Wilen, *Tables of Resolving Agents and Optical Resolutions* p. 268 (E. L. Eliel, Ed., Univ. of Notre Dame Press, Notre Dame, Ind. 1972). Unless otherwise stated, the invention encompasses compounds described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The articles "a" and "an" may be used herein to refer to one or to more than one (i.e. at least one) of the grammatical objects of the article. By way of example "an analogue" means one analogue or more than one analogue.

"Alkyl" refers to a radical of a straight-chain or branched saturated hydrocarbon group which in one embodiment has from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_1$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl.

"Alkylene" refers to a substituted or unsubstituted alkyl group, as defined above, wherein two hydrogens are removed to provide a divalent radical. Exemplary divalent alkylene groups include, but are not limited to, methylene (—$CH_2$—), ethylene (—$CH_2CH_2$—), the propylene isomers (e.g., —$CH_2CH_2CH_2$— and —$CH(CH_3)CH_2$—) and the like.

"Alkenyl" refers to a radical of a straight-chain or branched hydrocarbon group which in one embodiment has from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkenylene" refers a substituted or unsubstituted alkenyl group, as defined above, wherein two hydrogens are removed to provide a divalent radical. Exemplary divalent alkenylene groups include, but are not limited to, ethenylene (—CH=CH—), propenylenes (e.g., —CH=CHCH$_2$— and —C(CH$_3$)=CH— and —CH=C(CH$_3$)—) and the like.

"Alkynyl" refers to a radical of a straight-chain or branched hydrocarbon group which in one embodiment has from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Alkynylene" refers a substituted or unsubstituted alkynyl group, as defined above, wherein two hydrogens are removed to provide a divalent radical. Exemplary divalent alkynylene groups include, but are not limited to, ethynylene, propynylene, and the like.

Naturally occurring or non-naturally occurring "amino acids" can be used in the preparation of compounds of the invention as described herein. For example, natural amino acids include valine, leucine, isoleucine, methionine, phenylalanine, asparagine, glutamic acid, glutamine, histidine, lysine, arginine, aspartic acid, glycine, alanine, serine, threonine, tyrosine, tryptophan, cysteine, proline, 4-hydroxyproline, g-carboxyglutamic acid, selenocysteine, desmosine, 6-N-methyllysine, e-N,N,N-trimethyllysine, 3-methylhistidine, O-phosphoserine, 5-hydroxylysine, e-N-acetyllysine, s-N-methylarginine, N-acetylserine, g-aminobutyric acid, citrulline, ornithine, azaserine, homocysteine, b-cyanoalanine and S-adenosylmethionine. Non-limiting examples of non-naturally occurring amino acids include phenyl glycine, meta-tyrosine, para-amino phenylalanine, 3-(3-pyridyl)-L-alanine, 4-(trifluoromethyl)-D-phenylalanine, and the like. In one embodiment, an L-amino acid is used.

"Aryl" refers to a radical of a monocyclic or polycyclic (e.g., bicyclic or tricyclic) 4n+2 aromatic ring system (e.g., having 6, 10, or 14 it electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following:

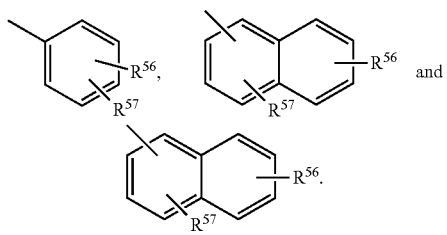

In these Formula one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$ haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

"Fused aryl" refers to an aryl having two of its ring carbon in common with a second aryl ring or with an aliphatic ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 it electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

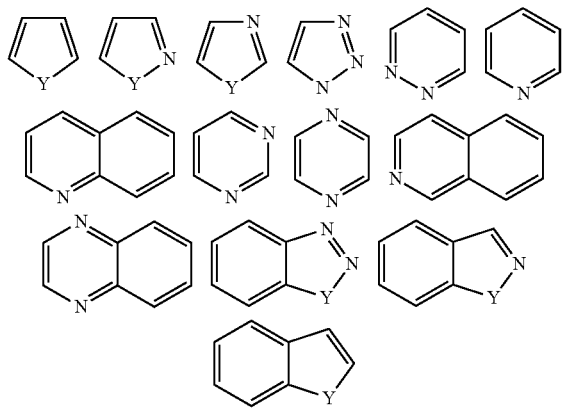

wherein each Y is selected from carbonyl, N, NR$^{65}$, O, and S; and R$^{65}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

Examples of representative aryl having hetero atoms containing substitution include the following:

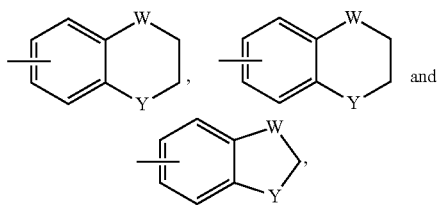

wherein each W is selected from C(R$^{66}$)$_2$, NR$^{66}$, O, and S; and each Y is selected from carbonyl, NR$^{66}$, O and S; and R$^{66}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thioranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

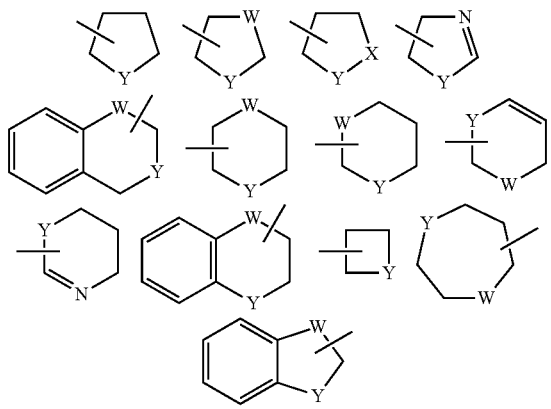

wherein each W is selected from $CR^{67}$, $C(R^{67})_2$, $NR^{67}$, O, and S; and each Y is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, 5-10 membered heteroaryl. These heterocyclyl rings may be optionally substituted with one or more substituents selected from the group consisting of the group consisting of acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(═O)CH$_3$), cyclohexylcarbonyl, cyclohexylmethylcarbonyl, benzoyl (—C (=O)Ph), benzylcarbonyl (—C(=O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocyclyl), wherein t is an integer from 0 to 4. In certain embodiments, R$^{21}$ is C$_1$-C$_8$ alkyl, substituted with halo or hydroxy; or C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Acylamino" refers to a radical —NR$^{22}$C(O)R$^{23}$, where each instance of R$^{22}$ and R23 is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein, or R$^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —NR$^{24}$C(O)—C$_1$-C$_8$ alkyl, —NR$^{24}$C(O)—(CH$_2$)$_t$(C$_6$-C$_{10}$ aryl), —NR$^{24}$C(O)—(CH$_2$)$_t$(5-10 membered heteroaryl), —NR$^{24}$C(O)—(CH$_2$)$_t$(C$_3$-C$_{10}$ cycloalkyl), and —NR$^{24}$C(O)—(CH$_2$)$_t$(4-10 membered heterocyclyl), wherein t is an integer from 0 to 4, and each R$^{24}$ independently represents H or C$_1$-C$_8$ alkyl. In certain embodiments, R$^{25}$ is H, C$_1$-C$_8$ alkyl, substituted with halo or hydroxy; C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; and R$^{26}$ is H, C$_1$-C$_8$ alkyl, substituted with halo or hydroxy; C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxyl; provided at least one of R$^{25}$ and R$^{26}$ is other than H.

"Acyloxy" refers to a radical —OC(O)R$^{27}$, where R$^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl and benzylcarbonyl. In certain embodiments, R$^{28}$ is C$_1$-C$_8$ alkyl, substituted with halo or hydroxy; C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Alkoxy" refers to the group —OR$^{29}$ where R$^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, R$^{29}$ is a group that has 1 or more substituents, for instance from 1 to 5 substituents, and particularly from 1 to 3 substituents, in particular 1 substituent, selected from the group consisting of amino, substituted amino, C$_6$-C$_{10}$ aryl, aryloxy, carboxyl, cyano, C$_3$-C$_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N(R$^{38}$)$_2$ wherein R$^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of R$^{38}$ is not a hydrogen. In certain embodiments, each R$^{38}$ is independently selected from: hydrogen, C$_1$-C$_8$ alkyl, C$_3$-C$_8$ alkenyl, C$_3$-C$_8$ alkynyl, C$_6$-C$_{10}$ aryl, 5-10 membered heteroaryl, 4-10 membered heterocyclyl, or C$_3$-C$_{10}$ cycloalkyl; or C$_1$-C$_8$ alkyl, substituted with halo or hydroxy; C$_3$-C$_8$ alkenyl, substituted with halo or hydroxy; C$_3$-C$_8$ alkynyl, substituted with halo or hydroxy, or —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), or —(CH$_2$)$_t$(4-10 membered heterocyclyl), wherein t is an integer between 0 and 8, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; or both R$^{38}$ groups are joined to form an alkylene group.

Exemplary 'substituted amino' groups are —NR$^{39}$—C$_1$-C$_8$ alkyl, —NR$^{39}$—(CH$_2$)$_t$(C$_6$-C$_{10}$ aryl), —NR$^{39}$—(CH$_2$)$_t$(5-10 membered heteroaryl), —NR$^{39}$—(CH$_2$)$_t$(C$_3$-C$_{10}$ cycloalkyl), and —NR$^{39}$—(CH$_2$)$_t$(4-10 membered heterocyclyl), wherein t is an integer from 0 to 4, for instance 1 or 2, each R$^{39}$ independently represents H or C$_1$-C$_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —$N_3$.

"Carbamoyl" or "amido" refers to the radical —$C(O)NH_2$.

"Substituted carbamoyl" or "substituted amido" refers to the radical —$C(O)N(R^{62})_2$ wherein each $R^{62}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{62}$ is not a hydrogen. In certain embodiments, $R^{62}$ is selected from H, $C_1$-$C_8$ alkyl, $C_3$-$C_{10}$ cycloalkyl, 4-10 membered heterocyclyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered heterocyclyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{62}$ is other than H.

Exemplary 'substituted carbamoyl' groups include, but are not limited to, —$C(O)NR^{64}$—$C_1$-$C_8$ alkyl, —$C(O)NR^{64}$—$(CH_2)_t(C_6$-$C_{10}$ aryl), —$C(O)N^{64}$—$(CH_2)_t$(5-10 membered heteroaryl), —$C(O)NR^{64}$—$(CH_2)_t(C_3$-$C_{10}$ cycloalkyl), and —$C(O)NR^{64}$—$(CH_2)_t$(4-10 membered heterocyclyl), wherein t is an integer from 0 to 4, each $R^{64}$ independently represents H or $C_1$-$C_8$ alkyl and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Carboxy' refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro. In further embodiments, the halo group is iodo.

"Hydroxy" refers to the radical —OH.

"Nitro" refers to the radical —$NO_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Cycloalkenyl" refers to substituted or unsubstituted carbocyclyl group having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Fused cycloalkenyl" refers to a cycloalkenyl having two of its ring carbon atoms in common with a second aliphatic or aromatic ring and having its olefinic unsaturation located to impart aromaticity to the cycloalkenyl ring.

"Ethenyl" refers to substituted or unsubstituted —(C=C)—.

"Ethylene" refers to substituted or unsubstituted —(C—C)—.

"Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Thioketo" refers to the group =S.

Exemplary carbon atom substituents include, but are not limited to, halogen, —CN, —$NO_2$, —N3, —$SO_2$H, —$SO_3$H, —OH, —ORaa, —ON(Rbb)2, —N(Rbb)2, —N(Rbb)3+X—, —N(ORcc)Rbb, —SH, —SRaa, —SSRcc, —C(=O)Raa, —$CO_2$H, —CHO, —C(ORcc)2, —$CO_2$Raa, —OC(=O)Raa, —$OCO_2$Raa, —C(=O)N(Rbb)2, —OC(=O)N(Rbb)2, —NRbbC(=O)Raa, —NRbbCO2Raa, —NRbbC(=O)N(Rbb)2, —C(=NRbb)Raa, —C(=NRbb)ORaa, —OC(=NRbb)Raa, —OC(=NRbb)ORaa, —C(=NRbb)N(Rbb)2, —OC(=NRbb)N(Rbb)2, —NRbbC(=NRbb)N(Rbb)2, —C(=O)NRbbSO2Raa, —NRbbSO2Raa, —SO2N(Rbb)2, —SO2Raa, —SO2ORaa, —OSO2Raa, —S(=O)Raa, —OS(=O)Raa, —Si(Raa)3, —OSi(Raa)3-C(=S)N(Rbb)2, —C(=O)SRaa, —C(=S)SRaa, —SC(=S)SRaa, —SC(=O)SRaa, —OC(=O)SRaa, —SC(=O)ORaa, —SC(=O)Raa, —P(=O)2Raa, —OP(=O)2Raa, —P(=O)(Raa)2, —OP(=O)(Raa)2, —OP(=O)(ORcc)2, —P(=O)2N(Rbb)2, —OP(=O)2N(Rbb)2, —P(=O)(NRbb)2, —OP(=O)(NRbb)2, —NRbbP(=O)(ORcc)2, —NRbbP(=O)(NRbb)2, —P(Rcc)2, —P(Rcc)3, —OP(Rcc)2, —OP(Rcc)3, —B(Raa)2, —B(ORcc)2, —BRaa(ORcc), C1-10 alkyl, C1-10 perhaloalkyl, C2-10 alkenyl, C2-10 alkynyl, C3-10 carbocyclyl, 3-14 membered heterocyclyl, C6-14 aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 Rdd groups; or two geminal hydrogens on a carbon atom are replaced with the group =O, =S, =NN(Rbb)2, =NNRbbC(=O)Raa, =NNRbbC(=O)ORaa, =NNRbbS(=O)2Raa, =NRbb, or =NORcc;

each instance of Raa is, independently, selected from C1-10 alkyl, C1-10 perhaloalkyl, C2-10 alkenyl, C2-10 alkynyl, C3-10 carbocyclyl, 3-14 membered heterocyclyl, C6-14 aryl, and 5-14 membered heteroaryl, or two Raa groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups;

each instance of Rbb is, independently, selected from hydrogen, —OH, —ORaa, —N(Rcc)2, —CN, —C(=O)Raa, —C(=O)N(Rcc)2, —CO2Raa, —SO2Raa, —C(=NRcc)ORaa, —C(=NRcc)N(Rcc)2, —SO2N(Rcc)2, —SO2Rcc, —SO2ORcc, —SORaa, —C(=S)N(Rcc)2, —C(=O)SRcc, —C(=S)SRcc, —P(=O)2Raa, —P(=O)(Raa)2, —P(=O)2N(Rcc)2, —P(=O)(NRcc)2, C1-10 alkyl, C1-10 perhaloalkyl, C2-10 alkenyl, C2-10 alkynyl, C3-10 carbocyclyl, 3-14 membered heterocyclyl, C6-14 aryl, and 5-14 membered heteroaryl, or two Rbb groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups;

each instance of Rcc is, independently, selected from hydrogen, $C_1$-10 alkyl, C1-10 perhaloalkyl, C2-10 alkenyl, C2-10 alkynyl, C3-10 carbocyclyl, 3-14 membered heterocyclyl, C6-14 aryl, and 5-14 membered heteroaryl, or two Rcc groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups;

each instance of Rdd is, independently, selected from halogen, —CN, —NO2, —N3, —SO2H, —SO3H, —OH, —ORee, —ON(Rff)2, —N(Rff)2, —N(Rff)3+X—, —N(ORee)Rff, —SH, —SRee, —SSRee, —C(=O)Ree, —CO2H, —CO2Ree, —OC(=O)Ree, —OCO2Ree, —C(=O)N(Rff)2, —OC(=O)N(Rff)2, —NRffC(=O)Ree, —NRffCO2Ree, —NRffC(=O)N(Rff)2, —C(=NR-MORee, —OC(=NRff)Ree, —OC(=NRff)ORee, —C(=NRff)N(Rff)2, —OC(=NRff)N(Rff)2, —NRffC(=NRff)N(Rff)2, —NRffSO2Ree, —SO2N(Rff)2, —SO2Ree, —SO2ORee, —OSO2Ree, —S(=O)Ree, —Si(Ree)3, —OSi(Ree)3, —C(=S)N(Rff)2, —C(=O)SRee, —C(=S)SRee, —SC(=S)SRee, —P(=O)2Ree, —P(=O)(Ree)2, —OP(=O)(Ree)2, —OP(=O)(ORee)2, C1-6 alkyl, C1-6 perhaloalkyl, C2-6 alkenyl, C2-6 alkynyl, C3-10 carbocyclyl, 3-10 membered heterocyclyl, C6-10 aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 Rgg groups, or two geminal Rdd substituents can be joined to form =O or =S;

each instance of Ree is, independently, selected from C1-6 alkyl, C1-6 perhaloalkyl, C2-6 alkenyl, C2-6 alkynyl, C3-10 carbocyclyl, C6-10 aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 Rgg groups;

each instance of Rff is, independently, selected from hydrogen, C1-6 alkyl, C1-6 perhaloalkyl, C2-6 alkenyl, C2-6 alkynyl, C3-10 carbocyclyl, 3-10 membered heterocyclyl, C6-10 aryl and 5-10 membered heteroaryl, or two Rff groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rgg groups; and each instance of Rgg is, independently, halogen, —CN, —NO$_2$, —N3, —SO2H, —SO3H, —OH, —OC1-6 alkyl, —ON(C1-6 alkyl)2, —N(C1-6 alkyl)2, —N(C1-6 alkyl)3+X—, —NH(C1-6 alkyl)2+X—, —NH2(C1-6 alkyl)+X—, —NH3+X—, —N(OC1-6 alkyl)(C1-6 alkyl), —N(OH)(C1-6 alkyl), —NH(OH), —SH, —SC1-6 alkyl, —SS(C1-6 alkyl), —C(=O)(C1-6 alkyl), —CO2H, —CO2(C1-6 alkyl), —OC(=O)(C1-6 alkyl), —OCO2(C1-6 alkyl), —C(=O)NH2, —C(=O)N(C1-6 alkyl)2, —OC(=O)NH(C1-6 alkyl), —NHC(=O)(C1-6 alkyl), —N(C1-6 alkyl)C(=O)(C1-6 alkyl), —NHCO2(C1-6 alkyl), —NHC(=O)N(C1-6 alkyl)2, —NHC(=O)NH(C1-6 alkyl), —NHC(=O)NH2, —C(=NH)O(C1-6 alkyl), —OC(=NH)(C1-6 alkyl), —OC(=NH)OC1-6 alkyl, —C(=NH)N(C1-6 alkyl)2, —C(=NH)NH(C1-6 alkyl), —C(=NH)NH2, —OC(=NH)N(C1-6 alkyl)2, —OC(NH)NH(C1-6 alkyl), —OC(NH)NH2, —NHC(NH)N(C1-6 alkyl)2, —NHC(=NH)NH2, —NHSO2(C1-6 alkyl), —SO2N(C1-6 alkyl)2, —SO2NH(C1-6 alkyl), —SO2NH2, —SO2C1-6 alkyl, —SO2OC1-6 alkyl, —OSOC1-6 alkyl, —SOC1-6 alkyl, —Si(C1-6 alkyl)3, —OSi(C1-6 alkyl)3 -C(=S)N(C1-6 alkyl)2, C(=S)NH(C1-6 alkyl), C(=S)NH2, —C(=O)S(C1-6 alkyl), —C(=S)SC1-6 alkyl, —SC(=S)SC1-6 alkyl, —P(=O)2(C1-6 alkyl), —P(=O)(C1-6 alkyl)2, —OP(=O)(C1-6 alkyl)2, —OP(=O)(OC1-6 alkyl)2, C1-6 alkyl, C1-6 perhaloalkyl, C2-6 alkenyl, C2-6 alkynyl, C3-10 carbocyclyl, C6-10 aryl, 3-10 membered heterocyclyl, 5-10 membered heteroaryl; or two geminal Rgg substituents can be joined to form =O or =S; wherein X— is a counterion.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

A "counterion" or "anionic counterion" is a negatively charged group associated with a cationic quaternary amino group in order to maintain electronic neutrality. Exemplary counterions include halide ions (e.g., F, Cl⁻, Br⁻, I⁻), NO$_3^-$, ClO$_4^-$, OH⁻, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R" groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{cc}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{cc}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{cc}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl) propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianylmethyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-4-trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N*-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is an sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(NR^{bb})R^{aa}$, $-C(NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

OTHER DEFINITIONS

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like (see, e.g., Berge, et al., J. Pharm. Sci. 66(1): 1-79 (January '77).

"Pharmaceutically acceptable vehicle" refers to a diluent, adjuvant, excipient or carrier with which a compound of the invention is administered.

"Pharmaceutically acceptable metabolically cleavable group" refers to a group which is cleaved in vivo to yield the parent molecule of the structural Formula indicated herein.

"Prodrugs" refers to compounds, including derivatives of the compounds of the invention, which have cleavable groups and become by solvolysis or under physiological conditions a compound of the invention that are pharmaceutically active in vivo.

"Solvate" refers to forms of the compound that are associated with a solvent or water (also referred to as "hydrate"), usually by a solvolysis reaction. This physical association includes hydrogen bonding. Conventional solvents include water, ethanol, acetic acid and the like. The compounds of the invention may be prepared e.g. in crystalline or liquid form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human", "patient" and "subject" are used interchangeably herein.

As used herein the term "enantiomerically pure" or "pure enantiomer" denotes that the compound comprises more than 95% by weight. In alternative embodiments, when specified, the term may refer to more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. The weights are based upon total weight of all enantiomers or stereoisomers of the compound.

As used herein and unless otherwise indicated, the term "enantiomerically pure R-compound" refers to at least 95% by weight R-compound and at most about 5% by weight S-compound. In alternative embodiments, when specified, the term can refer to at least about 99% by weight R-compound and at most about 1% by weight S-compound or at least about 99.9% by weight R-compound or at most about 0.1% by weight S-compound. In certain embodiments, the weights are based upon total weight of compound.

As used herein and unless otherwise indicated, the term "enantiomerically pure S-compound" or "S-compound" refers to at least about 95% by weight S-compound and at most about 5% by weight R-compound. In alternative embodiments, when specified, the term can refer to at least about 99% by weight S-compound and at most about 1% by weight R-compound or at least about 99.9% by weight S-compound and at most about 0.1% by weight R-compound. In certain embodiments, the weights are based upon total weight of compound.

These and other exemplary substituents are described in more detail in the Detailed Description, Examples, and claims. The invention is not intended to be limited in any manner by the above exemplary listing of substituents.

What is claimed is:

1. A compound 3-(4-hydroxyphenyl)-4-methyl-2-(4-{2-[(3R)-3-methylpyrrolidin-1-yl]ethoxy}phenyl)-2H-chromen-7-ol, which has the chemical structure:

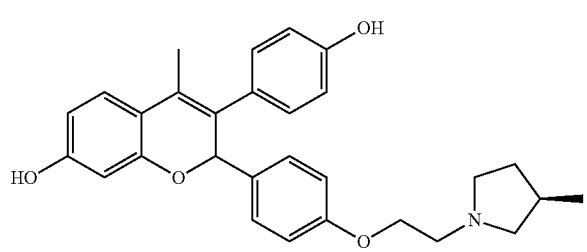

OP-1038 or a salt thereof.

2. A compound (2S)-3-(4-hydroxyphenyl)-4-methyl-2-(4-{2-[(3R)-3-methylpyrrolidin-1-yl]ethoxy}phenyl)-2H-chromen-7-ol which has the chemical structure:

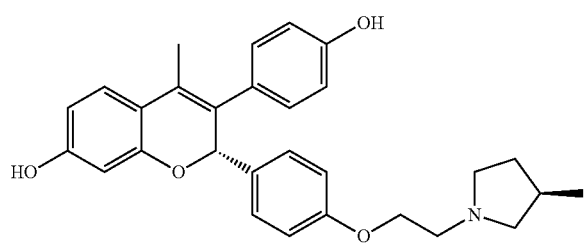

OP-1074 or a salt thereof.

3. A compound 3-(4-hydroxyphenyl)-4-methyl-2-(4-{2-[(3R)-3-methylpyrrolidin-1-yl]ethoxy}phenyl)-2H-chromen-7-ol, which has the chemical structure:

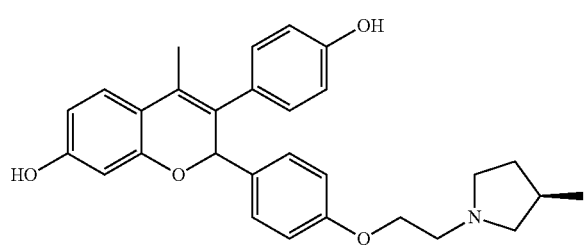

OP-1038 in the form of a solvate, hydrate, or N-oxide.

4. A compound (2S)-3-(4-hydroxyphenyl)-4-methyl-2-(4-{2-[(3R)-3-methylpyrrolidin-1-yl]ethoxy}phenyl)-2H-chromen-7-ol, which has the chemical structure:

OP-1074 in the form of a solvate, hydrate, or N-oxide.

5. The compound of claim 1 wherein the salt is pharmaceutically acceptable.

6. The compound of claim 2 wherein the salt is pharmaceutically acceptable.

7. The compound of claim 1 which is not in the form of a salt.

8. The compound of claim 2 which is not in the form of a salt.

9. A compound of the structure:

wherein $R_1$ and $R_2$ are independently:

H, halogen, natural or non-naturally occurring amino acid (bound through either the OC(O)— or C(O)O— (an ester) or the amino (through either —C(O)—N— or —N—C(O)— (an amide linkage)), $R^{10}$, —$OR^{10}$, or —$SR^{10}$ where $R^{10}$ is —C(=O)$R^{C1}$, —C(=O)O$R^{C1}$, —C(=O)S$R^{C1}$, —C(=O)N($R^{C1}$)$_2$; or polyethylene glycol, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;
—S(=O)$_2R^{C1}$, —S(=O)$_2$O$R^{C1}$, —S(=O)$R^{C1}$, —S(=O)O$R^{C1}$, —P(=O)$_2R^{C1}$, —P(=O)$_2$O$R^{C1}$, —P(=O)(O$R^{C1}$)$_2$, —P(=O)($R^{C1}$)$_2$, —P($R^{C1}$)(O$R^{C1}$) or OPO$_3$H$_3$; or oxygen attached to an oxygen protecting group (to produce OH on administration), sulfur attached to a sulfur protecting group (to produce SH or a disulfide on administration), or nitrogen attached to a nitrogen protecting group (to produce —NH— on administration);

and $R^{C1}$ can be independently selected from hydrogen, polyethylene glycol, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{C1}$ groups are joined to form an substituted or unsubstituted heterocyclic ring, or its pharmaceutically acceptable salt.

10. A compound of the structure:

wherein $R_1$ and $R_2$ are independently:

H, halogen, natural or non-naturally occurring amino acid (bound through either the OC(O)— or C(O)O— (an ester) or the amino (through either —C(O)—N— or —N—C(O)— (an amide linkage)), $R^{10}$, —$OR^{10}$, or —$SR^{10}$ where $R^{10}$ is —C(=O)$R^{C1}$, —C(=O)O$R^{C1}$, —C(=O)S$R^{C1}$, —C(=O)N($R^{C1}$)$_2$; or polyethylene glycol, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;
—S(=O)$_2R^{C1}$, —S(=O)$_2$O$R^{C1}$, —S(=O)$R^{C1}$, —S(=O)O$R^{C1}$, —P(=O)$_2R^{C1}$, —P(=O)$_2$O$R^{C1}$, —P(=O)(O$R^{C1}$)$_2$, —P(=O)($R^{C1}$)$_2$, —P($R^{C1}$)(O$R^{C1}$) or OPO$_3$H$_3$; or oxygen attached to an oxygen protecting group (to produce OH on administration), sulfur attached to a sulfur protecting group (to produce SH or a disulfide on administration), or nitrogen attached to a nitrogen protecting group (to produce —NH— on administration);

and $R^{C1}$ can be independently selected from hydrogen, polyethylene glycol, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{C1}$ groups are joined to form an substituted or unsubstituted heterocyclic ring, or its pharmaceutically acceptable salt.

11. The compound of claim 9, wherein $R_1$ and $R_2$ are —$OR^{10}$.

12. The compound of claim 10, wherein $R_1$ and $R_2$ are —$OR^{10}$.

13. The compound of claim 9, wherein $R_1$ is hydrogen.

14. The compound of claim 10, wherein $R_1$ is hydrogen.

15. The compound of claim 11, wherein —$OR^{10}$ is —O—C(=O) substituted or unsubstituted alkyl.

16. The compound of claim 12, wherein —$OR^{10}$ is —O—C(=O) substituted or unsubstituted alkyl.

17. The compound of claim 11, wherein —$OR^{10}$ is —O—C(=O) substituted or unsubstituted aryl.

18. The compound of claim 12, wherein —$OR^{10}$ is —O—C(=O) substituted or unsubstituted aryl.

19. The compound of claim 11, wherein —$OR^{10}$ is OPO$_3$H$_3$.

20. The compound of claim 12, wherein —$OR^{10}$ is OPO$_3$H$_3$.

21. The compound of claim 9, selected from the group consisting of:

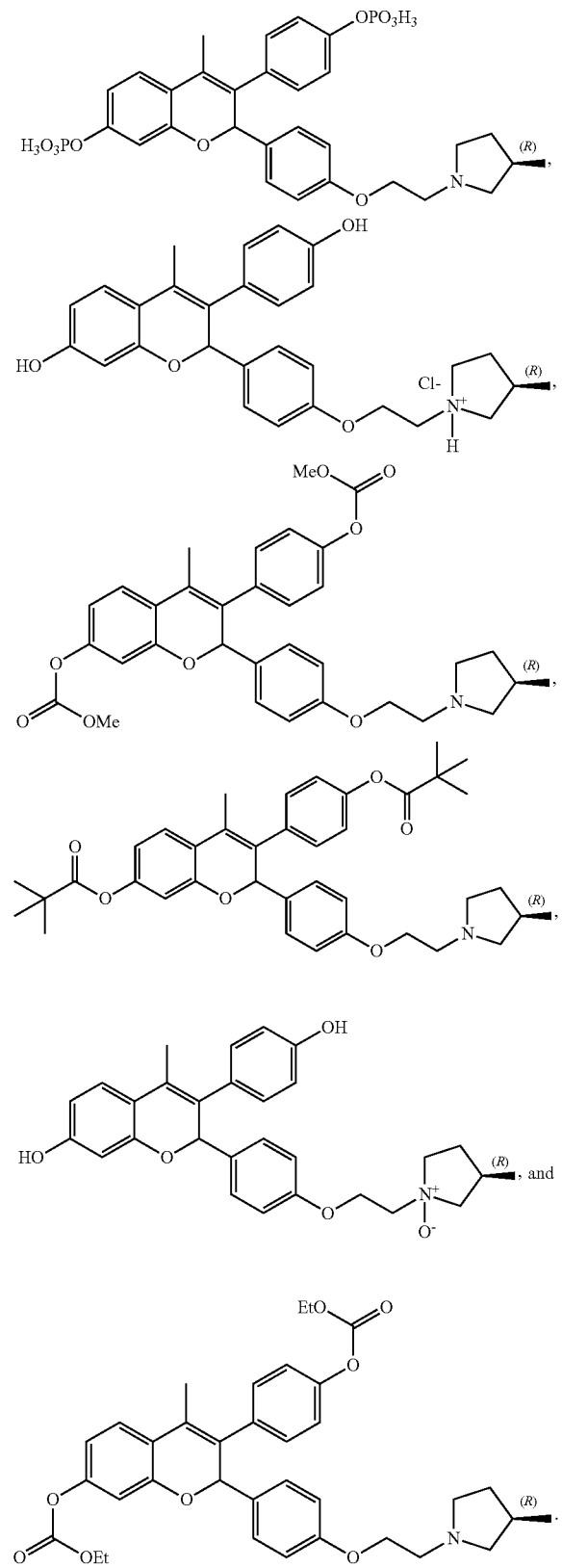

22. The compound of claim 10, selected from the group consisting of:

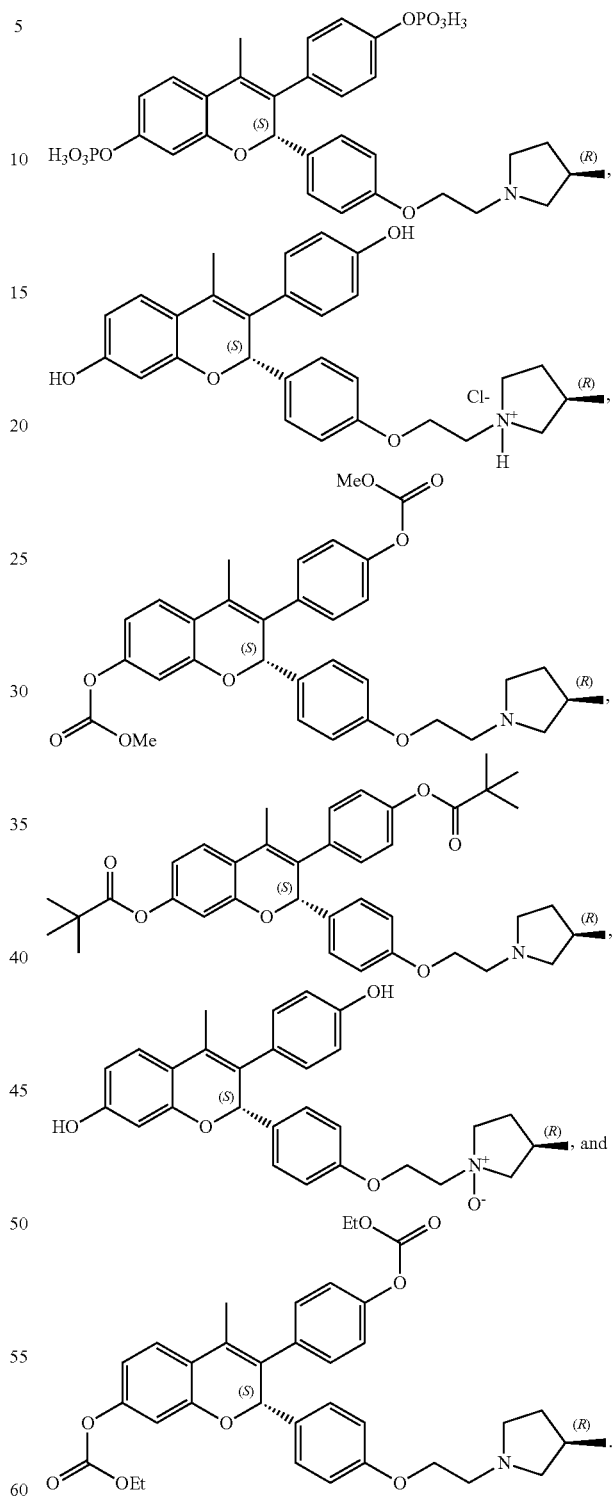

23. A pharmaceutical composition comprising a pharmaceutically effective amount of the compound of claim 1 in a pharmaceutically acceptable carrier.

24. A pharmaceutical composition comprising a pharmaceutically effective amount of the compound of claim 2 in a pharmaceutically acceptable carrier.

25. A pharmaceutical composition comprising a pharmaceutically effective amount of the compound of claim 3, 5, 7, 9, 11, 13, 15, 17, or 19 in a pharmaceutically acceptable carrier.

26. A pharmaceutical composition comprising a pharmaceutically effective amount of the compound of claim 4, 6, 8, 10, 12, 14, 16, 18 or 20 in a pharmaceutically acceptable carrier.

27. The pharmaceutical composition of claim 25 wherein the carrier is suitable for oral delivery.

28. The pharmaceutical composition of claim 26 wherein the carrier is suitable for oral delivery.

29. A method for treating a disorder mediated by the estrogen receptor in a patient, which comprises administering to the patient a therapeutically effective amount of the compound of claim 1, optionally in a pharmaceutically acceptable carrier.

30. A method for treating a disorder mediated by the estrogen receptor in a patient, which comprises administering to the patient a therapeutically effective amount of the compound of claim 2, optionally in a pharmaceutically acceptable carrier.

31. A method for treating a disorder mediated by the estrogen receptor in a patient, which comprises administering to the patient a therapeutically effective amount of the compound of claim 3, 5, 7, 9, 11, 13, 15, 17, or 19, optionally in a pharmaceutically acceptable carrier.

32. A method for treating a disorder mediated by the estrogen receptor in a patient, which comprises administering to the patient a therapeutically effective amount of the compound of claim 4, 6, 8, 10, 12, 14, 16, 18 or 20, optionally in a pharmaceutically acceptable carrier.

33. The method of claim 29, wherein the disorder is breast cancer.

34. The method of claim 30, wherein the disorder is breast cancer.

35. The method of claim 31, wherein the disorder is breast cancer.

36. The method of claim 32, wherein the disorder is breast cancer.

37. The method of claim 29, wherein the disorder is selected from the group consisting of ovarian, endometrial, or vaginal cancer, endometriosis or lung cancer.

38. The method of claim 30, wherein the disorder is selected from the group consisting of ovarian, endometrial, or vaginal cancer, endometriosis or lung cancer.

39. The compound of claim 1 for use in medical therapy.

40. The compound of claim 2 for use in medical therapy.

41. The compound of claim 3, 5, 7, 9, 11, 13, 15, 17, or 19, for use in medical therapy.

42. The compound of claim 4, 6, 8, 10, 12, 14, 16, 18 or 20, for use in medical therapy.

43. The method of claim 29, further comprising administering the compound in combination or alternation with another anti-cancer agent for the treatment of cancer.

44. The method of claim 30, further comprising administering the compound in combination or alternation with another anti-cancer agent for the treatment of cancer.

45. The method of claim 31, further comprising administering the compound in combination or alternation with another anti-cancer agent for the treatment of cancer.

46. The method of claim 32, further comprising administering the compound in combination or alternation with another anti-cancer agent for the treatment of cancer.

47. The method of claim 29, further comprising administering the compound in combination or alternation with estrogen or a partial estrogen receptor angatonist for the treatment of a postmenopausal disorder.

48. The method of claim 30, further comprising administering the compound in combination or alternation with estrogen or a partial estrogen receptor angatonist for the treatment of a postmenopausal disorder.

49. The method of claim 31, further comprising administering the compound in combination or alternation with estrogen or a partial estrogen receptor angatonist for the treatment of a postmenopausal disorder another anti cancer agent.

50. The method of claim 32, further comprising administering the compound in combination or alternation with estrogen or a partial estrogen receptor angatonist for the treatment of a postmenopausal disorder.

* * * * *